US008865699B2

(12) United States Patent
Ramsden et al.

(10) Patent No.: US 8,865,699 B2
(45) Date of Patent: Oct. 21, 2014

(54) AMINO TRIAZOLES AS PI3K INHIBITORS

(75) Inventors: Nigel Ramsden, Herts (GB); Kathryn Bell, London (GB); Andrew David Cansfield, Harston (GB); Jess Taylor, Dorking (GB); Mihiro Sunose, Sawston (GB); David Middlemiss, Stortford (GB); Gitte Neubauer, Mannheim (DE)

(73) Assignee: Cellzome Ltd., Brentford, Middlesex (GB)

( * ) Notice: Subject to any disclaimer, the term of this patent is extended or adjusted under 35 U.S.C. 154(b) by 556 days.

(21) Appl. No.: 12/744,940

(22) PCT Filed: Nov. 21, 2008

(86) PCT No.: PCT/EP2008/066001
§ 371 (c)(1),
(2), (4) Date: Sep. 30, 2010

(87) PCT Pub. No.: WO2009/068482
PCT Pub. Date: Jun. 4, 2009

(65) Prior Publication Data
US 2011/0021497 A1 Jan. 27, 2011

Related U.S. Application Data

(60) Provisional application No. 61/078,006, filed on Jul. 3, 2008, provisional application No. 61/086,963, filed on Jul. 7, 2008.

(30) Foreign Application Priority Data

Nov. 27, 2007 (EP) ..................................... 07121607

(51) Int. Cl.
*A01N 43/42* (2006.01)
*A61K 31/44* (2006.01)
*C07D 471/02* (2006.01)
*C07D 491/02* (2006.01)
*C07D 498/02* (2006.01)

(52) U.S. Cl.
USPC ................. 514/210.21; 514/303; 514/253.04; 514/233.2; 514/217.07; 514/256; 546/119; 544/362; 544/127; 544/333

(58) Field of Classification Search
USPC .................... 514/210.21, 303, 253.04, 233.2, 514/217.07, 256; 546/119; 544/362, 127, 544/333; 540/597
See application file for complete search history.

(56) References Cited

U.S. PATENT DOCUMENTS

| 6,514,989 | B1 | 2/2003 | Nettekoven et al. |
| 8,263,595 | B2 | 9/2012 | Swinnen et al. |
| 2010/0035756 | A1 | 2/2010 | Luthy et al. |
| 2011/0021497 | A1 | 1/2011 | Ramsden et al. |

FOREIGN PATENT DOCUMENTS

| DE | 287 263 | | 2/1991 |
| EP | 1 887 359 | | 2/2008 |
| MX | 2009/002171 | | 5/2009 |
| WO | WO 96/31517 | | 10/1996 |
| WO | 03010167 | | 2/2003 |
| WO | 2004072072 | | 8/2004 |
| WO | 2006018735 | | 2/2006 |
| WO | 2006038116 | | 4/2006 |
| WO | WO 2006/134056 | | 12/2006 |
| WO | 2007/095588 | | 8/2007 |
| WO | WO 2007/095588 | | 8/2007 |
| WO | 2008006540 | | 1/2008 |
| WO | WO 2008/015013 | | 2/2008 |
| WO | 2008/025821 | | 3/2008 |
| WO | 2008025821 | * | 3/2008 |
| WO | WO 2008/025821 | | 3/2008 |
| WO | WO 2009/010530 | | 1/2009 |
| WO | WO2009/027283 | | 3/2009 |
| WO | 2009068482 | | 6/2009 |

OTHER PUBLICATIONS

Yamazaki, et al., "Cyclization of isothiosemicarbazones. Part 10. A novel route to 2-amino[1,2,4]triazolo[1,5-a] pyrdine derivatives", J. Chem Soc. Perkin Trans., 1994, 1972-1999. (To Follow).
Bi, et al., "Proliferative defect and embryonic lethality in Mice homozygous for a deletion in the p110a Subunit of Phosphoinositide 3-Kinase", The Journal of Biological Chemistry, 1999, 274(16): 10963-10968.
Berg, et al., "Tec Family Kinase in T lymphocyte Development and Function", Annu. Rev. Immunol." 2005, 23: 549-600.
Brachmann, et al., "Phophoinostitide 3-Kinase Catalytic Subunit Deletion and Regulatory Subunit Deletion have opposite effects on Insulin sensitivity in Mice", Molecular and Cellular Biology, 2005, 25(5): 1596-1607.
Condliffe, et al., "Sequential activation of class IB and class IA PI3K is important for the primed respiratory burst of human but not murine neutrophils," Blood, 2005, 106(4): 1432-1440.
Forssell, et al., "Interleukin-2-Inducible TCell Kinase regulates mass cell degranulation and acute allergic responses", Am. J. Respir. Cell Mol. Biol., 2005: 32: 511-520.

(Continued)

*Primary Examiner* — Niloofar Rahmani
(74) *Attorney, Agent, or Firm* — Loretta J. Sauermelch; Alan X. Scrivner

(57) ABSTRACT

The invention relates to compounds of formula (I)

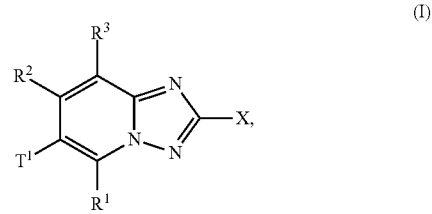

(I)

wherein X, $T^1$ and $R^1$ to $R^3$ have the meaning as cited in the description and the claims. Said compounds are useful as protein kinase inhibitors, especially inhibitors of PI3K, for the treatment or prophylaxis of immunological, inflammatory, autoimmune, or allergic disorders. The invention also relates to pharmaceutical compositions including said compounds, the preparation of such compounds as well as the production of and use as medicaments.

28 Claims, No Drawings

(56) References Cited

OTHER PUBLICATIONS

Fowell, et al., "Impaired NFATc translocation and failure of Th2 development in Itk-Deficient CD4+ TCell", Immunity, 1999, 11: 399-409.

Hata, et al., "Bruton's tyrosine kinase-mediated Interleukin-2 gene activation in mast cells", The Journal of Biological Chemistry, 1998, 273(18): 10979-10987.

Hirsch, et al., "Central Role for G Protien-coupled Phosphoinositide 3-Kinase y in Inflammation", Science, 2000, 1049-1053.

Li, et al., "Roles of PLC-B2 and -B3 and PI3Ky in chemoattractant-mediated signal transduction", Science, 2000, 287: 1046-1049.

Lin, et al., "Selective Itk inhibitors block TCell activation and murine lung inflammation", Biochemistry, 2004, 43: 11056-11062.

Liu, et al., "TCell receptor-initiated calcium release is uncoupled from capacitative calcium entry in Itk-deficient TCells", J. Exp. Med., 1998, 187(10), 1721-1727.

Lopez-Llasaca, et al., "Linkage of G protein-coupled receptors to the MAPK Signallin Pathway through PI 3-kinase y", Science, 1997, 275: 394-397.

Matsumoto, et al., "Identification of highly expressed genes in perihperal blood TCells from patients with atopic dermatitis", International Archives of Allergy and Immunology, 2002, 129: 327-340.

Mueller, et al., "Attenuation of immunological symptoms of allergic asthma in mice lacking the Tyrosin Kinase Itk1", The Journal of Immunologies, 2003, 170: 5056-5063.

Okkenhaug, et al., "Impaired and TCELL antigen receptor signaling in p110o PI 3-Kinase mutant mice", Science, 2002, 297: 1031-1034.

Rubio, et al., "Interaction of Ras with phosphoinositide 3-kinase y", Biochem. J., 1997, 326: 891-895.

Sasaki, et al., "Function of PI3Ky in thymocyte development, TCELL activation and neutrophil migration", Science, 2000, 287: 1040-1046.

Schaeffer, et al., "Requirement for Tec Kinases Rik and Itk in TCELL Receptor signaling and immunity", Science, 1999, 284: 638-641.

Schwartzberg, et al., "Tec-Family Kinases: Regulators of T-Helper-Cell differentiation", Nature Reviews Immunology, 2005, 5: 284-295.

Smith, et al., "The Tec family of cytoplasmic tyrosine kinases: mammalian Btk, Bmx, Itk, Tec, Txk and homologs in other species", BioEssays 23.5, 2001, 436-556.

Stephens, et al., "A novel phosphoinositide 3 Kinase activity in myeloid-derived cells is activated by G protein by subunits", Cell, 1994, 77: 83-93.

Stephens, et al., "Protein kinase B kinases that mediate phosphatidylinositol 3, 4, 5-trisphosphate-dependent activation of Protein Kinase B", Science, 1998, 279: 710-714.

Stephens, et al., "The GBy sensitivity of a PI3K is dependent upon a tightly associated adaptor", Cell, 1997, 89: 105-114.

Thomas, et al., "Airway inflammation: chemokine-included neutrophilia and the class I phosphoinositide 3-kinases", Eur. J. Immunol., 2005, 35: 1283-1291.

Wong, "Inhibitors of the tyrosine Kinase signaling cascade for asthma", Current Opinion in Pharmacology, 2005, 5: 1-8.

Nettekoven, et al., "Synthetic access to 2-amido-5-aryl-8-methoxy-triazolopyridine and 2-amido-5-morpholino-9-methoxy-triazolopyridine derivatives as potential inhibitors of the adenosine receptor subtypes" Synthesis, 2003, 1649-1652 (Abstract Only).

International Search Report (Form PCT/ISA/210), issued in the corresponding application No. PCE/EP2007/059051, completed on Nov. 23, 2007 and mailed on Dec. 3, 2007.

International Search Report for PCT/EP2008/066001, mailed Jan. 29, 2009.

International Preliminary Report on Patentability for PCT/EP2008/06601, mailed Jun. 1, 2010.

Written Opinion of the International Searching Authority for PCT/EP2008/066001.

Golub, et al., "Molecular classification of cancer: class discovery and class prediction by gene expression monitoring", Science, 1999, 286(5439): 531-7. (To follow).

Lala, et al., "Role of nitric oxide in tumor progression: lessons from experimental tumors", Cancer Metastasis Rev, 1998, 17(1): 91-106. (To follow).

Anieto and Gruenberg, "Chapter 4.3 Subcellular Fractionation of Tissue Culture Cells," in *Current Protocols in Protein Science*, Editors: John.E. Coligan, Ben M. Dunn, Hidde L Ploegh, David W. Speicher, Paul T. Wingfield; John Wiley & Sons, Inc., ISBN: 0-471-14098-8 (2003).

Ausubel et al., "Chapter 11 Immunology," pp. 11-1 to 11-29 in: *Short Protocols in Molecular Biology*. Fifth Edition, John Wiley & Sons, Inc., New York, (2002).

Bader et al., "Oncogenic PI3K Deregulates Transcription and Translation," *Nat. Rev. Cancer* 5:921-929 (2005).

Bain et al., "The Selectivity of Protein Kinase Inhibitors: A Further Update," *Biochem. J.* 408:297-315 (2007).

Balla and Balla, "Phosphatidylinositol 4-Kinases: Old Enzymes with Emerging Functions," *TRENDS in Cell Biology* 16:351-361 (2006).

Bantscheff et al., "Quantitative Chemical Proteomics Reveals Mechanisms of Action of Clinical ABL Kinase Inhibitors," *Nat Biotechnol*. 25;1035-1044 (2007).

Biddison, W.E., "Chapter 2.2 Preparation and Culture of Human Lymphocytes," pp. 2.2.1-2.213 in *Current Protocols in Cell Biology*, John Wiley & Sons, Inc. (1998).

Breinbauer et al., "Natural Product Guided Compound Library Development," *Curr Med Chem*. 9:2129.2145 (2002).

Carpenter et al., "Purification and Characterization of Phosphoinositide 3-Kinase from Rat Liver," *J Biol Chem*. 265:19704-19711 (1990).

Castle, "Chapter 4.2: Purification of Organelles from Mammalian Cells" pp. 4.2.1-4.2.57 in *Current Protocols in Protein Science* John Wiley & Sons, Inc., (2004).

Deora et al., "A Redox-Triggered Ras-Effector Interaction. Recruitment of Phosphatidylinositol 3'-Kinase to Ras by Redox Stress," *J Biol Chem*. 273:29923-29928 (1998).

Elias and Gygi, "Target-Decoy Search Strategy for Increased Confidence in Large-Scaled Protein Identifications by Mass Spectrometry," *Nat. Methods* 4:207-214 (2007).

Fenteany at al., "Inhibition of Proteasome Activities and Subunit-Specific Amino-Terminal Threonine Modification by Lactacystin," *Science* 268:726-731 (1995).

Fruman et al., "Phosphoinositide Kinases," *Annu Rev Biochem*. 67:481-507 (1998).

Fuchikami et al., "A Versatile High-Throughput Screen for Inhibitors of Lipid Kinase Activity: Development of an Immobilized Phospholipid Plate Assay for Phosphoinositide 3-Kinase γ," *J. Biomol. Screening* 7:441-450 (2002).

Garcia-Martinez et al., "Ku-0063794 is a Specific Inhibitor of the Mammalian Target of Rapamycin (mTOR)," *Biochem. J.* 421:29-42 (2009).

Gharbi et al., "Exploring the Specificity of the PI3K Family Inhibitor LY294002," *Biochem J*. 404:15-21 (2007).

Glickman et al., "A Comparison of ALPHAScreen, TR-FRET, and TRF as Assay Methods for FXR Nuclear Receptors," *J. Biomol Screen* 7:3-10 (2002).

Karaman et al., "A Quantitative Analysis of Kinase Inhibitor Selectivity," *Nat Biotechnol*. 26:127-32 (2008).

Karwa and Mitra "'Techniques for the Extraction, Isolation, and Purification of Nucleic Acids'; Chapter 8 in Sample Preparation Techniques in Analytical Chemistry," *Chemical Analysis* 162:331-375 (2003).

Kashem et al., "Three Mechanistically Distinct Kinase Assays Compared: Measurement of Intrinsic ATPase Activity Identified the Most Comprehensive Set of ITK Inhibitors," *J. Biomol. Screening* 12:70-83 (2007).

Kersey et al., "Technical Brief: The International Protein Index: An Integrated Database for Proteomics Experiments," *Proteomics* 4:1985-1988 (2004).

Lingaraj et al., "A High-Throughput Liposome Substrate Assay with Automated Lipid Extraction Process for PI 3-Kinase," *J. Biolmol. Screen*. 13:906-911 (2008).

Mann et al., "Analysis of Proteins and Proteomes by Mass Spectrometry," *Ann. Rev. Biochem*. 70:437-473 (2001).

(56) References Cited

OTHER PUBLICATIONS

Moger et al., "The Application of Fluorescense Lifetime Readouts in High-Throughput Screening," *J. Biomol. Screening* 11: 765-772 (2006).
Patricelli et al., "Functional Interrogation of the Kinome Using Nucleotide Acyl Phosphates," *Biochemistry*, 46:350-358 (2007).
Perkins et al., "Probability-Based Protein Identification by Searching Sequence Databases Using Mass Spectrometry Data," *Electrophoresis* 20:3551-3567 (1999).
Petty, "Overview of the Physical State of Proteins Chapter 1", Unit 5.1.1-5.1.10 in *Current Protocols in Cell Biology* John Wiley & Sons, Inc., (1998).
Pomel et al., "Furan-2-ylmethylene Thiazolidinediones as Novel, Potent, and Selective Inhibitors of Phosphoinositide 3-Kinase Gamma," *J. Med. Chem.* 49:3857-3871 (2006).
Ross et al., "Multiplexed Protein Quantitation in *Saccharomyces cerevisae* Using Amine-Reactive Isobaric Tagging Reagents," *Mol. Cell. Proteomics* 3:1154-1169 (2004).
Sasaki et al., "Colorectal carcinomas in mice lacking the catalytic subunit of PI(3)Kgamma," *Nature*. 406:897-902 (2000).
Shevchenko et al., "Mass spectrometric sequencing of proteins silver-stained polyacrylamide gels," *Anal Chem*. 68:850-858 (1996).
Subramanian, "Immunoaffinity Chromatography," *Molecular Biotechnology* 20:41-47 (2002).
Tolias et al., "Type I Phosphatidylinositol-4-Phosphate 5-Kinases Synthesize the Novel Lipids Phosphatidylinositol 3, 5-Bisphosphate and Phosphatidylinositol 5-Phosphate," *J. Biol. Chem.* 273:18040-18046 (1998).
Vedvik et al., "Overcoming Compound Interference in Fluorescence Polarization-Based Kinase Assays Using Far-Red Tracers," *Assay Drug Dev. Technol.* 2: 193-203 (2004).
Weernink et al., "Regulation and Cellular Roles of Phosphoinositide 5-Kinases," *Eur. J. Pharmacol.* 500:87-99 (2004).
Wingfield, Paul T., "Production of Recombinant Proteins," Chapter 5, Unit 5.0.1-5.0.3 in: *Current Protocols in Protein Science*, Editors: John. E. Coligan, Ben M. Dunn, Hidde L. Ploegh, David W. Speicher, Paul T. Wingfield; John Wiley & Sons Inc., ISBN: 0-471-14098-8 (2002).
Wu et al., "Comparative Study of Three Proteomic Quantitative Methods, DIGE, cICAT, and iTRAQ, Using 2D Gel- or LC-MALDI TOF/TOF," *J. Proteome Res.* 5:651-658 (2006).
Wymann and Schneiter, "Lipid Signalling in Disease," *Nat. Rev. Mol. Cell. Bio.* 9:162-176 (2008).
Zaman et al., "Fluorescence Assays for High-Throughput Screening of Protein Kinases," *Comb. Chem. High Throughput Screen* 6: 313-320 (2003).
Zeman et al., "Enzyme Fragment Complementation Binding Assay for P38α Mitogen-Activated Protein Kinase to Study the Binding Kinetics of Enzyme Inhibitors," *Assay Drug Dev. Technol.* 4:411-420 (2006).
Zhang et al., "Time-Resolved Forster Resonance Energy Transfer Assays for the Binding of Nucleotide and Protein Substrates to P38α Protein Kinase," *Analytical Biochemistry* 343:76-83 (2005).
International Preliminary Report on Patentability for International Application No. PCT/EP2010/002987, issued Nov. 22, 2011.
International Search Report for International Application No. PCT/EP2010/002987, completed Aug. 13, 2010, mailed Aug. 20, 2010.
Ali et al., 2004, Nature 431:1007-1011.
Asakura et al., 2007, World J. Gastroenterol. 13(15):2145-9.
Bader et al., 2005, Nat. Rev. Cancer 5(12): 921-929.
Barber et al., 2005, Nat. Med. 11(9):933-935.
Benistant et al., 2000, Oncogene 19(44):5083-5090.
Bille et al., 1982, J. Infect. Dis. 146:220-6.
Billottet et al., 2006. Oncogene 25(50):6648-6659.
Bondeva et al., "Bifurcation of Lipid and Protein Kinase Singals of PI3Ky to the Protein Kinases PKB and MAPK," Science, vol. 282:293-296.
Bruno et al., 2005, J. Immunol. 174: 8090-96.
Busse and Lemanske, 2001, N. Engl. J. Med. 344:350-362.
Camps et al., 2005. Nat. Med. 11(9):936-43.
Cantley, 2002, Science 296(5573):1655-7.
Carpenter et al., 1990, J. Biol. Chem. 265,19704-19711.
Carroll etal., 2007. American Family Physiscian 75(1): 1513-1520.
Cauwels et al., 2006, J. Clin. Invest. 116(8):2244-51.
Chang et al., 2007, PNAS 104 (19):8077-82.
Cohen et al., 2007, Orphanet J. Rare Dis. 2:34.
Crow et al., 2004, Circ. Res. 95(10):957-970.
D'Cruz et al., 2007, Lancet 369(9561 ):587-596.
Doukas et al., 2006, PNAS 103(52):19866-19871.
Doukas et al., 2007, Biochem. Soc. Trans. 35(Pt2):204-206.
Erhardt et al., 2007, J. Virol. 81 (7): 3058-67.
Falasca et al., 2007, Biochem. Soc. Trans. 35:211-4.
Ferguson et al., 2007, Nat. Cell Biol. 9(1 ):86-91.
Firestein 2003, Nature 423:356-361.
Foukas et al., 2006, Nature, 441(7091):366-70.
Frangogiannis et al., 2002, Cardiovasc. Res. 53(1):31-47.
Fruman et al., 1998, Annu. Rev. Biochem. 67:481-507.
Fuchikami et al., 2002, J. Biomol. Screening 7, 441-450.
Hale et al., 2006, PNAS 103,14194-14199.
Hanahan and Weinberg, 2000. The Hallmarks of Cancer. Cell 100, 57-70.
Hawkins et al., 2006, Biochem. Soc. Trans. 34:647-62.
Hemmer et al., 2002, Nat. Rev. Neuroscience 3,291-301.
Hennessy et al., 2005, Nat. Rev. Drug Discovery 4(12):988-1004.
Hirsch et al., 2006, Thromb. Haemost. 95(1):29-35.
Jackson, et al., "PI 3-kinase p110B: a new target for antithrombotic therapy," Nature Medicine, vol. 11, No. 5, May 2005:507-514.
Kang et al., 2006, PNAS 103(5): 1289-1294.
Knight et al., 2006, Cell 125(4): 733-747.
Knobbe and Reifenberger, 2003, Brain Pathol. 13(4):507-518.
Kratz et al., 2002, Blood 99:372-374.
Leopoldt et al., 1998, J. Biol. Chem. 273(12):7024-9.
Lindmo et al., 2006, J. Cell Sci. 119:605-14.
Lupia et al., 2004. Am. J. Pathol. 165(6):2003-2011.
Mcintosh et al., 1992, FASEB J 6:2775-82.
Molad Y et al., 2004, J. Investig. Med. 52(1 ):58-61.
Nashed et al., 2007, Eur. J. Immunol. 37:416-424.
Niswender et al., 2003, Diabetes 52:227-231.
Palanki et al., 2007, J. Med. Chem. 50(18)4279-4294.
Patrucco et al., 2004, Cell 118(3):375-87.
Plum et al., 2005, Trends Endocrinol. Metab. 16(2):59-65.
Pomel et al., 2006, J. Med. Chem. 49(13):3857-71.
Rommel et al., 2007, Nat. Rev. Immunol. 7(3):191-201.
Ruckle et al., 2006, Nat. Rev. Drug Discov. 5(11):903-18.
Ryckman et al., 2003, Arthritis & Rheumatism 48 (8): 2310-20.
Sadhu et al., 2003, Biochem. Biophys. Res. Commun. Sep. 5, 2003;308 (4):764-769.
Samuels et al., 2004, Science 304:554.
Samuels et al., 2005, Cancer Cell 7(6):561-573.
Schon et al., 2005, New Engl. J. Med. 352:1899-1912.
Seki et al., 1997, DNA Research 4:355-358.
Shapiro 2005, N. Engl. J. Med. 352, 2016-2019.
Stoyanov et al., 1995, Science 269:690-693.
Suzuki et al., Chem Commun. (1979) 866.
Vanhaesebroeck et al., 1997, Proc. Natl. Acad Sci. 94:4330-4335.
Vanhaesebroeck et al., 2001, Annu. Rev. Biochem. 70:535-602.
Vanhaesebroeck et al., 2005. Trends in Biochemical Sciences 30, 194-204.
Voigt et al., 2006, J. Biol. Chem. 281(15):9977-86.
Walker et al., 2006, Drug Discovery Today: Disease Mechanisms, 3 (1):63-69.
Wymann et al., 2003, Trends Pharmacol. Sci. 24(7):366-76.
Wymann et al., 2005, Curr Opin Cell Biol. 17(2):141-9.
Xu et al., 2005, J. Clin. Inv., 115 (4): 951-8.
Laffargue, et al., "Phosphoinositide 3-Kinase y Is an Essential Amplifer of Mast Cell Function," Immunity, vol. 16, 441-451, Mar. 2002 by Cell Press.

\* cited by examiner

AMINO TRIAZOLES AS PI3K INHIBITORS

The present invention relates to a novel class of kinase inhibitors, including pharmaceutically acceptable salts, prodrugs and metabolites thereof, which are useful for modulating protein kinase activity for modulating cellular activities such as signal transduction, proliferation, differentiation, programmed cell death, migration and cytokine secretion. More specifically the invention provides compounds which inhibit, regulate and/or modulate kinase activity, in particular PI3K activity, and signal transduction pathways relating to cellular activities as mentioned above. Furthermore, the present invention relates to pharmaceutical compositions comprising said compounds, e.g. for the treatment of diseases such as immunological, inflammatory, autoimmune and allergic disorders, and processes for preparing said compounds.

Protein and lipid kinases participate in the signaling events which control the activation, growth, differentiation and survival of cells in response to extracellular mediators or stimuli such as growth factors, cytokines or chemokines. In general, protein kinases are classified in two groups, those that preferentially phosphorylate tyrosine residues and those that preferentially phosphorylate serine and/or threonine residues in their protein substrates. By contrast, lipid kinases phosphorylate a variety of lipid substrates.

Inappropriately high protein or lipid kinase activity is involved in many diseases including cancer, metabolic diseases, immunological diseases and inflammatory disorders. This can be caused either directly or indirectly by the failure of control mechanisms due to mutation, overexpression or inappropriate activation of the enzyme. In all of these instances, selective inhibition of the kinase is expected to have a beneficial therapeutic effect.

Phosphoinositide 3-kinases (also called Phosphatidylinositol 3-kinases, PI3Ks) represent a group of lipid kinases that play pivotal roles in numerous intracellular signaling events, for example in T-cell receptor signaling. Some members of the PI3K family also display protein kinase activity. (Cantley, 2002, Science 296(5573):1655-7; Vanhaesebroeck et al., 2001, Annu Rev. Biochem. 70:535-602; Bondeva et al., 1998, Science 282(5387):293-6).

PI3Ks belongs to a superfamily of signaling lipid kinases that catalyse the phosphorylation of phosphatidylinositol-4, 5-bisphosphate (PtdIns(4,5)P2 or phosphatidylinositol (PtdIns) at the 3'-OH group, giving rise to the second messengers phosphatidylinositol-3,4,5-trisphosphate (PtdIns(3,4,5)P3) or phosphatidylinositol-3-phosphate (PtdIns(3)P). PtdIns(3, 4,5)P3 can be converted into PtdIns(3,4)P2 by SH2-containing inositol phosphatase (SHIP), or can be dephosphorylated by phosphatase and tensin homologue (PTEN) phosphatase to regenerate PtdIns(4,5)P2. The 3'-phosphorylated phosphoinositides, PtdIns(3,4,5)P3, PtdIns(3,4)P2 PtdIns(4,5)P2, PtdIns(5)P and PtdIns(3)P, recruit and activate various signalling proteins (PtdInsbinding proteins; PtdIns-BPs) through direct lipid-protein interactions (Fruman et al., 1998, Annu Rev. Biochem. 67:481-507; Hawkins et al., 2006, Biochem. Soc. Trans. 34:647-62).

Phosphatidylinositol-3,4,5-trisphosphate (PtdIns(3,4,5) P3) has an important role as second messenger by working as a docking platform for lipid-binding domains, such as the pleckstrin homology (PH) domains of various cellular proteins. These include kinases (such as 3-phosphoinositide-dependent protein kinase 1 (PDK1) and protein kinase B (PKB)/Akt) that trigger downstream kinase cascades, and guanine-nucleotide exchange factors (such as Vav and P-Rex) that control the activity of small GTPases (Wymann et al., 2005, Curr Opin Cell Biol. 17(2):141-9; Wymann et al., 2003, Trends Pharmacol. Sci. 24(7):366-76).

PI3-kinase activation is believed to be involved in a variety of signal transduction pathways, including those essential to cell proliferation, cell differentiation, cell growth, cell survival, apoptosis, adhesion, chemotaxis, invasion, cytoskeletal rearrangement, contraction, phagocytosis vesicle trafficking, receptor internalization, secretion, protein synthesis and metabolic pathways. PI3K gamma (γ) and delta (δ) isoforms appear to be involved in a number of aspects of leukocyte activation (Rommel et al., 2007, Nat. Rev. Immunol. 7(3): 191-201; Ruckle et al., 2006, Nat. Rev. Drug Discov. 5(11): 903-18).

Different types of PI3K have been identified and grouped into three classes according to their primary and secondary structures, mode of regulation and substrate specificity. Class I PI3K has been the most extensively studied so far, and includes heterodimeric proteins that consist of a catalytic and a regulatory adaptor subunit, the nature of which determines a further subdivision into class IA and IB PI3K. Class II PI3K uses PtdIns as in vivo substrate, yielding phosphatidylinositol-3-phosphate (PtdIns(3)P). Some evidence has been presented that class II enzymes, similarly to class I can be activated by external stimuli via receptor tyrosine kinases (RTKs), cytokine receptors and integrins, suggesting roles in cancer, wound healing and insulin signaling. By contrast, the class III PI3K, represented by a single species (hVps34) in humans, has relatively high activity even in resting cells. The class III represents the most ancient form of PI3K and it uses exclusively PtdIns as a substrate to produce PtdIns(3)P. This class of PI3Ks is involved in endocytic membrane traffic, phagosom maturation and autophagy (Falasca et al., 2007, Biochem. Soc. Trans. 35:211-4; Lindmo et al., 2006, J. Cell Sci. 119:605-14).

The class IA—PI3Kα, β and δ (PIK3CA, PIK3CB and PIK3CD)—consists of a SH2-domain-containing regulatory subunit (p85; five distinct isoforms of which have been identified) that forms a complex with one of three catalytic subunits, p110α, p110β or p110δ (Bader et al., 2005, Nat. Rev. Cancer 5(12):921-9).

Genetic polymorphisms within the PI3K pathway are also associated with an increased risk of type 2 diabetes. Downstream of the insulin-like growth factor 1 (IGF1) receptor, signaling through class I PI3K controls growth and development. Amplification and point mutations of the gene encoding PI3Kα that increase the enzymatic activity of the protein have been frequently found in human cancers (Bader et al., 2005, Nat. Rev. Cancer 5(12):921-9).

PI3K activation and PIP3 production are fundamental for most biological responses exerted by insulin. Activated insulin receptor (IR) triggers PI3K activity by binding and phosphorylating adaptor proteins of the insulin receptor substrate (IRS) family. Upon phoshphorylation IRS serves as a docking site for p85 regulatory subunits that consequently recruit p110 enzymes (mainly α and β isoforms). PIP3 production in turn activates downstream effectors that control various metabolic processes such as glucose uptake, triglyceride formation, glycogen synthesis, lipolysis and hepatic gluconeogenesis inhibition (Knight et al., 2006, Cell 125(4): 733-747; Foukas et al., 2006, Nature, 441(7091):366-70).

PI3Kβ has been implicated in regulating the formation and stability of integrin α(IIb)β(3), which is necessary for the activation and aggregation of platelets. Isoform-selective PI3K p110β inhibitors have been developed which in vivo eliminate occlusive thrombus formation but do not prolong bleeding time. These studies define PI3K p110β as an important new target for antithrombotic therapy (Jackson et al., 2005, Nat. Med. 11 (5):507-14).

PI3Kδ is predominantly expressed in the haematopoietic system and PI3Kδ-deficient mice are viable, fertile, apparently healthy and have a normal life span (Vanhaesebroeck et al., 2005. Trends in Biochemical Sciences 30, 194-204). PI3Kδ has important roles in T- and B-cell signaling, mast-cell-mediated allergic responses, the neutrophils oxidative burst and, possibly, extravasation. PI3K inhibitors selective for PI3Kδ were reported to block neutrophil activation in an animal model for neutrophil activation, thus pointing to PI3kδ as a target for the development of anti-inflammatory drugs (Sadhu et al., 2003, Biochem. Biophys. Res. Communications 308, 764-769).

PI3Kγ, the only member of class IB (PIK3CG), associates with either of two regulatory subunits, p101 and p84, that control its activation and subcellular location. PI3Kγ activation is driven by the direct association of its catalytic domain with the βγ subunits of G proteins following activation of pertussis-toxin-sensitive Gαi-coupled G-protein-coupled receptors (GPCRs). In addition, PI3Kγ can be activated by Ras by a direct interaction with the catalytic subunit. Beside its lipid kinase activity, PI3Kγ has a protein kinase activity. It uses the regulatory subunits as well as itself as substrate and both events result in an increase of the lipid kinase activity (Leopoldt et al., 1998, J. Biol. Chem. 273(12):7024-9).

Other proteins, for example phosphodiesterases (PDEs) can bind to PI3Kγ, indicating a protein-scaffold function in addition to its enzymatic activity. PI3Kγ was also shown to activate MEK kinase as well as to mediate shear-sensitive triggering of the JNK kinase pathway in endothelial cells (Patrucco et al., 2004, Cell 118(3):375-87; Voigt et al., 2006, J. Biol. Chem. 281(15):9977-86).

The mouse PI3Kγ protein is encoded by the Pik3cg locus. Mice lacking functional PI3Kγ(PI3 Kg−/− mice) were viable, fertile, and displayed a normal life span in a conventional mouse facility. Further studies revealed that neutrophils of these mice were unable to produce PtdIns (3,4,5) P3 when stimulated with GPCR agonists such as formylated bacterial peptides (N-formyl-Met-Leu-Phe, fMLP), complement C5a or interleukin 8 (IL-8). This observation demonstrates that PI3Kγ is the sole PI3K isoform that is coupled to these GPCRs in neutrophils (Vanhaesebroeck et al., 2005. Trends in Biochemical Sciences 30, 194-204). Moreover, PtdIns (3, 4, 5) P3-dependent activation of protein kinase B (PKB) was also absent in those neutrophils, while PKB could still be activated by GM-CSF or IgG/C3b-coated zymosan. Pi3kcg−/− mice showed impaired thymocyte development and increases in neutrophil, monocyte, and eosinophil populations. Furthermore, neutrophils and macrophages isolated from Pi3kcg−/− mice exhibited severe defects in migration and respiratory burst in response to GPCR agonists and chemotactic agents. Work with knockout mice also established that PI3Kγ is required for the homing of dendritic cells to lymph nodes and in the development and activation of T lymphocytes (together with PI3Kδ). In concert with IgE-dependent activation of PI3Kδ, PI3Kγ also contributes to the activation of mast cell secretion by adenosine. Its involvement in the stimulation of autocrine and paracrine regulatory loops by purines has also been observed in other cell types. PI3Kγ also contributes to the activation of platelet aggregation by ADP in concert with PI3Kβ (Ferguson et al., 2007, Nat. Cell Biol. 9(1): 86-91).

Collectively, the class IB phosphoinositide 3-kinase PI3Kγ seems to be pivotal in the control of leukocyte trafficking and accordingly the development of isotype-selective inhibitors of PI3Kγ should be an attractive anti-inflammatory therapeutic strategy (Rommel et al., 2007, Nat. Rev. Immunol. 7(3): 191-201; Ruckle et al., 2006, Nat. Rev. Drug Discov. 5(11): 903-18).

PI3Kγ plays a crucial role in both vascular cells and white blood cells. It controls diverse immune modulatory and vascular functions like respiratory burst, cell recruitment, mast cell reactivity, platelet aggregation, endothelial activation as well as smooth muscle contractility. The relative specificity of these events suggests that blocking PI3Kγ function might turn out beneficial for diseases like inflammation, allergy, autoimmunity, thrombosis, and major cardiovascular disorders like hypertension and atherosclerosis (Hirsch et al., 2006, Thromb. Haemost. 95(1):29-35). In addition, it was demonstrated that PI3Kγ plays a role in a mouse model for pancreatitis. The lethality of the choline-deficient/ethionine-supplemented diet-induced pancreatitis was significantly reduced in mice lacking PI3Kγ (Lupia et al., 2004. Am. J. Pathol. 165 (6):2003-2011).

Recently, the development of potent and selective PI3Kγ inhibitors was reported (Pomel et al., 2006, J. Med. Chem. 49(13):3857-71; Palanki et al., 2007. J. Med. Chem. 50(18): 4279-4294).

Thus, an object of the present invention is to provide a new class of compounds as kinase inhibitors, especially as PI3K inhibitors, which may be effective in the treatment or prophylaxis of immunological, inflammatory, autoimmune, allergic disorders or other diseases or disorders associated with PI3K. Furthermore, another object of the present invention is to provide said compounds, which may be effective in the treatment or prophylaxis of cancer or cardiovascular disorders associated with PI3K.

Accordingly, the present invention provides compounds of formula (I)

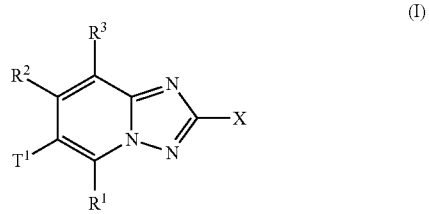

or a pharmaceutically acceptable salt, prodrug or metabolite thereof, wherein

X is OH; SH; $NH_2$; $NHC(O)NH_2$; or $NHC(S)NH_2$;

$R^1$, $R^2$, $R^3$ are independently selected from the group consisting of H; halogen; CN; $C(O)OR^4$; $OR^4$; $C(O)R^4$; $C(O)N(R^4R^{4a})$; $S(O)_2N(R^4R^{4a})$; $S(O)N(R^4R^{4a})$; $S(O)_2R^4$; $S(O)R^4$; $N(R^4)S(O)_2N(R^{4a}R^{4b})$; $N(R^4)S(O)N(R^{4a}R^{4b})$; $SR^4$; $N(R^4R^{4a})$; $OC(O)R^4$; $N(R^4)C(O)R^{4a}$; $N(R^4)S(O)_2R^{4a}$; $N(R^4)S(O)R^{4a}$; $N(R^4)C(O)N(R^{4a}R^{4b})$; $N(R^4)C(O)OR^{4a}$; $OC(O)N(R^4R^{4a})$; and $C_{1-6}$ alkyl, wherein $C_{1-6}$ alkyl is optionally substituted with one or more halogen, which are the same or different;

$R^4$, $R^{4a}$, $R^{4b}$ are independently selected from the group consisting of H; and $C_{1-6}$ alkyl, wherein $C_{1-6}$ alkyl is optionally substituted with one or more halogen, which are the same or different;

$T^1$ is 4 to 7 membered heterocyclyl; 9 to 11 membered heterobicyclyl; phenyl; naphthyl; indenyl; or indanyl; wherein $T^1$ is optionally substituted with one or more $R^5$ and/or one or more $R^6$;

$R^5$ is halogen; CN; $C(O)OR^7$; $OR^7$; oxo (=O), where the ring is at least partially saturated; $C(O)R^7$; $C(O)N(R^7R^{7a})$; $S(O)_2$ $N(R^7R^{7a})$; $S(O)N(R^7R^{7a})$; $S(O)_2R^7$; $S(O)R^7$; $N(R^7)S(O)_2N(R^{7a}R^{7b})$; $N(R^7)S(O)N(R^{7a}R^{7b})$; $SR^7$; $N(R^7R^{7a})$; $OC(O)R^7$; $N(R^7)C(O)R^7$; $N(R^7)S(O)_2R^{7a}$; $N(R^7)S(O)R^{7a}$; $N(R^7)C(O)N(R^{7a}R^{7b})$; $N(R^7)C(O)OR^{7a}$; $OC(O)N(R^7R^{7a})$; or $C_{1-6}$ alkyl, wherein $C_{1-6}$ alkyl is optionally substituted with one or more $R^8$;

$R^6$ is $T^2$; $C(O)OR^9$; $OR^9$; $C(O)R^9$; $C(O)N(R^9R^{9a})$; $S(O)_2N(R^9R^{9a})$; $S(O)N(R^9R^{9a})$; $S(O)_2R^9$; $S(O)R^9$; $N(R^9)S(O)_2N(R^{9a}R^{9b})$; $N(R^9)S(O)N(R^{9a}R^{9b})$; $SR^9$; $N(R^9R^{9a})$; $OC(O)R^9$; $N(R^9)C(O)R^{9a}$; $N(R^9)S(O)_2R^{9a}$; $N(R^9)S(O)R^{9a}$; $N(R^9)C(O)N(R^{9a}R^{9b})$; $N(R^9)C(O)OR^{9a}$; $OC(O)N(R^9R^{9a})$; or $C_{1-6}$ alkyl substituted with one or more $T^2$ and optionally substituted with one or more $R^8$;

$R^9$, $R^{9a}$, $R^{9b}$ are independently selected from the group consisting of $R^{9c}$; and $R^{9d}$, provided that at least one of $R^9$, $R^{9a}$, $R^{9b}$ is $R^{9c}$;

$R^{9a}$ is $T^2$; or $C_{1-6}$ alkyl, wherein $C_{1-6}$ alkyl is substituted with one or more $T^2$ and optionally substituted with one or more $R^8$;

$R^7$, $R^{7a}$, $R^{7b}$, $R^{9d}$ are independently selected from the group consisting of H; and $C_{1-6}$ alkyl, wherein $C_{1-6}$ alkyl is optionally substituted with one or more $R^8$;

$R^8$ is halogen; CN; $C(O)OR^{10}$; $OR^{10}$; $C(O)R^{10}$; $C(O)N(R^{10}R^{10a})$; $S(O)_2N(R^{10}R^{10a})$; $S(O)N(R^{10}R^{10a})$; $S(O)_2R^{10}$; $S(O)R^{10}$; $N(R^{10})S(O)_2N(R^{10a}R^{10b})$; $N(R^{10})S(O)N(R^{10a}R^{10b})$; $SR^{10}$; $N(R^{10}R^{10a})$; $OC(O)R^{10}$; $N(R^{10})C(O)R^{10a}$; $N(R^{10}S(O)_2R^{10a}$; $N(R^{10})S(O)R^{10a}$; $N(R^{10})C(O)N(R^{10a}R^{10b})$; $N(R^{10})C(O)OR^{10a}$; $OC(O)N(R^{10}R^{10a})$; or $C_{1-6}$ alkyl, wherein $C_{1-6}$ alkyl is optionally substituted with one or more halogen, which are the same or different;

$R^{10}$, $R^{10a}$, $R^{10b}$ are independently selected from the group consisting of H; and $C_{1-6}$ alkyl, wherein $C_{1-6}$ alkyl is optionally substituted with one or more halogen, which are the same or different;

$T^2$ is $C_{3-7}$ cycloalkyl; 4 to 7 membered heterocyclyl; 9 to 11 membered heterobicyclyl; phenyl; naphthyl; indenyl; or indanyl, wherein $T^2$ is optionally substituted with one or more $R^{11}$;

$R^{11}$ is halogen; CN; $C(O)OR^{12}$; $OR^{12}$; oxo (=O), where the ring is at least partially saturated; $C(O)R^{12}$; $C(O)N(R^{12}R^{12a})$; $S(O)_2N(R^{12}R^{12a})$; $S(O)N(R^{12}R^{12a})$; $S(O)_2R^{12}$; $S(O)R^{12}$; $N(R^{12})S(O)_2N(R^{12a}R^{12})$; $N(R^{12})S(O)N(R^{12a}R^{12b})$; $SR^{12}$; $N(R^{12}R^{12a})$; $OC(O)R^{12}$; $N(R^{12})C(O)R^{12a}$; $N(R^{12})S(O)_2R^{12a}$; $N(R^{12})S(O)R^{12a}$; $N(R^{12})C(O)N(R^{12a}R^{12b})$; $N(R^{12})C(O)OR^{12a}$; $OC(O)N(R^{12}R^{12a})$; or $C_{1-6}$ alkyl, wherein $C_{1-6}$ alkyl is optionally substituted with one or more halogen which are the same or different;

$R^{12}$, $R^{12a}$, $R^{12b}$ are independently selected from the group consisting of H; and $C_{1-6}$ alkyl, wherein $C_{1-6}$ alkyl is optionally substituted with one or more halogen, which are the same or different.

In case a variable or substituent can be selected from a group of different variants and such variable or substituent occurs more than once the respective variants can be the same or different.

Within the meaning of the present invention the terms are used as follows:

"Alkyl" means a straight-chain or branched carbon chain that may contain double or triple bonds. It is generally preferred that alkyl doesn't contain double or triple bonds. Thus, the term "alkyl" includes within the meaning of the present invention alkyl groups as well as alkenyl and alkinyl groups. Each hydrogen of an alkyl carbon may be replaced by a substituent.

"$C_{1-4}$ alkyl" means an alkyl chain having 1-4 carbon atoms, e.g. if present at the end of a molecule: methyl, ethyl, —CH=CH$_2$, —C≡CH, n-propyl, isopropyl, —CH=CH—CH$_3$, —CH$_2$—CH=CH$_2$, n-butyl, isobutyl, —CH=CH—CH$_2$—CH$_3$, —CH=CH—CH=CH$_2$, sec-butyl tert-butyl, or e.g. —CH$_2$—, —CH$_2$—CH$_2$—, —CH=CH—, —CH(CH$_3$)—, —C(CH$_2$)—, —CH$_2$—CH$_2$—CH$_2$—, —CH(C$_2$H$_5$)—, —CH(CH$_3$)$_2$—, when two moieties of a molecule are linked by the alkyl group. Preferably, $C_{1-4}$ alkyl includes methyl, ethyl, n-propyl, isopropyl, n-butyl, isobutyl, sec-butyl and tert-butyl. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, —CH=CH$_2$, —C≡CH, n-propyl, isopropyl, —CH=CH—CH$_3$, —CH$_2$—CH=CH$_2$, n-butyl, isobutyl, —CH=CH—CH$_2$—CH$_3$, —CH=CH—CH=CH$_2$, sec-butyl; tert-butyl, n-pentyl, n-hexyl, or e.g. —CH$_2$—, —CH$_2$—CH$_2$—, —CH=CH—, —CH(CH$_3$)—, —C(CH$_2$)—, —CH$_2$—CH$_2$—CH$_2$—, —CH(C$_2$H$_5$)—, —CH(CH$_3$)$_2$—, when two moieties of a molecule are linked by the alkyl group. Preferably, $C_{1-6}$ alkyl includes methyl, ethyl, n-propyl, isopropyl, n-butyl, isobutyl, sec-butyl and tert-butyl, n-pentyl, and n-hexyl. Each hydrogen of a $C_{1-6}$ alkyl carbon may be replaced by a substituent.

"$C_{3-7}$ cycloalkyl" or "$C_{3-7}$ cycloalkyl ring" means a cyclic alkyl chain having 3-7 carbon atoms, e.g. cyclopropyl, cyclobutyl, cyclopentyl, cyclohexyl, cyclohexenyl, cycloheptyl. Each hydrogen of a cycloalkyl carbon may be replaced by a substituent.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydro furan, tetrahydrothiophene, pyrrolidine, imidazolidine, pyrazolidine, oxazolidine, isoxazolidine, thiazolidine, isothiazolidine, thiadiazolidine, sulfo lane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane.

Preferred compounds of formula (I) are those compounds in which one or more of the residues contained therein have the meanings given below, with all combinations of preferred substituent definitions being a subject of the present invention. With respect to all preferred compounds of the formula (I) the present invention also includes all tautomeric and stereoisomeric forms and mixtures thereof in all ratios, and their pharmaceutically acceptable salts. The same applies for preferred compounds of formula (Ia).

In preferred embodiments of the present invention, the substituents mentioned below independently have the following meaning. Hence, one or more of these substituents can have the preferred or more preferred meanings given below.

Preferably, X is $NH_2$, $NC(O)NH_2$ or $NC(S)NH_2$, more preferred X is $NH_2$ or $NC(O)NH_2$; even more preferred X is $NH_2$.

Preferably, $R^1$ and $R^2$ are independently H or $CH_3$. Even more preferred $R^1$ and $R^2$ are H.

Preferably, $R^3$ is H, halogen or $CH_3$. Even more preferred $R^3$ is H or F.

Preferably, $T^1$ is unsubstituted phenyl; substituted phenyl; unsubstituted 4 to 7 membered heterocyclyl; substituted 4 to 7 membered heterocyclyl; unsubstituted 9 to 11 membered heterobicyclyl; or substituted 9 to 11 membered heterobicyclyl.

Preferably, $T^1$ is unsubstituted, substituted with one $R^5$, two $R^5$, one $R^6$, two $R^6$, or one $R^5$ and one $R^6$.

Preferably, $T^1$ is phenyl; pyrrolyl; furyl; thienyl; pyrazolyl; oxazolyl; thiazolyl; pyridyl and N-oxide thereof; pyrimidinyl; indolyl; indolinyl; indazolyl; quinolinyl; isoquinolinyl; benzodioxolyl; dihydrobenzofuryl; dihydrobenzoxazinyl; dihydrobenzodioxinyl; benzodioxanyl; or benzothiazole dioxide. More preferred $T^1$ is phenyl or pyridyl.

Preferably, $R^5$ is oxo (=O), where the ring is at least partially substituted; F; Cl; CN; $N(R^7R^{7a})$; $OR^7$; $C(O)OR^7$; $C(O)N(R^7R^{7a})$; $N(R^7)S(O)_2R^{7a}$; $S(O)_2N(R^7R^{7a})$; $S(O)_2R^7$; $S(O)R^7$; $N(R^7)C(O)R^{7a}$; or $C_{1-6}$ alkyl, which is optionally substituted with one or more $R^8$.

Preferably, $R^7$, $R^{7a}$ are independently selected from the group consisting of H; $CH_3$; $CH_2CH_3$; n-butyl; tert.-butyl; iso-propyl; n-pentyl; isopentyl; neopentyl; 2-ethylbutyl; $CF_3$; $CH_2CH_2OH$; $CH_2CH_2CH_2OH$; $CH_2C(CH_3)_2CH_2OH$; $CH_2CH_2OCH_3$; $CH_2CH_2NH_2$; $CH_2CF_3$; $CH_2CH_2CF_3$; $CH_2CH_2CH_2CF_3$; $C(CH_3)_2CF_3$; $CH_2CH_2NHCH_3$; $CH_2CH_2N(CH_3)_2$; $CH_2CH_2CH_2N(CH_3)_2$; $CH_2C(O)OH$; and $CH_2C(O)N(CH_3)_2$.

Preferably, $R^8$ is F; Cl; Br; OH; $CH_3$; or $CH_2CH_3$.

Preferably, $R^5$ is oxo (=O), where the ring is at least partially substituted; F; Cl; $NH_2$; $NH(CH_3)$; $N(CH_3)_2$; $NH(CH_2)_2OH$; $N((CH_2)_2OH)_2$; OH; $OCH_3$; $OCF_3$; $OCH(CH_3)_2$; $CH_2OH$; $CH_2OCH_3$; $CH_2Br$; $CH_3$; $CH_2CH_3$; $CH(CH_3)_2$; $C(CH_3)_3$; $CF_3$; $C(O)OH$; $C(O)OCH_3$; $C(O)OCH_2CH_3$; $C(O)NH_2$; $C(O)NH(CH_3)$; $C(O)(CH_3)_2$; $C(O)NHCH_2CH_3$; $C(O)N(CH_3)CH_2CH_3$; $C(O)NHCH_2CH_2OH$; $C(O)N(CH_3)CH_2CH_2OH$; $C(O)NHCH_2CH_2OCH_3$; $C(O)N(CH_3)CH_2CH_2OCH_3$; $C(O)NHCH_2CH_2NH_2$; $C(O)N(CH_3)CH_2CH_2NH_2$; $C(O)NHCH_2CH_2NHCH_3$; $C(O)N(CH_3)CH_2CH_2NHCH_3$; $C(O)NHCH_2CH_2N(CH_3)_2$; $C(O)N(CH_3)CH_2CH_2N(CH_3)_2$; $HNC(O)H_3$; $S(O)_2CH_3$; $S(O)CH_3$; $S(O)_2NH_2$; $S(O)_2NHC(CH_3)_3$; $S(O)_2NHCH_2CH(CH_2CH_3)_2$; $S(O)_2NH(CH_2)_2OH$; $S(O)_2NH(CH_2)_2CF_3$; $S(O)_2NH(CH_2)_3CF_3$; $S(O)_2NH(CH_2)_3OH$; $S(O)_2NHCH_2C(CH_3)_2CH_2OH$; $S(O)_2NH(CH_2)_2OCH_3$; or $NHS(O)_2CH_3$.

Preferably, $R^6$ is $S(O)_2N(R^9R^{9a})$; $N(R^9)S(O)_2R^{9a}$; $S(O)_2R^9$; $OR^9$; or $SR^9$.

Preferably, $R^6$ is $S(O)_2N(R^{9c}R^{9d})$; $N(R^{9d})S(O)_2R^{9c}$; $S(O)_2R^{9c}$; or $OR^{9c}$.

Preferably, $R^{9c}$ is $T^2$; $CH_2$-$T^2$; or $C_{1-4}$ alkyl-$T^2$.

Preferably, $R^{9d}$ is H or methyl.

Preferably, $T^2$ is phenyl; naphthyl; $C_{3-4}$ cycloalkyl; or 4 to 7 membered heterocyclyl, wherein $T^2$ is optionally substituted with up to three $R^{11}$.

Preferably, $T^2$ is azetidinyl; imidazolidinyl; pyrrolidinyl; piperidinyl; piperizinyl; isoindolinyl; oxazolyl; dihydroisoquinolinyl; morpholinyl; pyranyl; azepanyl; azetidinyl; thiamorpholine dioxide; cyclopropyl; cyclobutyl; cyclopentyl; cyclohexyl; cycloheptyl; phenyl; or naphthyl.

Preferably, $R^{11}$ is oxo (=O), where the ring is at least partially saturated; F; Cl; $CH_3$; $CH_2CH_3$; $CH_2CH_2CH_3$; $CH(CH_3)_2$; $CF_3$; OH; $OCH_3$; $OCF_3$; $NH_2$; $NHCH_3$; $N(CH_3)_2$.

Preferred compounds are those of formula (Ia)

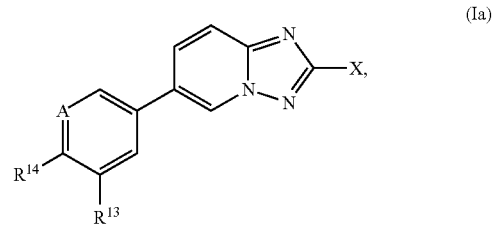

(Ia)

wherein
X has the meaning as indicated above;
A is CH; or N;
$R^{14}$ is H; or $R^5$;
$R^{13}$ is H; $R^5$; or $R^6$.
Preferably, $R^{13}$ is $R^5$ or $R^6$.
Preferably, $R^{14}$ is H; OH; or $OCH_3$.

Compounds of formula (I) in which some or all of the above-mentioned groups have the preferred meanings are also an object of the present invention. the same applies for the preferred compounds of formula (Ia).

Further preferred compounds of the present invention are those which are selected from the group consisting of
3-(2-Amino-[1,2,4]triazolo[1,5-a]pyridin-6-yl)-N-(2-hydroxy-ethyl)-benzenesulfonamide;
6-(5-Methanesulfonyl-pyridin-3-yl)-[1,2,4]triazolo[1,5-a]pyridin-2-ylamine;
5-(2-Amino-[1,2,4]triazolo[1,5-a]pyridin-6-yl)-pyridine-3-sulfonic acid butylamide;
5-(2-Amino-[1,2,4]triazolo[1,5-a]pyridin-6-yl)-2-methoxy-phenol;
1-(6-(3,4-dimethoxyphenyl)-[1,2,4]triazolo[1,5-a]pyridin-2-yl)urea;
5-(2-Amino-[1,2,4]triazolo[1,5-a]pyridin-6-yl)-pyridine-3-sulfonic acid tert-butylamide;
5-(2-Amino-[1,2,4]triazolo[1,5-a]pyridin-6-yl)-pyridine-3-sulfonic acid benzylamide;
5-(2-Amino-[1,2,4]triazolo[1,5-a]pyridin-6-yl)-pyridine-3-sulfonic acid (2-ethyl-butyl)-amide;
5-(2-Amino-[1,2,4]triazolo[1,5-a]pyridin-6-yl)-pyridine-3-sulfonic acid (4-chloro-phenyl)-amide;
5-(2-Amino-[1,2,4]triazolo[1,5-a]pyridin-6-yl)-pyridine-3-sulfonic acid (3,5-bis-trifluoromethyl-phenyl)-amide;
5-(2-Amino-[1,2,4]triazolo[1,5-a]pyridin-6-yl)-pyridine-3-sulfonic acid (4-fluoro-phenyl)-amide;

6-(3-Methanesulfonyl-phenyl)-[1,2,4]triazolo[1,5-a]pyridin-2-ylamine;

6-(3,4-dimethoxyphenyl)-[1,2,4]triazolo[1,5-a]pyridin-2-amine;

3-(2-amino-[1,2,4]triazolo[1,5-a]pyridin-6-yl)-N-(2-aminoethyl)benzenesulfonamide;

6-(3-isopropoxy-4-methoxyphenyl)-[1,2,4]triazolo[1,5-a]pyridin-2-amine;

4-(2-Amino-[1,2,4]triazolo[1,5-a]pyridin-6-yl)-2-methoxyphenol;

3-(2-Amino-[1,2,4]triazolo[1,5-a]pyridin-6-yl)-N-butylbenzenesulfonamide;

4,4,4-Trifluorobutane-1-sulfonic acid [5-(2-amino-[1,2,4]triazolo[1,5-a]pyridin-6-yl)-pyridin-3-yl]amide;

N-[5-(2-Amino-[1,2,4]triazolo[1,5-a]pyridin-6-yl)-pyridin-3-yl]-3-trifluoromethylbenzenesulfonamide HCl salt;

N-[5-(2-Amino-[1,2,4]triazolo[1,5-a]pyridin-6-yl)-pyridin-3-yl]-2-trifluoromethylbenzenesulfonamide HCl salt;

N-[5-(2-Amino-[1,2,4]triazolo[1,5-a]pyridin-6-yl)-pyridin-3-yl]-4-trifluoromethylbenzenesulfonamide HCl salt;

Naphthalene-2-sulfonic acid [5-(2-amino-[1,2,4]triazolo[1,5-a]pyridin-6-yl)-pyridin-3-yl]-amide HCl salt;

N-[5-(2-Amino-[1,2,4]triazolo[1,5-a]pyridin-6-yl)-pyridin-3-yl]-4-isopropylbenzenesulfonamide HCl salt;

Naphthalene-1-sulfonic acid [5-(2-amino-[1,2,4]triazolo[1,5-a]pyridin-6-yl)-pyridin-3-yl]-amide HCl salt;

N-[5-(2-Amino-[1,2,4]triazolo[1,5-a]pyridin-6-yl)-pyridin-3-yl]-4-chlorobenzenesulfonamide HCl salt;

6-(3,4-Dimethoxyphenyl)-8-chloro-[1,2,4]triazolo[1,5-a]pyridine-2-ylamine;

N-[5-(2-Amino-[1,2,4]triazolo[1,5-a]pyridin-6-yl)pyridine-3-yl]-3-trifluoromethoxybenzenesulfonamide HCl;

N-[5-(2-Amino-[1,2,4]triazolo[1,5-a]pyridin-6-yl)pyridine-3-yl]-C-(2-trifluoromethylphenyl)methanesulfonamide HCl;

N-[5-(2-Amino-[1,2,4]triazolo[1,5-a]pyridin-6-yl)pyridine-3-yl]-C-(4-trifluoromethylphenyl)methanesulfonamide HCl;

N-[5-(2-Amino-[1,2,4]triazolo[1,5-a]pyridin-6-yl)pyridine-3-yl]-C-(4-chlorophenyl)methanesulfonamide HCl;

N-[5-(2-Amino-[1,2,4]triazolo[1,5-a]pyridin-6-yl)-pyridin-3-yl]-3,5-bis-trifluoromethylbenzenesulfonamide;

5-(2-amino-[1,2,4]triazolo[1,5-a]pyridin-6-yl)-N-(4-(trifluoromethyl)phenyl)pyridine-3-sulfonamide;

5-(2-amino-[1,2,4]triazolo[1,5-a]pyridin-6-yl)-N-(2-(trifluoromethyl)phenyl)pyridine-3-sulfonamide;

5-(2-amino-[1,2,4]triazolo[1,5-a]pyridin-6-yl)-N-(3-(trifluoromethyl)phenyl)pyridine-3-sulfonamide;

5-(2-amino-[1,2,4]triazolo[1,5-a]pyridin-6-yl)-N-methyl-N-(3-(trifluoromethyl)phenyl)pyridine-3-sulfonamide;

5-(2-amino-[1,2,4]triazolo[1,5-a]pyridin-6-yl)-N-(4-(trifluoromethoxy)phenyl)pyridine-3-sulfonamide;

5-(2-amino-[1,2,4]triazolo[1,5-a]pyridin-6-yl)-N-phenylpyridine-3-sulfonamide;

5-(2-amino-[1,2,4]triazolo[1,5-a]pyridin-6-yl)-N-(3-(trifluoromethoxy)phenyl)pyridine-3-sulfonamide;

5-(2-amino-[1,2,4]triazolo[1,5-a]pyridin-6-yl)-N-(3-(1,1,2,2-tetrafluoroethoxy)phenyl)pyridine-3-sulfonamide;

5-(2-amino-[1,2,4]triazolo[1,5-a]pyridin-6-yl)-N-(3-(difluoromethoxy)phenyl)pyridine-3-sulfonamide;

5-(2-amino-[1,2,4]triazolo[1,5-a]pyridin-6-yl)-N-(4-(difluoromethoxy)phenyl)pyridine-3-sulfonamide;

6-(5-(trifluoromethyl)pyridin-3-yl)-[1,2,4]triazolo[1,5-a]pyridin-2-amine;

6-(4-isopropoxy-3-methoxyphenyl)-[1,2,4]triazolo[1,5-a]pyridin-2-amine;

5-(2-amino-[1,2,4]triazolo[1,5-a]pyridine-6-yl)-N-(2-methyl-1-(pyrrolidin-1-yl)propan-2-yl)pyridine-3-sulfonamide;

6-(5-(4-fluoropiperidin-1-ylsulfonyl)pyridine-3-yl)-[1,2,4]triazolo[1,5-a]pyridine-2-amine;

6-(5-(4-methylpiperizin-1-ylsulfonyl)pyridine-3-yl)-[1,2,4]triazolo[1,5-a]pyridine-2-amine;

2-(5-(2-amino-[1,2,4]triazolo[1,5-a]pyridine-6-yl)pyridine-3-sulfoamido)-N,N-dimethylacetamide;

5-(2-amino-[1,2,4]triazolo[1,5-a]pyridine-6-yl)-N-(2-(oxoimidazolidin-1-yl)ethyl)pyridine-3-sulfonamide;

5-(2-amino-[1,2,4]triazolo[1,5-a]pyridine-6-yl)-N-(2-(dimethylamino)ethyl)-N-methylpyridine-3-sulfonamide;

5-(2-amino-[1,2,4]triazolo[1,5-a]pyridine-6-yl)-N-(3-(dimethylamino)propyl)pyridine-3-sulfonamide;

5-(2-amino-[1,2,4]triazolo[1,5-a]pyridine-6-yl)-N-butyl-N-methylpyridine-3-sulfonamide;

5-(2-amino-[1,2,4]triazolo[1,5-a]pyridine-6-yl)-N-isopentylpyridine-3-sulfonamide;

5-(2-amino-[1,2,4]triazolo[1,5-a]pyridine-6-yl)-N-(cyclopropylmethyl)pyridine-3-sulfonamide;

6-(5-isoindolin-2-ylsulfonyl)pyridine-3-yl)-[1,2,4]triazolo[1,5-a]pyridine-2-amine;

6-(5-piperazin-1-ylsulfonyl)pyridine-3-yl)-[1,2,4]triazolo[1,5-a]pyridine-2-amine;

5-(2-amino-[1,2,4]triazolo[1,5-a]pyridine-6-yl)-N-benzyl-N-methylpyridine-3-sulfonamide;

5-(2-amino-[1,2,4]triazolo[1,5-a]pyridine-6-yl)-N-((2,4-dimethyloxazol-5-yl)methyl)pyridine-3-sulfonamide;

5-(2-amino-[1,2,4]triazolo[1,5-a]pyridine-6-yl)-N-benzyl-N-butylpyridine-3-sulfonamide;

6-(5-(3,4-dihydroisoquinolin-2(1H)-ylsulfonyl)pyridine-3-yl-[1,2,4]triazolo[1,5-a]pyridin-amine;

5-(2-amino-[1,2,4]triazolo[1,5-a]pyridine-6-yl)-N-(2,3-dichlorobenzyl)-N-methylpyridine-3-sulfonamide;

5-(2-amino-[1,2,4]triazolo[1,5-a]pyridine-6-yl)-N-cyclopropyl-N-(2-fluorobenzyl)pyridine-3-sulfonamide;

5-(2-amino-[1,2,4]triazolo[1,5-a]pyridine-6-yl)-N-(2-phenylpropan-2-yl)pyridine-3-sulfonamide;

5-(2-amino-[1,2,4]triazolo[1,5-a]pyridine-6-yl)-N-(2-(4-fluorophenyl)propan-2-yl)pyridine-3-sulfonamide;

5-(2-amino-[1,2,4]triazolo[1,5-a]pyridine-6-yl)-N-(4-fluorobenzyl)pyridine-3-sulfonamide;

5-(2-amino-[1,2,4]triazolo[1,5-a]pyridine-6-yl)-N,N-diethylpyridine-3-sulfonamide;

5-(2-amino-[1,2,4]triazolo[1,5-a]pyridine-6-yl)-N-(1,1,1-trifluoro-2-methylpropan-2-yl)pyridine-3-sulfonamide;

5-(2-amino-[1,2,4]triazolo[1,5-a]pyridine-6-yl)pyridine-3-sulfonamide;

5-(2-amino-[1,2,4]triazolo[1,5-a]pyridine-6-yl)-N-butylpyridine-3-sulfonamide;

6-(5-(morpholinosulfonyl)pyridin-3-yl)-[1,2,4]triazolo[1,5-a]pyridin-2-amine;

5-(2-amino-[1,2,4]triazolo[1,5-a]pyridine-6-yl)-N-(3,3,3-trifluoropropyl)pyridine-3-sulfonamide;

5-(2-amino-[1,2,4]triazolo[1,5-a]pyridine-6-yl)-N,N-dimethylpyridine-3-sulfonamide;

5-(2-amino-[1,2,4]triazolo[1,5-a]pyridine-6-yl)-N-neopentylpyridine-3-sulfonamide;

5-(2-amino-[1,2,4]triazolo[1,5-a]pyridine-6-yl)-N-cyclopentylpyridine-3-sulfonamide;

5-(2-amino-[1,2,4]triazolo[1,5-a]pyridine-6-yl)-N-(3,4-dichlorobenzyl)pyridine-3-sulfonamide;

3-(2-amino-[1,2,4]triazolo[1,5-a]pyridine-6-yl)-N-(2-(dimethylamino)ethyl)benzenesulfonamide;

3-(2-amino-[1,2,4]triazolo[1,5-a]pyridine-6-yl)-N-(2-(dimethylamino)ethyl)-N-methylbenzenesulfonamide;

3-(2-amino-[1,2,4]triazolo[1,5-a]pyridin-6-yl)-N-tert-butylbenzenesulfonamide;
2-(3-(2-amino-[1,2,4]triazolo[1,5-a]pyridin-6-yl)phenylsulfonamido)acetic acid;
3-(2-amino-[1,2,4]triazolo[1,5-a]pyridin-6-yl)-N-(3-(dimethylamino)propyl)benzenesulfonamide;
6-(5-chloropyridin-3-yl)-[1,2,4]triazolo[1,5-a]pyridin-2-amine;
5-(2-amino-[1,2,4]triazolo[1,5-a]pyridin-6-yl)-N-cyclopropylpyridine-3-sulfonamide;
6-(5-(pyrrolidin-1-ylsulfonyl)pyridin-3-yl)-[1,2,4]triazolo[1,5-a]pyridin-2-amine;
5-(2-amino-[1,2,4]triazolo[1,5-a]pyridin-6-yl)-N-tert-butyl-N-methylpyridine-3-sulfonamide;
6-(5-(piperidin-1-ylsulfonyl)pyridin-3-yl)-[1,2,4]triazolo[1,5-a]pyridin-2-amine;
5-(2-amino-[1,2,4]triazolo[1,5-a]pyridin-6-yl)-N-isobutylpyridine-3-sulfonamide;
5-(2-amino-[1,2,4]triazolo[1,5-a]pyridin-6-yl)-N-isopropylpyridine-3-sulfonamide;
5-(2-amino-[1,2,4]triazolo[1,5-a]pyridin-6-yl)-N-(2,3-dichlorobenzyl)pyridine-3-sulfonamide;
5-(2-amino-[1,2,4]triazolo[1,5-a]pyridin-6-yl)-N-propylpyridine-3-sulfonamide;
5-(2-amino-[1,2,4]triazolo[1,5-a]pyridin-6-yl)-N-(2,2,2-trifluoroethyl)pyridine-3-sulfonamide;
5-(2-amino-[1,2,4]triazolo[1,5-a]pyridin-6-yl)-N-cyclohexylpyridine-3-sulfonamide;
5-(2-amino-[1,2,4]triazolo[1,5-a]pyridin-6-yl)-N-(tetrahydro-2H-pyran-4-yl)pyridine-3-sulfonamide;
5-(2-amino-[1,2,4]triazolo[1,5-a]pyridin-6-yl)-N-((tetrahydro-2H-pyran-4-yl)methyl)pyridine-3-sulfonamide;
5-(2-amino-[1,2,4]triazolo[1,5-a]pyridin-6-yl)-N-(4-hydroxycyclohexyl)pyridine-3-sulfonamide;
6-(5-(4,4-difluoropiperidin-1-ylsulfonyl)pyridin-3-yl)-[1,2,4]triazolo[1,5-a]pyridin-2-amine;
6-(5-(azepan-1-ylsulfonyl)pyridin-3-yl)-[1,2,4]triazolo[1,5-a]pyridin-2-amine;
6-(5-(azetidin-1-ylsulfonyl)pyridin-3-yl)-[1,2,4]triazolo[1,5-a]pyridin-2-amine;
5-(2-amino-[1,2,4]triazolo[1,5-a]pyridin-6-yl)-N-(cyclobutylmethyl)pyridine-3-sulfonamide;
5-(2-amino-[1,2,4]triazolo[1,5-a]pyridin-6-yl)-N-ethylpyridine-3-sulfonamide;
5-(2-amino-[1,2,4]triazolo[1,5-a]pyridin-6-yl)-N-methylpyridine-3-sulfonamide;
6-(3,4-dimethoxyphenyl)-8-fluoro-[1,2,4]triazolo[1,5-a]pyridin-2-amine;
6-(3,4-dimethoxyphenyl)-8-methyl-[1,2,4]triazolo[1,5-a]pyridin-2-amine;
6-(5-(benzylsulfonyl)pyridin-3-yl)-[1,2,4]triazolo[1,5-a]pyridin-2-amine;
6-(5-(tert-Butylsulfonyl)pyridin-3-yl)-[1,2,4]triazolo[1,5-a]pyridin-2-amine;
5-(2-amino-[1,2,4]triazolo[1,5-a]pyridin-6-yl)-N-ethyl-N-methylpyridine-3-sulfonamide;
5-(2-amino-8-fluoro-[1,2,4]triazolo[1,5-a]pyridin-6-yl)-N-tert-butylpyridine-3-sulfonamide;
6-(5-isobutoxypyridin-3-yl)-[1,2,4]triazolo[1,5-a]pyridin-2-amine;
6-(5-(benzyloxy)pyridin-3-yl)-[1,2,4]triazolo[1,5-a]pyridin-2-amine;
6-(5-phenoxypyridin-3-yl)-[1,2,4]triazolo[1,5-a]pyridin-2-amine;
6-(5-(neopentyloxy)pyridin-3-yl)-[1,2,4]triazolo[1,5-a]pyridin-2-amine;
6-(5-(neopentylsulfonyl)pyridin-3-yl)-[1,2,4]triazolo[1,5-a]pyridin-2-amine;
5-(2-amino-[1,2,4]triazolo[1,5-a]pyridin-6-yl)-N-(cyclopentylmethyl)pyridine-3-sulfonamide;
5-(2-amino-[1,2,4]triazolo[1,5-a]pyridin-6-yl)-N-(cycloheptylmethyl)pyridine-3-sulfonamide;
5-(2-amino-[1,2,4]triazolo[1,5-a]pyridin-6-yl)-N-(3-isopropylphenyl)pyridine-3-sulfonamide;
5-(2-amino-[1,2,4]triazolo[1,5-a]pyridin-6-yl)-N-(2-fluorophenyl)pyridine-3-sulfonamide;
5-(2-amino-[1,2,4]triazolo[1,5-a]pyridin-6-yl)-N-(4-isopropylphenyl)pyridine-3-sulfonamide;
5-(2-amino-[1,2,4]triazolo[1,5-a]pyridin-6-yl)-N-(2-methoxyphenyl)pyridine-3-sulfonamide;
5-(2-amino-[1,2,4]triazolo[1,5-a]pyridin-6-yl)-N-(2,4-difluorophenyl)pyridine-3-sulfonamide;
5-(2-amino-[1,2,4]triazolo[1,5-a]pyridin-6-yl)-N-tert-butylnicotinamide;
5-(2-amino-[1,2,4]triazolo[1,5-a]pyridin-6-yl)-N-(4-methoxyphenyl)pyridine-3-sulfonamide;
5-(2-amino-[1,2,4]triazolo[1,5-a]pyridin-6-yl)-N-(3-fluorophenyl)pyridine-3-sulfonamide;
5-(2-amino-[1,2,4]triazolo[1,5-a]pyridin-6-yl)-N-(3,4-difluorophenyl)pyridine-3-sulfonamide;
5-(2-amino-[1,2,4]triazolo[1,5-a]pyridin-6-yl)-N-(2-isopropylphenyl)pyridine-3-sulfonamide;
5-(2-amino-[1,2,4]triazolo[1,5-a]pyridin-6-yl)-N-(3,5-difluorophenyl)pyridine-3-sulfonamide;
5-(2-amino-[1,2,4]triazolo[1,5-a]pyridin-6-yl)-N-(3-methoxyphenyl)pyridine-3-sulfonamide;
5-(2-amino-[1,2,4]triazolo[1,5-a]pyridin-6-yl)-N-(2,3-difluorophenyl)pyridine-3-sulfonamide;
5-(2-amino-[1,2,4]triazolo[1,5-a]pyridin-6-yl)-N-(1-methylcyclobutyl)pyridine-3-sulfonamide;
5-(2-amino-[1,2,4]triazolo[1,5-a]pyridin-6-yl)-N-(2-aminoethyl)pyridine-3-sulfonamide;
5-(2-amino-8-fluoro-[1,2,4]triazolo[1,5-a]pyridin-6-yl)-N-methylpyridine-3-sulfonamide;
5-(2-amino-8-fluoro-[1,2,4]triazolo[1,5-a]pyridin-6-yl)-N-isopropylpyridine-3-sulfonamide;
5-(2-amino-8-fluoro-[1,2,4]triazolo[1,5-a]pyridin-6-yl)-N-propylpyridine-3-sulfonamide;
6-(5-(azetidin-1-ylsulfonyl)pyridin-3-yl)-8-fluoro-[1,2,4]triazolo[1,5-a]pyridin-2-amine;
5-(2-amino-8-fluoro-[1,2,4]triazolo[1,5-a]pyridin-6-yl)-N-(2,2,2-trifluoroethyl)pyridine-3-sulfonamide;
5-(2-amino-8-fluoro-[1,2,4]triazolo[1,5-a]pyridin-6-yl)-N-ethyl-N-methylpyridine-3-sulfonamide;
8-fluoro-6-(3-(methylsulfonyl)phenyl)-[1,2,4]triazolo[1,5-a]pyridin-2-amine;
6-(6-amino-5-(trifluoromethyl)pyridin-3-yl)-[1,2,4]triazolo[1,5-a]pyridin-2-amine;
5-(3-(2-amino-[1,2,4]triazolo[1,5-a]pyridin-6-yl)phenylsulfonamido)pentanoic acid;
4-(3-(2-amino-[1,2,4]triazolo[1,5-a]pyridin-6-yl)phenylsulfonamido)butanoic acid;
6-(5-(benzylthio)pyridin-3-yl)-[1,2,4]triazolo[1,5-a]pyridin-2-amine;
8-fluoro-6-(5-(trifluoromethyl)pyridin-3-yl)-[1,2,4]triazolo[1,5-a]pyridin-2-amine;
6-(4-fluorophenyl)-[1,2,4]triazolo[1,5-a]pyridin-2-amine hydrochloride;
6-(3-methoxyphenyl)-[1,2,4]triazolo[1,5-a]pyridin-2-amine hydrochloride;
6-(3,4,5-trimethoxyphenyl)-[1,2,4]triazolo[1,5-a]pyridin-2-amine hydrochloride;
6-m-tolyl-[1,2,4]triazolo[1,5-a]pyridin-2-amine;

3-(2-amino-[1,2,4]triazolo[1,5-a]pyridin-6-yl)benzonitrile;
6-(3-chlorophenyl)-[1,2,4]triazolo[1,5-a]pyridin-2-amine;
6-phenyl-[1,2,4]triazolo[1,5-a]pyridin-2-amine;
6-(2-methoxyphenyl)-[1,2,4]triazolo[1,5-a]pyridin-2-amine;
6-(3-(ethylamino)phenyl)-[1,2,4]triazolo[1,5-a]pyridin-2-amine;
4-(2-amino-[1,2,4]triazolo[1,5-a]pyridin-6-yl)benzamide;
6-(pyrimidin-5-yl)-[1,2,4]triazolo[1,5-a]pyridin-2-amine hydrochloride;
6-(1-methyl-1H-pyrazol-4-yl)-[1,2,4]triazolo[1,5-a]pyridin-2-amine hydrochloride;
3-(2-amino-[1,2,4]triazolo[1,5-a]pyridin-6-yl)phenol;
6-(3-(trifluoromethyl)phenyl)-[1,2,4]triazolo[1,5-a]pyridin-2-amine hydrochloride;
6-(benzo[d][1,3]dioxol-5-yl)-[1,2,4]triazolo[1,5-a]pyridin-2-amine hydrochloride;
6-(3,4-dimethoxyphenyl)-7-methyl-[1,2,4]triazolo[1,5-a]pyridin-2-amine hydrochloride;
6-(3,4-difluorophenyl)-[1,2,4]triazolo[1,5-a]pyridin-2-amine hydrochloride;
6-(3-fluorophenyl)-[1,2,4]triazolo[1,5-a]pyridin-2-amine hydrochloride;
6-(4-methoxyphenyl)-[1,2,4]triazolo[1,5-a]pyridin-2-amine;
N-(3-(2-amino-[1,2,4]triazolo[1,5-a]pyridin-6-yl)phenyl)acetamide;
6-(2,3-dihydrobenzo[b][1,4]dioxin-6-yl)-[1,2,4]triazolo[1,5-a]pyridin-2-amine;
3-(2-amino-[1,2,4]triazolo[1,5-a]pyridin-6-yl)benzenesulfonamide;
4-(2-amino-[1,2,4]triazolo[1,5-a]pyridin-6-yl)benzenesulfonamide;
3-(2-amino-[1,2,4]triazolo[1,5-a]pyridin-6-yl)benzoic acid;
6-(pyridin-4-yl)-[1,2,4]triazolo[1,5-a]pyridin-2-amine;
6-(1H-pyrazol-3-yl)-[1,2,4]triazolo[1,5-a]pyridin-2-amine;
6-(thiophen-2-yl)-[1,2,4]triazolo[1,5-a]pyridin-2-amine; and
6-(1H-pyrazol-4-yl)-[1,2,4]triazolo[1,5-a]pyridin-2-amine.

Prodrugs of the compounds of the present invention are also within the scope of the present invention.

"Prodrug" means a derivative that is converted into a compound according to the present invention by a reaction with an enzyme, gastric acid or the like under a physiological condition in the living body, e.g. by oxidation, reduction, hydrolysis or the like, each of which is carried out enzymatically. Examples of a prodrug are compounds, wherein the amino group in a compound of the present invention is acylated, alkylated or phosphorylated to form, e.g., eicosanoylamino, alanylamino, pivaloyloxymethylamino or wherein the hydroxyl group is acylated, alkylated, phosphorylated or converted into the borate, e.g. acetyloxy, palmitoyloxy, pivaloyloxy, succinyloxy, fumaryloxy, alanyloxy or wherein the carboxyl group is esterified or amidated. These compounds can be produced from compounds of the present invention according to well-known methods.

Metabolites of compounds of formula (I) are also within the scope of the present invention.

The term "metabolites" refers to all molecules derived from any of the compounds according to the present invention in a cell or organism, preferably mammal.

Preferably the term relates to molecules which differ from any molecule which is present in any such cell or organism under physiological conditions The structure of the metabolites of the compounds according to the present invention will be obvious to any person skilled in the art, using the various appropriate methods.

Where tautomerism, like e.g. keto-enol tautomerism, of compounds of general formula (I) may occur, the individual forms, like e.g. the keto and enol form, are comprised separately and together as mixtures in any ratio. Same applies for stereoisomers, like e.g. enantiomers, cis/trans isomers, conformers and the like.

If desired, isomers can be separated by methods well known in the art, e.g. by liquid chromatography. Same applies for enantiomers by using e.g. chiral stationary phases. Additionally, enantiomers may be isolated by converting them into diastereomers, i.e. coupling with an enantiomerically pure auxiliary compound, subsequent separation of the resulting diastereomers and cleavage of the auxiliary residue. Alternatively, any enantiomer of a compound of formula (I) may be obtained from stereoselective synthesis using optically pure starting materials.

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I) which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I) which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods which are known to the person skilled in the art like, for example by contacting these with an organic or inorganic acid or base in a solvent or dispersant, or by anion exchange or cation exchange with other salts. The present invention also includes all salts of the compounds of the formula (I) which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMEA (Europe) and/or the FDA (US) and/or any other national regulatory agency for use in animals, preferably in humans.

The present invention furthermore includes all solvates of the compounds according to the invention.

The present invention provides compounds of formula (I) as kinase inhibitors, especially as PI3K inhibitors. The compounds of formula (I) may inhibit one or both of these kinases, optionally in addition to other kinases mentioned above without being limited by theory.

Accordingly, the compounds of the present invention are useful for the prevention or treatment of immunological disorders (e.g. immune or autoimmune diseases), inflammatory disorders or allergic disorders.

Thus, another object of the present invention is a compound of the present invention or a pharmaceutically acceptable salt thereof for use as a medicament.

Another object of the present invention is a compound or a pharmaceutically acceptable salt thereof according to the present invention for use in a method of treating or preventing diseases and disorders associated with PI3K.

Yet another object of the present invention is the use of a compound of the present invention or a pharmaceutically acceptable salt thereof for the manufacture of a medicament for the treatment or prophylaxis of diseases and disorders associated with PI3K, preferably PI3Kγ.

According to the present invention "PI3K" or "PI3 kinase" includes all members of the PI3K family comprising class IA (e.g. PI3K alpha, beta and delta), class IB (e.g. PI3K gamma), class II (e.g. PI3KC2 alpha, beta and gamma) and class III (e.g. Vps34 yeast homologue).

"PI3Kγ" means PI3Kγ protein, the only member of PI3K class IB (also referred to as p110-gamma). A human cDNA encoding the PI3Kγ protein of a 1050 amino acid residue long polypeptide was described (Stoyanow et al., 1995, Science 269:690-693). The human PI3Kγ protein is encoded by the PI3KCG gene which comprises 10 exons and is located on chromosome 7q22 (Kratz et al., 2002, Blood 99:372-374).

"PI3Kδ" means PI3Kδ protein, a member of PI3K class class IA (also referred to as p110-delta). A human cDNA encoding the PI3Kδ protein of 1044 amino acids was reported (Vanhaesebroeck et al., 1997, Proc. Natl. Acad. Sci. 94:4330-4335). The human PI3Kδ protein is encoded by the PI3KCD gene which was mapped to chromosome 1p3.2 (Seki et al., 1997, DNA Research 4:355-358).

Yet another object of the present invention is the use of a compound of the present invention or a pharmaceutically acceptable salt thereof for the manufacture of a medicament for the treatment or prophylaxis of immunological, inflammatory, autoimmune, or allergic disorders.

More specifically, preferred disorders are autoimmune diseases; organ and bone marrow transplant rejection; graft-versus-host disease; acute or chronic inflammation; pancreatitis; contact dermatitis; psoriasis; rheumatoid arthritis; multiple sclerosis; type I diabetes; inflammatory bowel disease; Crohn's disease; ulcerative colitis; systemic lupus erythematosus; asthma; chronic obstructive pulmonary disease (COPD); acute respiratory distress syndrome (ARDS); bronchitis; conjunctivitis; dermatitis; allergic rhinitis; acute gouty inflammation; cystic fibrosis; familial Mediterranean fever; tissue damage after bacterial infection; Sweet's syndrome; or anaphylaxis.

Quite more preferred are rheumatoid arthritis (RA), inflammatory bowel disease (IBD), systemic lupus erythematosus (SLE), psoriasis, multiple sclerosis (MS), asthma and chronic obstructive pulmonary disease (COPD).

Rheumatoid arthritis (RA) is a chronic progressive, debilitating inflammatory disease that affects approximately 1% of the world's population. RA is a symmetric polyarticular arthritis that primarily affects the small joints of the hands and feet. In addition to inflammation in the synovium, the joint lining, the aggressive front of tissue called pannus invades and destroys local articular structures (Firestein 2003, Nature 423:356-361).

Inflammatory bowel disease (IBD) is characterized by a chronic relapsing intestinal inflammation. IBD is subdivided into Crohn's disease and ulcerative colitis phenotypes. Crohn's disease involves most frequently the terminal ileum and colon, is transmural and discontinuous. In contrast, in ulcerative colitis, the inflammation is continuous and limited to rectal and colonic mucosal layers. In approximately 10% of cases confined to the rectum and colon, definitive classification of Crohn disease or ulcerative colitis cannot be made and are designated 'indeterminate colitis.' Both diseases include extraintestinal inflammation of the skin, eyes, or joints. Neutrophil-induced injuries may be prevented by the use of neutrophils migration inhibitors (Asakura et al., 2007, World J. Gastroenterol. 13(15):2145-9).

Systemic lupus erythematosus (SLE) is a chronic inflammatory disease generated by T cell-mediated B-cell activation, which results in glomerulonephritis and renal failure. Human SLE is characterized at early stages by the expansion of long-lasting autoreactive $CD4^+$ memory cells (D'Cruz et al., 2007, Lancet 369(9561):587-596).

Psoriasis is a chronic inflammatory dermatosis that affects approximately 2% of the population. It is characterized by red, scaly skin patches that are usually found on the scalp, elbows, and knees, and may be associated with severe arthritis. The lesions are caused by abnormal keratinocyte proliferation and infiltration of inflammatory cells into the dermis and epidermis (Schön et al., 2005, New Engl. J. Med. 352: 1899-1912).

Multiple sclerosis (MS) is an inflammatory and demyelating neurological disease. It has been considered as an autoimmune disorder mediated by CD4+ type 1 T helper cells, but recent studies indicated a role of other immune cells (Hemmer et al., 2002, Nat. Rev. Neuroscience 3, 291-301).

Asthma is a complex syndrome with many clinical phenotypes in both adults and children. Its major characteristics include a variable degree of air flow obstruction, bronchial hyperresponsiveness, and airway inflammation (Busse and Lemanske, 2001, N. Engl. J. Med. 344:350-362).

Chronic obstructive pulmonary disease (COPD) is characterized by inflammation, airflow limitation that is not fully reversible, and a gradual loss of lung function. In COPD, chronic inhalation of irritants causes an abnormal inflammatory response, remodeling of the airways, and restriction of airflow in the lungs. The inhaled irritant is usually tobacco smoke, but occupational dust and environmental pollution are variably implicated (Shapiro 2005, N. Engl. J. Med. 352, 2016-2019).

Pancreatitis is the inflammation of the pancreas. Acute pancreatitis is a condition that develops when the pancreas is damaged by inflammation that leads to swelling and sometimes to necrosis of part of the pancreas (Carroll et al., 2007. American Family Physiscian 75(1): 1513-1520). In chronic pancreatitis widespread injury to the pancreas over many years may cause extensive scarring and destruction of the pancreas. It was demonstrated that PI3Kγ plays a role in a mouse model for pancreatitis. The lethality of the choline-deficient/ethionine-supplemented diet-induced pancreatitis was significantly reduced in mice lacking PI3Kγ (Lupia et al., 2004. Am. J. Pathol. 165(6):2003-2011).

Acute gouty inflammation is the consequence of the deposition of monosodium urate crystals in joints. Neutrophils appear to be the major effector of acute gout, accumulating in the joint fluid where they actively ingest urate crystals, aggregate and degranulate. Acute gouty inflammation as well as other diseases associated with crystal deposition like articular chondrocalcinosis, silicosis, soft tissue calcium deposit in patients with chronic renal failure, may be prevented by inhibition of neutrophils chemotaxis (Ryckman et al., 2003, Arthritis & Rheumatism 48 (8): 2310-20).

Cystic fibrosis (CF) is a hereditary disorder caused by mutations of the cystic fibrosis transmembrane conductance regulator (CFTR), the product of which is a membrane protein thought to function as a chloride channel. The lethal clinical manifestations are clearly related to the thick, infected mucous and chronic neutrophils-dominated airway inflammation. An anti-inflammatory agent with direct effects on neutrophils may represent a good drug candidate for the clinical management of CF (McIntosh et al., 1992, FASEB J 6:2775-82).

Familial Mediterranean Fever (FMF) is an autosomal recessive disorder characterised by recurrent and reversible attacks of fever and serositis. The inflammatory episodes are characterized by massive influx of neutrophils into the serosal and synovial membranes. Secondary amyloidosis, a consequence of long-standing inflammation, is the most sever complication of the disease Inhibitors of neutrophils activation may result beneficial for the amelioration of the disease (Molad Y et al., 2004, J. Investig. Med. 52(1):58-61).

Tissue damage after acute bacterial infection may partly result from excessive neutrophils infiltration and activation in the infected tissue. During pyelonephritis, bacteria in the kidney parenchyma trigger a burst of neutrophils extravascular migration. Experiments in animal models have shown that renal scarring after acute bacterial pyelonephritis results from parenchymal damage by neutrophils. Tissue damages following infections in pyelonephritis, osteomyelitis, endocaditis, endotoxic shock and acute respiratory distress syndrome, may be prevented by inhibition of neutrophils activation (Bille et al., 1982, J. Infect. Dis. 146:220-6).

Sweet's syndrome (named acute febrile neutrophilic dermatosis) is characterized by a constellation of clinical symptoms which include pyrexia, elevated neutrophil count, tender erythematous skin lesions and a diffuse infiltrate consisting predominantly of mature neutrophils typically located in the upper dermis. Inhibition of neutrophils activation may represent a therapy for patient suffering from Sweet's syndrome (Cohen et al., 2007, Orphanet J. Rare Dis. 2:34).

Anaphylaxis is an acute systemic and severe type I hypersensitivity allergic reaction. Anaphylactic shock is the most severe type of anaphylaxis. Anaphylactic shock is a sudden, life-threatening allergic reaction associated with severe hypotension. Platelet-activating factor (PAF) is implicated in the cardiovascular dysfunctions occurring in various shock syndromes, including anaphylaxis. Excessive production of the vasodilator NO causes inflammatory hypotension and shock. Research shows a central role for eNOS, the endothelial isoform of nitric oxide synthase, as a mediator of anaphylaxis and defines PI3K as new potential targets for treating anaphylaxis (Cauwels et al., 2006, J. Clin. Invest. 116(8): 2244-51).

Diseases and disorders associated especially with PI3K are cancer, cardiovascular disorders metabolic diseases, neurodegenerative disorders or infectious diseases.

Yet another aspect of the present invention is the use of a compound of the present invention or a pharmaceutically acceptable salt thereof for the manufacture of a medicament for the treatment or prophylaxis of cancer, metabolic diseases, neurodegenerative disorders, infectious diseases or cardiovascular disorders, more specifically myocardial infarction, stroke, ischemia or atherosclerosis.

Cancer comprises a group of diseases characterized by uncontrolled growth and spread of abnormal cells. All types of cancers generally involve some abnormality in the control of cell growth, division and survival, resulting in the malignant growth of cells. Key factors contributing to said malignant growth of cells are independence from growth signals, insensitivity to anti-growth signals, evasion of apoptosis, limitless replicative potential, sustained angiogenesis, tissue invasion and metastasis, and genome instability (Hanahan and Weinberg, 2000. The Hallmarks of Cancer. Cell 100, 57-70).

Typically, cancers are classified as hematological cancers (for example leukemias and lymphomas) and solid cancers such as sarcomas and carcinomas (for example cancers of the brain, breast, lung, colon, stomach, liver, pancreas, prostate, ovary).

Obesity and diabetes mellitus type 2 represent a steadily increasing health risk worldwide. Leptin, secreted by adipose tissue and acting in part through its hypothalamic receptor, integrates the energy state of peripheral organs and the action of the central nervous system inhibiting food intake and stimulating energy expenditure. The pancreas-derived peptide hormone insulin enters the central nervous system (CNS) through the blood-brain barrier by receptor-mediated transport to regulate food intake, sympathetic activity and peripheral insulin action through the inhibition of hepatic gluconeogenesis and reproductive endocrinology. On a molecular level, some of the effects of insulin converge with those of the leptin signaling machinery at the point of activation of phosphatidylinositol 3-kinase (PI3K), resulting in the regulation of ATP-dependent potassium channels. In accordance with this idea, intracerebroventricular (icv) injection of PI3K inhibitors partly abolishes the ability of both insulin and leptin to inhibit food intake (Xu et al., 2005, J. Clin. Inv., 115 (4): 951-8; Niswender et al., 2003, Diabetes 52:227-231). Furthermore, insulin inhibits neuronal apoptosis via activation of protein kinase B in vitro, and it regulates phosphorylation of tau, metabolism of the amyloid precursor protein and clearance of beta-amyloid from the brain in vivo. These findings indicate that neuronal IR signaling has a direct role in the link between energy homeostasis, reproduction and the development of neurodegenerative diseases (Plum et al., 2005, Trends Endocrinol. Metab. 16(2):59-65). Leptin causes a delayed apoptosis of mature neutrophils through a signaling cascade involving PI3K (Bruno et al., 2005, J. Immunol. 174: 8090-96). PI3K inhibitors may turn out beneficial in the treatment of diseases where the processes mentioned above are involved.

Recent work has demonstrated that the PI3K (phosphoinositide 3-kinase) signalling pathway is important for efficient influenza A virus replication. Activation of PI3K in virus-infected cells is mediated by the viral NS1 protein, which binds directly to the p85beta regulatory subunit of PI3K and causes the PI3K-dependent phosphorylation of Akt (protein kinase B). Given that recombinant influenza A viruses unable to activate PI3K signalling are attenuated in tissue culture, the PI3K pathway could be a novel target for the development of future anti-influenza drugs (Erhardt et al., 2007, J. Virol. 81 (7): 3058-67; Hale et al., 2006, PNAS 103, 14194-14199).

Another object of the present invention is a method for treating, controlling, delaying or preventing in a mammalian patient in need of the treatment of one or more conditions selected from the group consisting of diseases and disorders associated with PI3K, wherein the method comprises the administration to said patient a therapeutically effective amount of a compound according to present invention or a pharmaceutically acceptable salt thereof.

Yet another object is a method for treating, controlling, delaying or preventing in a mammalian patient in need of the treatment of one or more conditions selected from the group consisting of immunological; inflammatory; and allergic disorders, wherein the method comprises the administration to said patient a therapeutically effective amount of a compound according to the present invention or a pharmaceutically acceptable salt thereof.

More specifically the one or more conditions are selected from the group consisting of autoimmune diseases; organ and bone marrow transplant rejection; graft-versus-host disease; acute or chronic inflammation; pancreatitis; contact dermatitis; psoriasis; rheumatoid arthritis; multiple sclerosis; type I diabetes; inflammatory bowel disease; Crohn's disease; ulcerative colitis; systemic lupus erythematosus; asthma; chronic obstructive pulmonary disease (COPD); acute respiratory distress syndrome (ARDS); bronchitis; conjunctivitis; dermatitis; and allergic rhinitis; acute gouty inflammation; cystic fibrosis; familial Mediterranean fever; tissue damage after bacterial infection; Sweet's syndrome; or anaphylaxis.

More preferred are rheumatoid arthritis (RA), inflammatory bowel disease (IBD), systemic lupus erythematosus (SLE), psoriasis, multiple sclerosis (MS), asthma and chronic obstructive pulmonary disease (COPD).

Yet another object of the present invention is a method for treating, controlling, delaying or preventing in a mammalian patient in need of the treatment of one or more conditions selected from the group consisting of cancer; metabolic diseases; neurodegenerative disorders; infectious diseases and cardiovascular disorders, more specifically myocardial infarction, stroke, ischemia or atherosclerosis, wherein the method comprises the administration to said patient a therapeutically effective amount of a compound according to the present invention or a pharmaceutically acceptable salt thereof.

As used herein, the term "treating" or "treatment" is intended to refer to all processes, wherein there may be a slowing, interrupting, arresting, or stopping of the progression of a disease, but does not necessarily indicate a total elimination of all symptoms.

Without intending to be limited by theory, the compounds of the invention may also modulate in addition or alternatively immune cell activation via inhibition of PI3K. Especially the important roles of PI3Kδ and PI3Kγ in signaling and other functions of T cells, B cells, neutrophils, macrophages and mast cells indicate that these kinases are valid therapeutic targets for several inflammation-mediated diseases. These diseases comprise rheumatoid arthritis (in which T cells, B cells and neutrophils are involved), systemic lupus erythematosus (in which neutrophils are involved), psoriasis (in which T cells, neutrophils and macrophages are engaged), multiple sclerosis (in which T cells, B cells and mast cells are implicated), asthma (for which T cell and mast cells are important), and chronic obstructive pulmonary disease (which involves neutrophils, macrophages and T cells) (Rommel et al., 2007, Nat. Rev. Immunology 7:191-201).

In some cases, the link between PI3Kδ and PI3Kγ as potential drug targets for specific diseases has been experimentally established by testing the respective PI3K-null mice in animal disease models. Additional pharmacological confirmation was obtained by using small molecule PI3K inhibitors in wild-type mice in which inflammatory diseases were experimentally induced.

Camps and colleagues used structure-based drug design to develop a potent small molecule inhibitor of PIK3γ referred to as AS-605240 (Camps et al., 2005. Nat. Med. 11(9):936-43). It was observed that Pik3cg-null mice were protected against arthritis induced by collagen II-specific antibodies, a murine model of lymphocyte-independent rheumatoid arthritis (RA) associated with neutrophil activation. The effect was associated with impaired neutrophil chemotaxis. Treatment of wild-type mice with oral AS-605420 resulted in reduced clinical and histologic signs of collagen II-antibody-induced arthritis, similar to that seen in the Pik3cg-null mice. Oral AS-605240 also resulted in decreased joint inflammation and damage in a distinct mouse model of lymphocyte-dependent rheumatoid arthritis induced by direct collagen II injection. The authors concluded that PIK3CG inhibition operates on both the neutrophil and lymphocyte arms of chemokine signaling pathways, and thus may be of therapeutic value in various chronic inflammatory diseases.

In the MRL-lpr mouse model of systemic lupus erythematosus (SLE) it was found that intraperitoneal administration of the pharmacologic PI3Kγ inhibitor AS-605240 reduced CD4+ T-cell populations, reduced glomerulonephritis, and prolonged life span (Barber et al., 2005, Nat. Med. 11(9):933-935).

The involvement of PI3 kinases in allergic inflammatory diseases such as asthma was demonstrated through pharmacological inhibition by non-selective PI3K inhibitors such as wortmannin and LY294002. However, these compounds were not selective enough to discriminate between distinct PI3K isoforms (Walker et al., 2006, Drug Discovery Today: Disease Mechanisms, 3(1):63-69).

Using selective PI3Kδ inhibitors it was demonstrated that PI3Kδ plays a role in neutrophil inflammatory responses. Inhibition of PI3Kδ blocked both fMLP- and TNF1α-induced neutrophil superoxide generation and elastase exocytosis (Sadhu et al., 2003, Biochem. Biophys. Res. Commun. 2003 Sep. 5; 308(4):764-769).

The essential role of PI3Kδ in allergic responses was demonstrated by genetic and pharmacological inactivation of PI3Kδ in mast cells. This inhibition leads to defective SCF-mediated in vitro proliferation, adhesion and migration, and to impaired allergen-IgE-induced degranulation and cytokine release. Moreover, inactivation of PI3Kδ protects mice against anaphylactic allergic responses. Taken together, these studies suggest PI3Kδ as a target for therapeutic intervention in allergy and mast-cell-related diseases (Ali et al., 2004, Nature 431:1007-1011).

Recently, the effect of genetic inactivation of the Pi3kcd gene in mice on systemic cytokine and chemokine responses and allergic airway inflammation was reported. Type 2 cytokine responses (IL-4, IL-5, and IL-13) were significantly decreased in PI3Kδ mutants, whereas type 1 cytokine responses (IFN-γ CXCL10) were robust. For example, induction of respiratory hyper-responsiveness to inhaled methacholine, a hallmark of asthma, was attenuated in PI3Kδ null mice. In summary, these data suggest PI3Kδ as a new target for TH2-mediated airway diseases (Nashed et al., 2007, Eur. J. Immunol. 37:416-424).

Accordingly, diseases and disorders are preferred which are associated with PI3K delta and/or PI3K gamma. Especially preferred are inflammatory and immunoregulatory disorders rheumatoid arthritis, inflammatory bowel disease, systemic lupus erythematosus, psoriasis, multiple sclerosis, asthma and chronic obstructive pulmonary disease.

As mentioned above, PI3K also plays a role with regard to cancer and cardiovascular disorders.

PI3Kγ has been proposed as a possible target for pharmacological intervention in the primary and secondary prevention of human atherosclerotic cardiovascular disease. Atherosclerosis and its sequelae, including myocardial infarction and stroke, are the leading causes of mortality and morbidity in the developed world. It has been reported that PI3Kγ is activated in macrophages by oxidized LDL, agonists, chemokines and inflammatory mediators commonly implicated in atherogenesis. Genetic ablation of PI3 Kg in hypercholesterolemic mice (apoE−/−) results in reduced atherosclerotic lesions. In addition to retarding plaque progression, it is of clinical relevance the possibility that the inhibition of PI3K might affect plaque stability (Chang et al., 2007, PNAS 104 (19):8077-82).

This may be based on the fact that signaling through PI3Kγ plays an important role for leucocyte, platelet and cardiovascular stress sensing. The concerted activation of leukocytes and vessels influences may physiological and pathological responses usually leading to the production of intracellular second messenger molecules such as phosphatidylinositol(3, 4,5)-trisphosphate (PIP3), which is produced by PI3Kγ, a crucial signal in both vascular and white blood cells. The study of mice lacking PI3Kγ revealed that the PIP3 signaling pathway controls immune cell and vascular functions such as respiratory burst, cell recruitment, mast cell reactivity, platelet aggregation, endothelial activation and smooth muscle cell contractility. The specificity of these events suggests that inhibition of PI3Kγ may be beneficial for major cardiovascular disorders such as hypertension (Hirsch et al., 2006, Thromb. Haemost. 95(1):29-35).

Myocardial infarction (MI) results from a biphasic ischemia/reperfusion (I/R) injury to the heart, initiating with cardiomyocyte apoptosis (Crow et al., 2004, Circ. Res. 95(10):957-970) and then proceeding to a second wave of inflammation-based tissue damage (Frangogiannis et al., 2002, Cardiovasc. Res. 53(1):31-47). Recently, it was reported that a small molecule inhibitor of PI3K gamma and delta provided cardioprotection in an animal model of myocardial infarction. This compound, TG100-115, potently inhibits edema and inflammation in response to multiple mediators known to play a role in myocardial infarction. Importantly, this was achieved when dosing after myocardial reperfusion (up to 3 hours after), the same time period when patients are most accessible for therapeutic intervention (Doukas et al., 2006, PNAS 103(52):19866-19871; Doukas et al., 2007, Biochem. Soc. Trans. 35(Pt2):204-206; Palanki et al., 2007, J. Med. Chem. 50(18)-4279-4294).

The first study to describe point mutations of the PIK3CA gene, which encodes the p110α catalytic subunit, in colorectal, brain, gastric, breast and lung cancers, was reported in 2004 (Samuels et al., 2004, Science 304:554). Subsequently, several additional point mutations were identified in other cancer types (reviewed by Bader et al., 2005, Nat. Rev. Cancer 5(12): 921-929). It was demonstrated that PIK3CA mutants promote cell growth and invasion of human cancer cells and that treatment with the non-selective PI3K inhibitor LY294002 abrogated PIK3A signaling and preferentially inhibited growth of PI3KCA mutant cells (Samuels et al., 2005, Cancer Cell 7(6):561-573), thus suggesting PI3K proteins as promising drug targets for cancer therapy (Hennessy et al., 2005, Nat. Rev. Drug Discovery 4(12):988-1004).

Recently, it was reported that the overexpression of the wild-type PI3K isoforms PI3Kβ (p110β), PI3Kγ (p110γ) or PI3Kδ (p110δ) is sufficient to induce an oncogenic phenotype in cultured cells (Kang et al., 2006, PNAS 103(5): 1289-1294). This oncogenic potential required kinase activity suggesting that inhibitors of this activity may block the transforming capacity. The role of the non-α class I PI3K isoforms in human cancer has not been fully explored but there are reports of elevated expression of PI3Kβ and PI3Kδ in various human cancers (Benistant et al., 2000, Oncogene 19(44): 5083-5090; Knobbe and Reifenberger, 2003, Brain Pathol. 13(4):507-518). In another study it was demonstrated that a selective inhibitor of PI3Kδ (p110delta) inhibited the proliferation and survival of acute myeloid leukemia (AML) cells and increased the cytotoxic effects of a topoisomerase II inhibitor suggesting PI3Kδ as a potential therapeutic target in AML (Billottet et al., 2006. Oncogene 25(50):6648-6659).

The present invention provides pharmaceutical compositions comprising a compound of formula (I) or a pharmaceutically acceptable salt thereof as active ingredient together with a pharmaceutically acceptable carrier, optionally in combination with one or more other pharmaceutical compositions.

"Pharmaceutical composition" means one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the therapeutic, preferably in purified form, together with a suitable amount of carrier so as to provide the form for proper administration to the patient. The formulation should suit the mode of administration.

A pharmaceutical composition of the present invention may comprise one or more additional compounds as active ingredients like one or more compounds of formula (I) not being the first compound in the composition or PI3K inhibitors.

Other active ingredients for use in combination with other therapies for the treatment of immune, inflammatory, allergic disorders and may include steroids, leukotriene antagonists, anti-histamines, cyclosporine or rapamycin.

The pharmaceutical compositions of the present invention include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of formula (I) can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally, for example, as liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula (I) may also be administered parenterally. Solutions or suspensions of these active compounds can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of formula (I) are administered orally.

The effective dosage of active ingredient employed may vary depending on the particular compound employed, the mode of administration, the condition being treated and the severity of the condition being treated. Such dosage may be ascertained readily by a person skilled in the art.

A general route for the synthesis of compounds or formula (I) may start with triazoles of formula (II) which are readily available by conventional methods for the preparation of this type of heterocycle. Such methods are well known for the person skilled in the art.

A general preparation process for compounds according to the present invention, comprises the step of
reacting a triazole of formula (II)

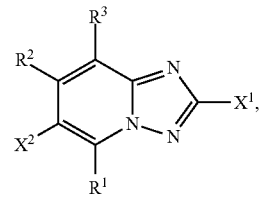

wherein $X^2$ is Br or $B(OR)_2$; $R^1$, $R^2$, $R^3$ have the meaning as indicated above and $X^1$ is X as indicated above or in protected form X-Pro, wherein Pro is a protective group, with boronic acid or ester $T^1$-$B(OR)_2$ or $T^1$-Br, wherein R is H; or a suitable ester residue, in a Suzuki reaction to give compounds of formula (I) after optional cleavage of the protective group.

For example such a protective group is acetyl.

More specifically, general and exemplary preparation routes are given below.

General Synthetic Methods

Methods for the synthesis of the compounds of the present invention are described e.g., in Houben-Weyl, Methoden der Organischen Chemie (Methods of Organic Chemistry), Thieme-Verlag, Stuttgart, or Organic Reactions, John Wiley & Sons, New York.

Depending on the circumstances of the individual case, in order to avoid side reactions during the synthesis of a compound of formula (I), it can be necessary or advantageous to temporarily block functional groups by introducing protective groups and to deprotect them in a later stage of the synthesis, or introduce functional groups in the form of precursor groups which in a later stage are converted into the desired functional groups. Such synthesis strategies and protective groups and precursor groups which are suitable in an individual case are known to the person skilled in the art.

If desired, the compounds of the formula (I) can be purified by customary purification procedures, for example by distillation, recrystallization or chromatography. The starting compounds for the preparation of the compounds of the formula (I) are commercially available or can be prepared according to or analogously to literature procedures.

A general route for the synthesis of compounds of formula (I) may start with triazoles of formula (II) which are readily available by conventional methods for the preparation of this type of heterocycle. Such methods are well known for the person skilled in the art.

According to Scheme 1, triazoles of formula (II), wherein $X^1$ is X as such as indicated above or in protected form, $X^2$ is bromo and $R^1$, $R^2$, $R^3$ have the meaning as indicated above, when reacted with boronic acid $T^1$-B(OH)$_2$ or boronic ester $T^1$-B(OR)$_2$ under Suzuki coupling (Suzuki et al., *Chem. Commun.* (1979) 866) conditions may give compounds of formula (I).

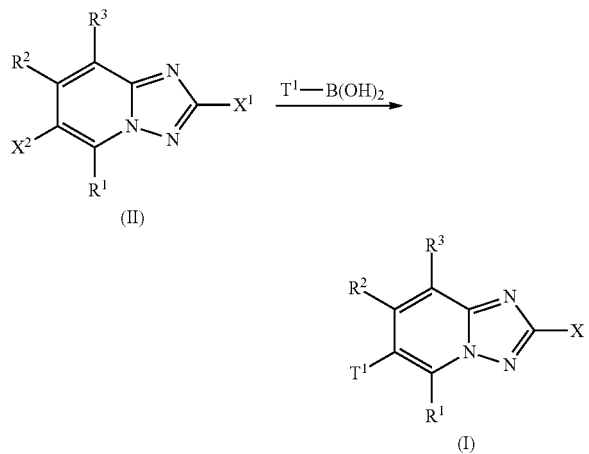

$T^1$-B(OH)$_2$ and $T^1$-B(OR)$_2$ as suitable starting materials for the synthesis of preferred compounds of the present invention may be purchased from commercially available sources such as CombiBlocks, Sigma Aldrich, AlfaAesar or be synthesized by one skilled in the art.

In a preferred embodiment of the present invention the preparation of triazoles of formula (II), wherein X is NH$_2$ may start with a pyridine of formula (III) which is reacted with ethoxycarbonyl isothiocyanate to yield after cyclisation in the presence of hydroxylamine the triazoles of formula (II) as outlined in Scheme 2.

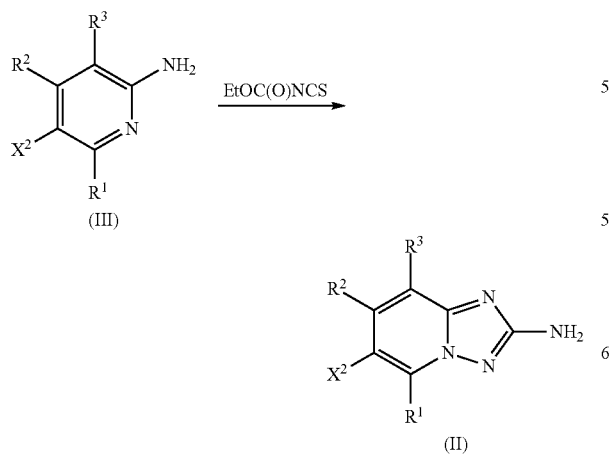

In a general procedure for the preparation of preferred compounds of the present invention reaction of commercially available 2-amino-5-bromopyridine [1] with ethoxycarbonyl isothiocyanate in DCM at 20° C. affords a thiourea derivative [2] as intermediate product which is subjected to a cyclisation procedure, employing hydroxylamine in a protic solvent (NH$_2$OH.HCl, $^i$Pr$_2$NEt, EtOH/MeOH, Δ), to yield key intermediate 2-amino-6-bromo-[1,2,4]triazolo[1,5-a]pyridine [3]. Subsequent acylation of the pyridine using acetyl chloride in the presence of Et$_3$N in CH$_3$CN at 20° C. generally gives a bis-acylated product which requires hydrolysis to the mono-acylated product [4] using methanolic ammonia solution at 20° C. Reaction of N-(6-bromo-[1,2,4]triazolo[1,5-a]pyridin-2-yl)acetamide [4] with 4,4,4',4',5,5,5',5'-octamethyl-2,2'-bi(1,3,2-dioxaborolane) (pinacol-diboron) in DMF with a base such as sodium carbonate in the presence of Pd(PPh$_3$)$_2$Cl$_2$ as catalyst affords N-(6-(4,4,5,5-tetramethyl-1,3,2-dioxaborolan-2-yl)-[1,2,4]triazolo[1,5-a]pyridin-2-yl)acetamide [5] Scheme 3.

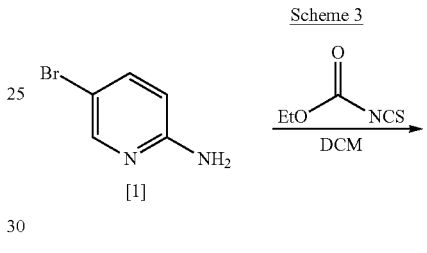

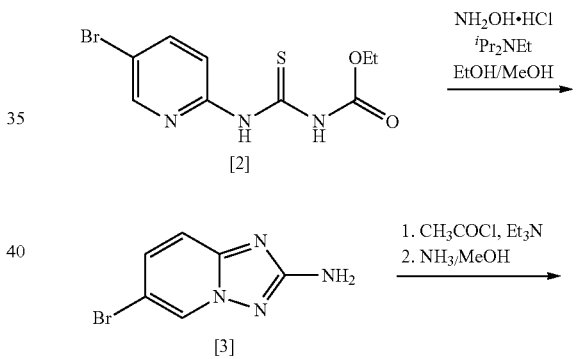

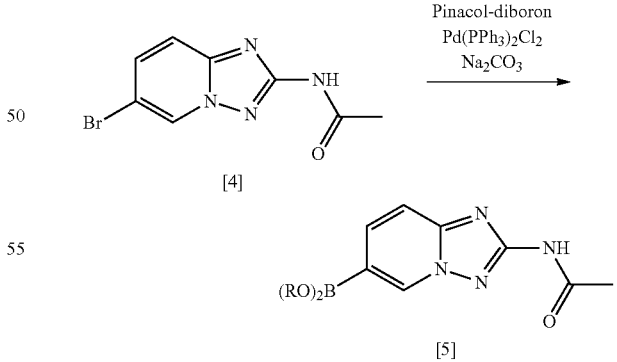

The preferred compounds of the present invention may be synthesised by coupling of the intermediate triazoles [3], [4] or [5] with the respective aryl boronic acids/esters or bromides under Suzuki reaction conditions using Pd(PPh$_3$)$_2$Cl$_2$ as catalyst and sodium carbonate as base in DME/H$_2$O/EtOH at 100-150° C. to afford the desired products [7], Scheme 4.

Scheme 4

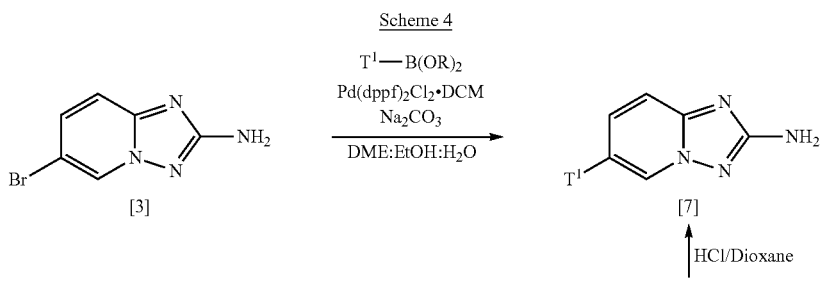

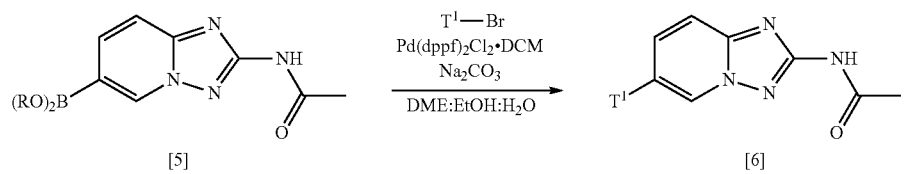

The acetyl protecting group is removed by treatment of the intermediate [6] with acid in a suitable solvent such as dioxane. The aryl boronic acids/esters or bromides were either selected from those commercially available or synthesised by elaboration of commercially available intermediates using the methods shown below.

Analytical Methods

NMR spectra were obtained on a Brucker dpx400. LCMS was carried out on an Agilent 1100 using a ZORBAX® SB-C18, 4.6×150 mm, 5 microns, ZORBAX® SB-C18, 4.6×75 mm, 3.5 micron or Gemini™ C18, 3×30 mm, 3 microns column. Column flow was 1.0 or 1.2 mL/min. and solvents used were water and acetonitrile (0.1% formic acid) with an injection volume of 3 or 10 ul. Wavelengths were 254 and 210 nm.

Method A

Column: ZORBAX® SB-C18, 4.6×150 mm, 5 microns

| Time (min) | Water | Acetonitrile |
|---|---|---|
| 0 | 95 | 5 |
| 11 | 5 | 95 |
| 13 | 5 | 95 |
| 13.01 | 95 | 5 |
| 14.00 | STOP | |

Method B

Column: ZORBAX® SB-C18, 4.6×75 mm, 3.5 microns

| Time (min) | Water | Acetonitrile |
|---|---|---|
| 0 | 70 | 30 |
| 1.5 | 5 | 95 |
| 4.5 | 5 | 95 |
| 4.51 | 70 | 30 |
| 5.00 | STOP | |

Method C

Column: Gemini C18, 3×30 mm, 3 microns Flow rate: 1.2 mL/min

| Time (min) | Water | Acetonitrile |
|---|---|---|
| 0 | 95 | 5 |
| 3 | 5 | 95 |
| 4.5 | 5 | 95 |
| 4.6 | 95 | 5 |
| 5.00 | STOP | |

Method D

Column flow was 1 mL/min. and solvents used were water and acetonitrile (0.1% ammonia).

Column: Gemini C18, 3×30 mm, 3 microns. Flow rate: 1.2 mL/min

| Time (min) | Water | Acetonitrile |
|---|---|---|
| 0 | 95 | 5 |
| 3 | 5 | 95 |
| 4.5 | 5 | 95 |
| 4.6 | 95 | 5 |
| 5.00 | STOP | |

TABLE 1

| Abbreviations | |
|---|---|
| DCM | Dichloromethane |
| Et$_3$N | Triethyl amine |
| CH$_3$CN | Acetonitrile |
| MeOH | Methanol |
| EtOH | Ethanol |
| $^i$Pr$_2$NEt | Diisopropylethylamine |
| NH$_2$OH•HCl | Hydroxylamine hydrochloride |
| Pd(PPh$_3$)$_2$(Cl)$_2$ | Bistriphenylphosphino-palladium(II)chloride |
| Pd(dppf)(Cl)$_2$ | [1,1'bis(diphenylphosphino)ferrocene] dichloro-palladium (II) |
| CsF | Caesium fluoride |
| DMF | N,N-Dimethylformamide |
| DME | 1,2-Dimethoxyethane |
| HOBt | 1-Hydroxybenzotriazole |
| EDC | N-Ethyl-N'-(3-dimethylaminopropyl)carbodiimide hydrochloride |
| H$_2$O | Water |
| s | Singlet |
| d | Doublet |
| dd | Doubledoublet |
| t | Triplet |
| sept | Septet |

TABLE 1-continued

| | Abbreviations |
|---|---|
| m | Multiplet |
| br | Broad |
| mL | Milliliters |
| L | Liter |
| h | hours |

The following methods were used for the preparation of compounds of formula (I).

Method 1

1.1 3-bromo-N,N-bis(2-hydroxyethyl)benzenesulfonamide

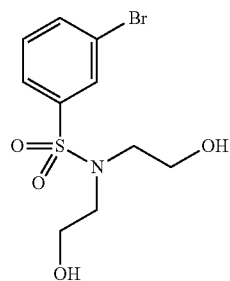 [SMILES: O=S(=O)(c1cccc(Br)c1)N(CCO)CCO]

To a solution of 3-bromobenzene sulfonyl chloride (0.25 mL, 1.73 mmol) in dioxane (2.0 mL) was added dropwise a solution of diethanolamine (0.547 g, 5.20 mmol) in dioxane (1.0 mL) over 1 min. The reaction mixture was stirred at room temperature (20° C.) for 16 h. After this time the mixture was poured onto brine (30 mL) and extracted with ethyl acetate (25 mL). The organic liquor was concentrated in vacuo to afford the title compound, (0.495 g, 88%). No further purification was required.

Other sulfonamides were prepared in an analogous way using 3-bromobenzene sulfonyl chloride or 3-bromopyridine sulfonyl chloride and different amines.

1.2 N-(5-bromopyridin-3-yl)benzenesulfonamide

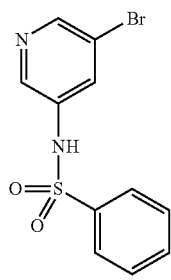 [SMILES: O=S(=O)(Nc1cncc(Br)c1)c1ccccc1]

To a solution of 3-amino-5-bromopyridine (0.500 g, 2.89 mmol) in pyridine (2 mL) was added benzenesulfonyl chloride (0.404 mL, 3.18 mmol) dropwise. The reaction mixture was stirred at room temperature (20° C.) for 16 h. After this time, water (5 mL) was added to the reaction mixture. The resulting crystalline solid was collected by filtration, washed with water and dried in the vacuum oven to afford the title compound (0.898 g, 2.89 mmol, quantitative). No further purification was required.

Other sulfonamides were prepared using an analogous method with different sulfonyl chlorides either at room temperature or 60° C.

1.3 4-Bromo-2-isopropoxy-1-methoxybenzene

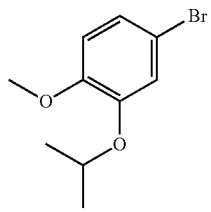

To a solution of 5-bromo-2-methoxyphenol (0.200 g, 1 mmol) in DMF (4 mL) was added potassium carbonate (0.209 g, 1.5 mmol) and isopropyliodide (120 μL, 1.2 mmol), the reaction mixture was stirred at room temperature (20° C.) for 3 h. After this time the crude reaction mixture was diluted with ethyl acetate (100 mL) and washed with water (2×100 mL). The organic layer was dried over magnesium sulfate, filtered and concentrated in vacuo to afford a yellow oil (200 mg, 0.81 mmol, 82%). No further purification was required.

1.4 1-(6-Bromo-[1,2,4]trizolo[1,5-a]pyridine-2-yl)Urea

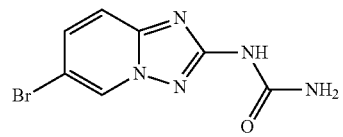 [SMILES: NC(=O)Nc1nc2ccc(Br)cn2n1]

To a solution of 6-Bromo-[1,2,4]triazolo[1,5-a]pyridin-2-ylamine (0.500 g, 2.34 mmol) in THF:pyridine (1:1, 15 mL) at 0° C. was added triphosgene (0.348 g, 1.17 mmol) over 5 min. The temperature was allowed to increase to 5° C. and 10% ammonia (20 mL) was added. The reaction mixture was then allowed to warm to room temp. (25° C.) and stirred for 16 h. After this time the solvent was removed in vacuo and the residue purified by column chromatography (eluent: ethyl acetate/hexane→ethyl acetate/methanol) to afford the title compound (0.089 g, 0.351 mmol, 15%).

Method 2

2.1 1-(5-Bromo-pyridin-2-yl)-3-carboethoxy-thiourea (2)

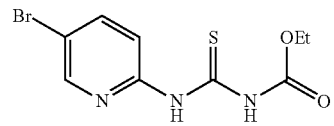 [SMILES: CCOC(=O)NC(=S)Nc1ccc(Br)cn1]

To a solution of 2-amino-5-bromopyridine (1) (200.0 g, 1.156 mol) in DCM (2.0 L) cooled to 5° C. was added ethoxycarbonyl isothiocyanate (134.9 mL, 1.156 mol) dropwise over 15 min. The reaction mixture was then allowed to warm to room temperature (20° C.) and stirred for 16 h. Evaporation in vacuo gave a yellow solid which was collected by filtration, thoroughly washed with petrol (3×500 mL) and air-dried to afford the title compound (351.5 g, quantitative). No further purification was required.

$^1$H NMR (d$_6$-DMSO) δ 12.22 (br s, 1H), 11.75 (br s, 1H), 8.66 (br s, 1H), 8.57 (d, 1H), 8.16 (dd, 1H), 4.26 (q, 2H), 1.28 (t, 3H).

2.2 6-Bromo-[1,2,4]triazolo[1,5-a]pyridin-2-ylamine (3)

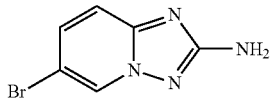 [SMILES: Nc1nc2ccc(Br)cn2n1]

To a suspension of hydroxylamine hydrochloride (409.2 g, 5.888 mol) in EtOH/MeOH (1:1, 2.5 L) was added N,N-diisopropylethylamine (606.1 mL, 3.480 mol), the mixture was stirred at room temperature (20° C.) for 1 h. 1-(6-Bromo-pyridin-2-yl)-3-carboethoxy-thiourea (2) (352.8 g, 1.160 mol) was then added and the mixture slowly heated to reflux (Note: bleach scrubber required to quench H$_2$S evolved). After 2 h at reflux the mixture was allowed to cool and filtered to collect the precipitated solid. The collected solid was washed successively with water (1.0 L), EtOH/MeOH (1:1, 1.0 L) and diethyl ether (500 mL) then air-dried to afford the title compound as a white solid (169.2 g, 69%). No further purification was required.

$^1$H NMR (d$_6$-DMSO) δ 8.94 (d, 1H), 7.58 (dd, 1H), 7.36 (d, 1H), 6.16 (br s, 2H). m/z 213/215 (1:1, M+H$^+$, 100%).

2.3 N-(6-bromo-[1,2,4]triazolo[1,5-a]pyridin-2-yl)acetamide (4)

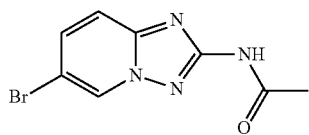

To a solution of 6-Bromo-[1,2,4]triazolo[1,5-a]pyridin-2-ylamine (3) (7.10 g, 33.3 mmol) in dry acetonitrile (150 mL) at 5° C. was added triethylamine (11.6 mL, 83.3 mmol) followed by acetyl chloride (2.35 mL 83.3 mmol). The reaction mixture was then allowed to warm to room temperature (20° C.) and stirred until all starting material was consumed (if required, further triethylamine (4.64 mL, 33.3 mmol) and acetyl chloride (33.3 mmol) were added to ensure complete reaction). After this time the solvent was removed in vacuo and to the resultant residue was added 7 N (Methanolic ammonia solution (50 mL)). The reaction mixture was stirred at room temperature (20° C.) to hydrolyze any bis-acylated material. After 16 h evaporation in vacuo and trituration from diethyl ether (50 mL) afforded the title compound which was collected by filtration, washed with water (2×50 mL), acetone (50 mL) and diethyl ether (50 mL) and then dried in vacuo.

$^1$H NMR (d$_6$-DMSO) δ 10.87 (s, 1H), 9.29 (d, 1H), 7.78 (dd, 1H), 7.65 (d, 2H), 2.13 (s, 3H).

2.4 N-(6-(4,4,5,5-tetramethyl-1,3,2-dioxaborolan-2-yl)[1,2,4]triazolo[1,5-a]pyridin-2-yl)acetamide (5)

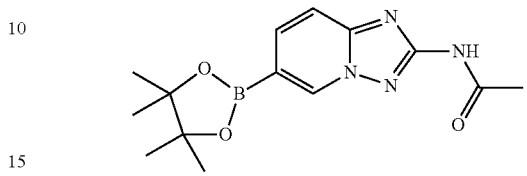

To a solution of N-(6-bromo-[1,2,4]triazolo[1,5-a]pyridin-2-yl)acetamide (4) (20.0 g, 78.4 mmol) in toluene (400 mL) was added bis(pinacolato)diboron (20.35 g, 86.2 mmol) and potassium acetate (15.39 g, 156.8 mmol). The reaction mixture was degassed and [1,1'-bisdiphenyl phosphine) ferrocene]palladium (II) chloride, 1:1 complex with DCM (3.2 g, 3.92 mmol) was added in one portion. The mixture was further degassed and heated at 100° C. for 16 h. After this time the reaction mixture was allowed to cool to room temperature (20° C.), filtered over celite and washed with ethyl acetate. The filtrate was washed with brine, dried over anhydrous sodium sulfate and the solvent removed in vacuo to afford the title compound (24.5 g, 78.4 mmol, quantitative). The crude material was used without further purification.

Method 3

3.1 General method of preparation of (6-Aryl-[1,2,4]triazolo[1,5-a]pyridin-2-ylamine) from (6-Bromo-[1,2,4]triazolo[1,5-a]pyridin-2-ylamine)

A suspension of 6-Bromo-[1,2,4]triazolo[1,5-a]pyridin-2-ylamine (3) (0.3 mmol, 1 eq), the boronic acid (0.36 mmol, 1.2 eq), [1,1' bis(diphenylphosphino)ferrocene]dichloro-palladium (II) complex with CH$_2$Cl$_2$ (0.006 mmol, 0.02 eq) and sodium carbonate (0.45 mmol, 1.5 eq) in DME:H$_2$O:EtOH, (7:3:2, 2 mL) was heated to 120° C. for 30 minutes in the microwave. The crude reaction was either partitioned between water and ethyl acetate, the phases separated and the organic layer washed with brine, dried over magnesium sulfate, filtered and the solvent removed in vacuo or precipitated by addition of water, the precipitate collected by filtration and washed with ethyl acetate and methanol. The crude residues were either purified by flash chromatography or preparative HPLC if required to afford the desired products.

3.2 General method of preparation of (6-Aryl-[1,2,4]triazolo[1,5-a]pyridin-2-ylamine) from (N-(6-(4,4,5,5-tetramethyl-1,3,2-dioxaborolan-2-yl)-[1,2,4]triazolo[1,5-a]pyridin-2-yl)acetamide)

Compounds were prepared following a similar procedure as for method 3.1 using (N-(6-(4,4,5,5-tetramethyl-1,3,2-dioxaborolan-2-yl)-[1,2,4]triazolo[1,5-a]pyridin-2-yl)acetamide and the appropriate aryl bromide, although before purification the crude residue was treated with 4M HCl/dioxane for 18 hours at room temperature. The solvent was removed in vacuo and the residues purified as described above.

Method 4

4.1 General method of preparation of 3-O-substituted 5-bromo-pyridines

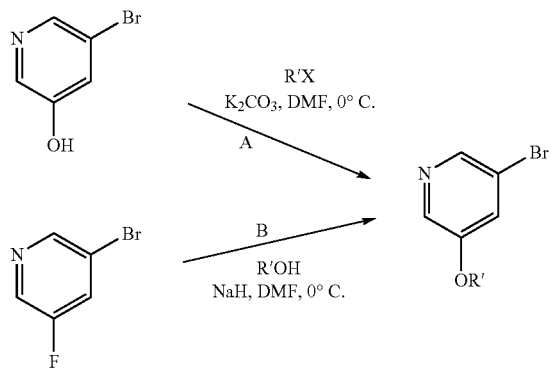

Method A:

5-bromo-pyridin-3-ol (174 mg, 1.0 mmol) and potassium carbonate (143 mg, 1.03 mmol) were cooled to 0° C. in DMF (5 mL). The halide R'X (1.0 mmol) was added and the reaction mixture was stirred at 0° C. for 90 minutes. After this time ethyl acetate (50 mL) was added and the organic phase washed with sodium hydroxide (3×30 mL, 2M, aqueous solution). The organic phase was concentrated in vacuo to afford the required intermediate compound. No further purification was required.

Method B:

Sodium hydride (42 mg, 1.05 mmol) was carefully added to a stirred solution of the alcohol R'OH (1.0 mmol) in DMF (8 mL). The reaction mixture was stirred at 0° C. for 60 minutes after which time 3-bromo-5-fluoropyridine (176 mg, 1.0 mmol) was added. The reaction mixture was stirred at 110° C. overnight. After cooling the reaction mixture was poured onto brine solution (25 mL) and extracted with ethyl acetate (2×30 mL). The organic extracts were combined and concentrated in vacuo to afford the required intermediate compound. No further purification was required.

4.2 General method of preparation of 3-SO$_2$-substituted 5-bromo-pyridines

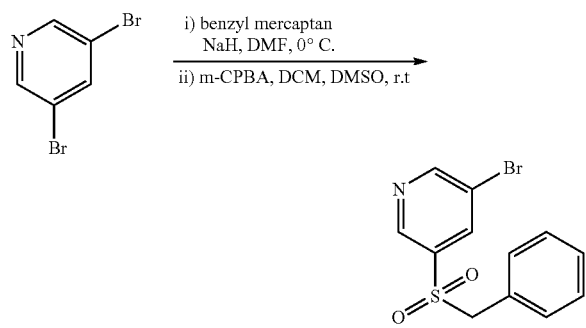

Sodium hydride (130 mg, 3.24 mmol) was added to a solution of benzyl mercaptan (0.37 mL, 3.15 mmol) in DMF (9 mL) at 0° C. and the reaction mixture was stirred for 70 minutes. 3,5-dibromopyridine (711 mg, 3.0 mmol) in DMF (4 mL) was added dropwise and the reaction mixture stirred at room temperature overnight. After this time the reaction mixture was poured onto dilute bleach solution (<5%, 100 mL) and extracted with ethyl acetate (2×60 mL). The organic liquors were combined and concentrated in vacuo to afford the intermediate thiol which was suspended in DCM (50 ml), meta-Chloroperbenzoic acid (1.08 g, 4.84 mmol) was added and the reaction mixture stirred at room temperature overnight. DMSO (0.4 mL) was added and the reaction mixture was stirred for further 2 hours. After this time the reaction was diluted further with DCM (20 mL) and washed with NaHCO$_3$ (2×50 mL) and brine (30 mL, dried over magnesium sulphate, filtered and concentrated in vacuo to afford the required intermediate compound, (610 mg, 1.95 mmol, 88%). No further purification was required.

Method 5

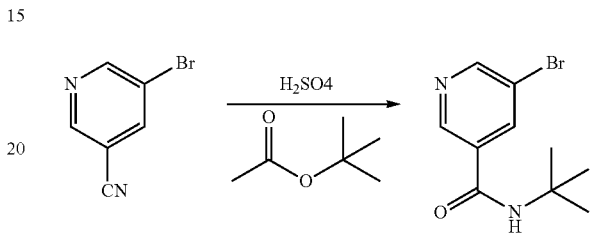

To a stirred suspension of 5-bromo-3-cyanopyridine (366 mg, 2.0 mmol) in tert-butyl acetate (2.25 mL) was added concentrated sulphuric acid (0.15 mL) dropwise at room temperature. The reaction mixture was heated at 45'C and stirred overnight. After this time the reaction mixture was poured onto saturated NaHCO$_3$ (20 mL) and extracted with ethyl acetate (40 mL). The organic extracts were concentrated in vacuo to afford the title compound; no further purification was required (480 mg, 1.87 mmol, 93%).

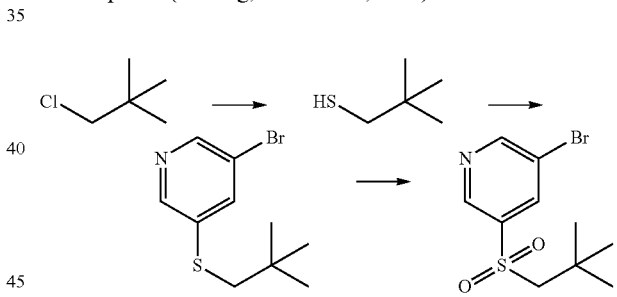

Neopentyl chloride (0.245 mL, 2.0 mmol) was added to a solution of sodium hydrogen sulphide (115 mg, 2.04 mmol) in DMF (3 mL) at room temperature and the reaction mixture stirred at 45° C. After 18 hours the reaction mixture was cooled and sodium hydride (80 mg, 2.0 mmol) added in one portion, the reaction mixture was then stirred at room temperature for 1 hour. 3-bromo-5-fluoropyridine (352 mg, 2.0 mmol) was added and the reaction mixture stirred at 50° C. overnight. After this time the reaction mixture was poured onto ethyl acetate (25 mL) and washed with dilute bleach solution (25 mL). The organic phase was concentrated in vacuo and the residue purified by flash chromatography to afford the desired thiol intermediate (340 mg, 1.3 mmol). This was dissolved in DCM (50 mL) and meta-Chloroperbenzoic acid (650 mg, 2.9 mmol) added, the reaction mixture was stirred at room temperature for 18 hours. DMSO (0.2 mL) was added and reaction mixture stirred for a further 2 hours. The reaction was diluted further with DCM (20 mL) and washed with saturated NaHCO$_3$ (2×30 mL). The organic phase was separated and the solvent removed in vacuo to afford the title intermediate compound, (366 mg, 1.25 mmol, 95%). No further purification was required.

EXAMPLES

The following examples were prepared using the above methods 3-(2-Amino-[1,2,4]triazolo[1,5-a]pyridin-6-yl)-N-(2-hydroxy-ethyl)-benzenesulfonamide

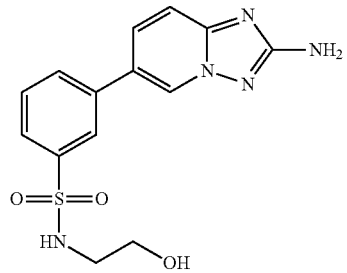 [SMILES: Nc1nc2ccc(-c3cccc(S(=O)(=O)NCCO)c3)cn2n1]

$^1$H NMR (d$_6$-DMSO) δ 8.90 (m, 1H), 8.11 (t, 1H), 8.01 (dm, 1H), 7.77-7.82 (m, 2H), 7.69 (t, 1H) 7.48 (dd, 1H), 6.15 (s, 2H), 4.74 (br, s, 1H), 3.39 (t, 2H), 2.83 (t, 2H); LCMS (method A), (M+H$^+$) 334, RT=5.46 min.

6-(5-Methanesulfonyl-pyridin-3-yl)-[1,2,4]triazolo[1,5-a]pyridin-2-ylamine

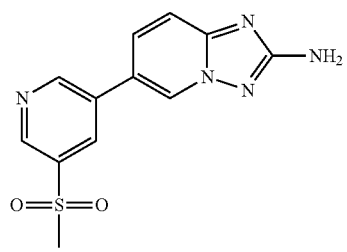 [SMILES: CS(=O)(=O)c1cncc(-c2ccc3nc(N)nn3c2)c1]

$^1$H NMR (d$_6$-DMSO) δ 9.30 (d, 1H), 9.23 (dd, 1H), 9.02 (d, 1H), 8.63 (t, 1H), 7.96 (dd, 1H) 7.51 (dd, 1H), 6.21 (s, 2H), 3.41 (s, 3H)
LCMS (method A), (M+H$^+$) 290, RT=5.31 min.

5-(2-Amino-[1,2,4]triazolo[1,5-a]pyridin-6-yl)-pyridine-3-sulfonic acid butylamide

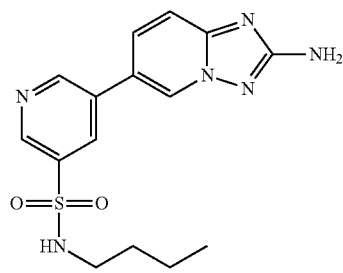 [SMILES: CCCCNS(=O)(=O)c1cncc(-c2ccc3nc(N)nn3c2)c1]

$^1$H NMR (d$_6$-DMSO) δ 10.91 (br, s, 1H), 9.50 (s, 1H), 9.27 (d, 1H), 8.96 (d, 1H), 8.52 (m, 1H), 8.08 (dm, 1H), 7.85 (m, 2H), 2.86 (br, m, 2H), 2.17 (br, s, 3H), 1.38 (br, m, 2H), 1.27 (br, m, 2H), 0.81 (t, 3H).
LCMS (method A), (M+H$^+$) 389, RT=6.50 min.

5-(2-Amino-[1,2,4]triazolo[1,5-a]pyridin-6-yl)-2-methoxy-phenol

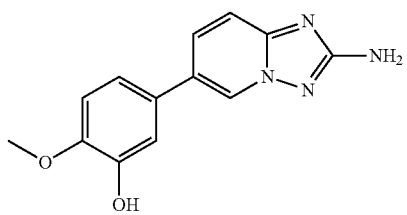 [SMILES: COc1ccc(-c2ccc3nc(N)nn3c2)cc1O]

$^1$H NMR (d$_6$-DMSO) δ 9.13 (br, s, 1H), 8.70 (m, 1H), 7.64 (dd, 1H), 7.37 (dd, 1H), 7.08-7.10 (m, 2H), 6.98-7.00 (m, 1H), 6.01 (s, 2H), 3.80 (s, 3H)
LCMS (method B), (M+H$^+$) 257, RT=1.43 min.

1-(6-(3,4-dimethoxyphenyl)-[1,2,4]triazolo[1,5-a]pyridin-2-yl)urea

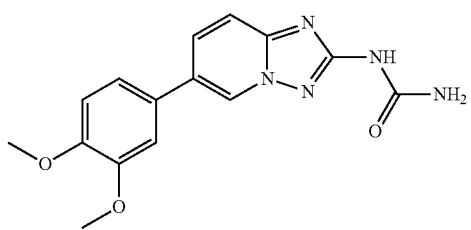 [SMILES: COc1ccc(-c2ccc3nc(NC(N)=O)nn3c2)cc1OC]

$^1$H NMR (d$_6$-DMSO) δ 9.83 (s, 1H), 9.11 (s, 1H), 7.97 (d, 1H), 7.67 (d, 1H), 7.32 (s, 1H), 7.28 (d, 1H), 7.04 (d, 1H), 3.85 (s, 3H, 3.79 (s, 3H).

5-(2-Amino-[1,2,4]triazolo[1,5-a]pyridin-6-yl)-pyridine-3-sulfonic acid tert-butylamide

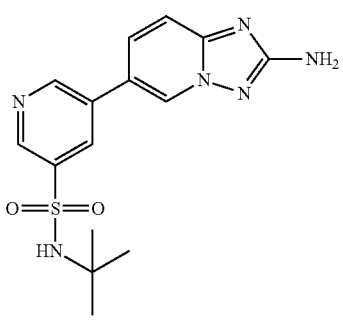 [SMILES: CC(C)(C)NS(=O)(=O)c1cncc(-c2ccc3nc(N)nn3c2)c1]

$^1$H NMR (d$_4$-MeOH) δ 9.31 (s, 1H), 9.29 (s, br, 2H), 8.87 (s, 1H), 8.40 (s, br, 1H), 7.91 (s, br, 1H), 3.66 (m, 1H), 1.26 (s, 9H)
LCMS (method A), (M+H$^+$) 347, RT=3.65 min.

5-(2-Amino-[1,2,4]triazolo[1,5-a]pyridin-6-yl)-pyridine-3-sulfonic acid benzylamide

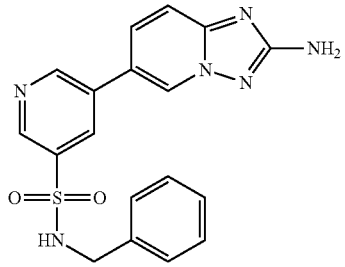 [SMILES: Nc1nc2ccc(-c3cncc(S(=O)(=O)NCc4ccccc4)c3)cn2n1]

$^1$H NMR (d$_6$-DMSO) δ 9.30 (s, br, 1H), 9.16 (s, 1H), 8.93 (s, 1H), 8.53 (t, 1H), 8.37 (s, 1H), 8.02 (d, 1H), 7.12-7.24 (m, 5H), 4.13 (d, 2H)

LCMS (method A), (M+H$^+$) 381, RT=3.95 min.

5-(2-Amino-[1,2,4]triazolo[1,5-a]pyridin-6-yl)-pyridine-3-sulfonic acid (2-ethyl-butyl)-amide

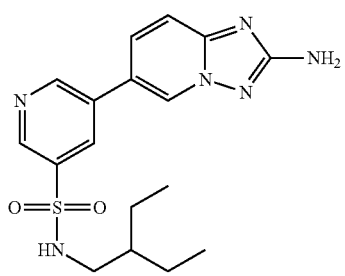 [SMILES: CCC(CC)CNS(=O)(=O)c1cncc(-c2ccc3nc(N)nn3c2)c1]

$^1$H NMR (d$_4$-MeOH) δ 9.31 (s, br, 2H), 9.18 (s, br, 1H), 8.79 (s, 1H), 8.40 (s, br, 1H), 7.90 (s, br, 1H), 3.66 (m, 1H), 2.91 (s, 2H), 1.35 (m, 4H), 0.85 (m, 6H)

LCMS (method A), (M+H$^+$) 375, RT=4.91 min.

5-(2-Amino-[1,2,4]triazolo[1,5-a]pyridin-6-yl)-pyridine-3-sulfonic acid (4-chloro-phenyl)-amide

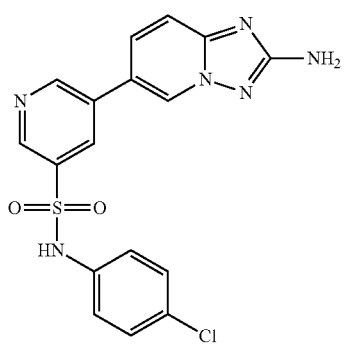 [SMILES: Nc1nc2ccc(-c3cncc(S(=O)(=O)Nc4ccc(Cl)cc4)c3)cn2n1]

$^1$H NMR (d$_4$-MeOH) δ 9.19 (s, 2H), 9.01 (s, br, 1H), 8.55 (s, 1H), 8.26 (d, 1H), 7.85 (d, 1H), 7.26 (d, 2H), 7.16 (d, 2H)

LCMS (method A), (M+H$^+$) 401, RT=4.72 min.

5-(2-Amino-[1,2,4]triazolo[1,5-a]pyridin-6-yl)-pyridine-3-sulfonic acid (3,5-bis-trifluoromethyl-phenyl)-amide

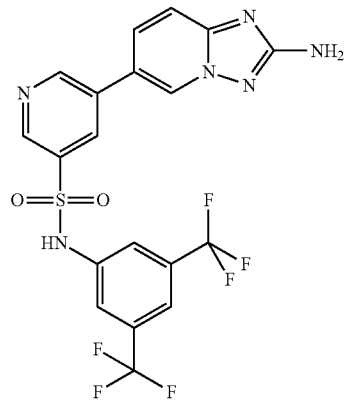 [SMILES: Nc1nc2ccc(-c3cncc(S(=O)(=O)Nc4cc(C(F)(F)F)cc(C(F)(F)F)c4)c3)cn2n1]

$^1$H NMR (d$_4$-MeOH) δ 9.21 (m, 1H), 9.18 (s, br, 1H), 9.04 (s, br, 1H), 8.66 (m, 1H), 8.31 (dm, 1H), 7.87 (d, 1H), 7.76 (s, 2H), 7.69 (s, 1H)

LCMS (method A), (M+H$^+$) 503, RT=5.98 min.

5-(2-Amino-[1,2,4]triazolo[1,5-a]pyridin-6-yl)-pyridine-3-sulfonic acid (4-fluoro-phenyl)-amide

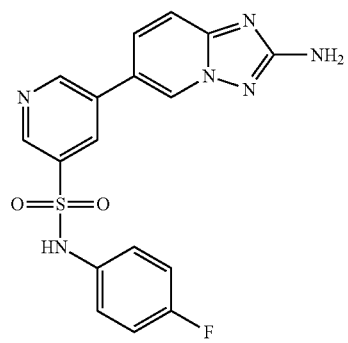 [SMILES: Nc1nc2ccc(-c3cncc(S(=O)(=O)Nc4ccc(F)cc4)c3)cn2n1]

$^1$H NMR (d$_4$-MeOH) δ 9.21 (s, 1H), 9.19 (s, br, 1H), 9.01 (s, br, 1H), 8.58 (s, 1H), 8.27 (d, 1H), 7.86 (d, 1H), 7.27 (d, 2H), 7.19 (d, 2H)

LCMS (method A), (M+H$^+$) 385, RT=4.20 min.

6-(3-Methanesulfonyl-phenyl)-[1,2,4]triazolo[1,5-a]pyridin-2-ylamine

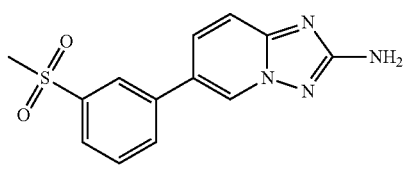 [SMILES: CS(=O)(=O)c1cccc(-c2ccc3nc(N)nn3c2)c1]

¹H NMR (d₆-DMSO) δ 9.09 (s, 1H), 8.24 (t, 1H), 8.11 (dd, 1H), 7.86-7.92 (m, 2H), 7.74 (t, 1H), 7.49 (d, 1H), 6.16 (s, 2H), 3.32 (s, 3H).
LCMS (method B), (M+H⁺) 289, RT=1.51 min.

6-(3,4-dimethoxyphenyl)-[1,2,4]triazolo[1,5-a]pyridin-2-amine

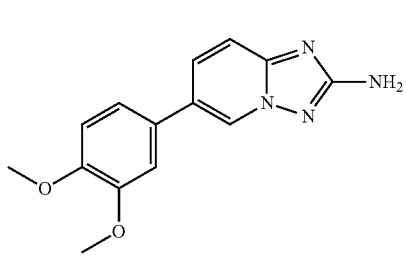 [SMILES: COc1ccc(-c2ccc3nc(N)nn3c2)cc1OC]

¹H NMR (d₄-MeOH) δ 8.64 (dd, 1H), 7.81 (dd, 1H), 7.41 (dd, 1H), 7.18-7.22 (m, 2H), 7.05 (d, 1H), 3.92 (s, 3H), 3.88 (s, 3H),
LCMS (method B), (M+H⁺) 271, RT=1.60 min.

3-(2-amino-[1,2,4]triazolo[1,5-a]pyridin-6-yl)-N-(2-aminoethyl)benzenesulfonamide

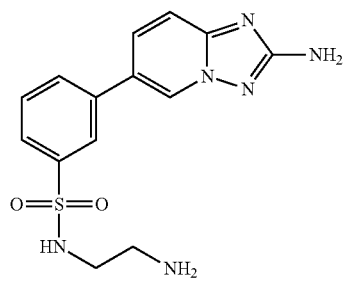 [SMILES: NCCNS(=O)(=O)c1cccc(-c2ccc3nc(N)nn3c2)c1]

¹H NMR (d₄-MeOD) δ 8.49 (s, 1H), 7.96 (s, 1H), 7.77 (d, 1H), 7.52-7.68 (m, 3H), 7.36 (d, 1H), 2.88 (brs, 2H), 2.68 (brs, 2H), 1.28 (s, 2H).
LCMS (Method B), (M+H⁺) 333, RT=0.74 min.

6-(3-isopropoxy-4-methoxyphenyl)-[1,2,4]triazolo[1,5-a]pyridin-2-amine

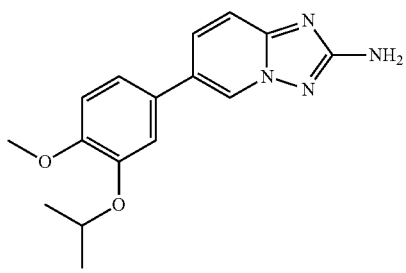 [SMILES: COc1ccc(-c2ccc3nc(N)nn3c2)cc1OC(C)C]

¹H NMR (d₄-MeOD): δ 8.99 (d, 1H), 8.26 (d, 1H), 7.75 (d, 1H), 7.32-7.35 (m, 2H), 7.14 (d, 1H), 4.69-4.72 (m, 1H), 3.91 (s, 3H), 1.37 (s, 3H), 1.37 (s, 3H).

4-(2-Amino-[1,2,4]triazolo[1,5-a]pyridin-6-yl)-2-methoxyphenol

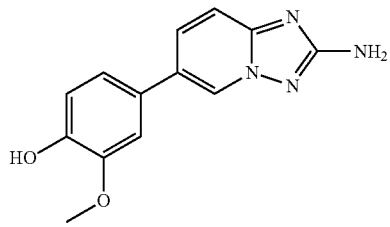 [SMILES: COc1cc(-c2ccc3nc(N)nn3c2)ccc1O]

¹H NMR (d₆-DMSO) δ 9.21 (br s, 1H), 8.82 (dd, 1H), 7.73 (dd, 1H), 7.37 (dd, 1H), 7.25 (d, 1H), 7.10 (dd, 1H), 6.84 (d, 1H), 6.00 (s, 2H), 3.34 (s, 3H).
LCMS (Method C), (M+H⁺) 257, RT=1.36 min.

3-(2-Amino-[1,2,4]triazolo[1,5-a]pyridin-6-yl)-N-butylbenzenesulfonamide

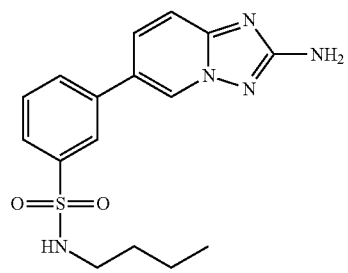 [SMILES: CCCCNS(=O)(=O)c1cccc(-c2ccc3nc(N)nn3c2)c1]

¹H NMR (d₆-DMSO) δ 8.98 (dd, 1H), 8.08 (t, 1H), 8.02-8.00 (m, 1H), 7.81-7.76 (m, 2H), 7.69 (t, 1H), 7.59 (br s, 1H), 7.49 (dd, 1H), 6.15 (br s, 2H), 2.76 (t, 2H), 1.39-1.31 (m, 2H), 1.28-1.19 (m, 2H), 0.79 (t, 3H).
LCMS (Method C), (M+H⁺) 346, RT=1.97 min.

4,4,4-Trifluorobutane-1-sulfonic acid [5-(2-amino-[1,2,4]triazolo[1,5-a]pyridin-6-yl)-pyridin-3-yl]amide

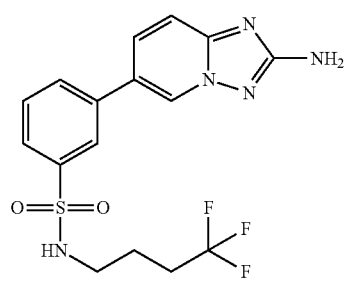 [SMILES: Nc1nc2ccc(-c3cccc(S(=O)(=O)NCCCC(F)(F)F)c3)cn2n1]

¹H NMR (d₆-DMSO) δ 10.32 (br s, 1H), 8.85 (br s, 1H), 8.31 (br s, 1H), 8.17 (d, 1H), 7.68 (dd, 1H), 7.61-7.60 (m, 1H), 7.45 (dd, 1H), 6.10 (br s, 2H), 3.08 (t, 2H), 2.46-2.36 (m, 2H), 1.91-1.84 (m, 2H).
LCMS (Method A), (M+H⁺) 401, RT=3.71 min.

41

N-[5-(2-Amino-[1,2,4]triazolo[1,5-a]pyridin-6-yl)-pyridin-3-yl]-3-trifluoromethylbenzenesulfonamide HCl salt

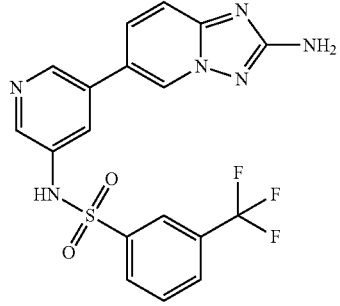 [SMILES: Nc1nc2ccc(-c3cncc(NS(=O)(=O)c4cccc(C(F)(F)F)c4)c3)cn2n1]

$^1$H NMR (d$_6$-DMSO) δ 9.17 (d, 1H), 8.75 (s, 1H), 8.34 (s, 1H), 8.13-8.12 (m, 2H), 8.07 (d, 1H), 7.96-7.94 (m, 2H), 7.84 (t, 1H), 7.67 (d, 1H).
LCMS (Method C), (M+H$^+$) 435, RT=2.22 min.

N-[5-(2-Amino-[1,2,4]triazolo[1,5-a]pyridin-6-yl)-pyridin-3-yl]-2-trifluoromethylbenzenesulfonamide HCl salt

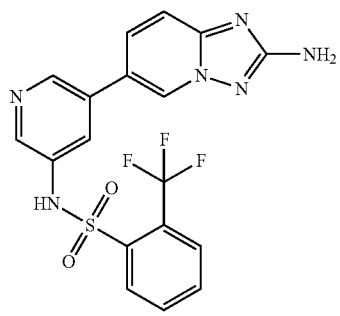 [SMILES: Nc1nc2ccc(-c3cncc(NS(=O)(=O)c4ccccc4C(F)(F)F)c3)cn2n1]

$^1$H NMR (d$_6$-DMSO) δ 9.06 (br s, 1H), 8.71 (br s, 1H), 8.36 (br s, 1H), 8.22 (d, 1H), 8.03 (dd, 1H), 7.93-7.80 (m, 4H), 7.60 (d, 1H)
LCMS (Method C), (M+H$^+$) 435, RT=2.13 min.

N-[5-(2-Amino-[1,2,4]triazolo[1,5-a]pyridin-6-yl)-pyridin-3-yl]-4-trifluoromethylbenzenesulfonamide HCl salt

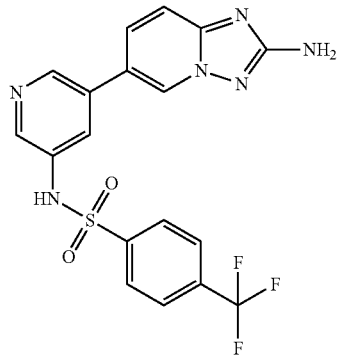 [SMILES: Nc1nc2ccc(-c3cncc(NS(=O)(=O)c4ccc(C(F)(F)F)cc4)c3)cn2n1]

42

$^1$H NMR (d$_6$-DMSO) δ 9.23 (br s, 1H), 8.78 (br s, 1H), 8.40 (br s, 1H), 8.08-7.97 (m, 6H), 7.73 (d, 1H).
LCMS (Method C), (M+H$^+$) 435, RT=2.26 min.

Naphthalene-2-sulfonic acid [5-(2-amino-[1,2,4]triazolo[1,5-a]pyridin-6-yl)-pyridin-3-yl]-amide HCl salt

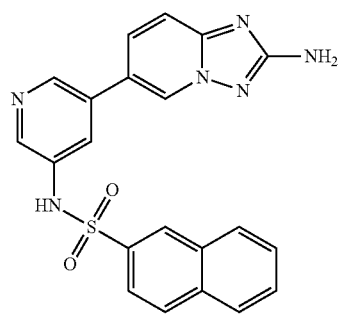 [SMILES: Nc1nc2ccc(-c3cncc(NS(=O)(=O)c4ccc5ccccc5c4)c3)cn2n1]

$^1$H NMR (d$_6$-DMSO) δ 11.21 (br s, 1H), 9.18 (br s, 1H), 8.69 (br s, 1H), 8.57 (d, 1H), 8.40 (br s, 1H), 8.17 (d, 1H), 8.13 (d, 1H), 8.03-8.00 (m, 2H), 7.96 (dd, 1H), 7.87 (dd, 1H), 7.72-7.63 (m, 3H).
LCMS (Method C), (M+H$^+$) 417, RT=2.21 min.

N-[5-(2-Amino-[1,2,4]triazolo[1,5-a]pyridin-6-yl)-pyridin-3-yl]-4-isopropylbenzenesulfonamide HCl salt

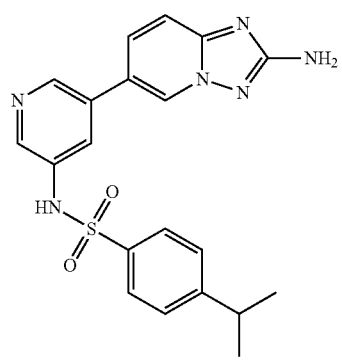 [SMILES: CC(C)c1ccc(S(=O)(=O)Nc2cncc(-c3ccc4nc(N)nn4c3)c2)cc1]

$^1$H NMR (d$_6$-DMSO) δ 11.06 (br s, 1H), 9.20 (br s, 1H), 8.75 (br s, 1H), 8.39 (br s, 1H), 7.97-7.95 (m, 2H), 7.78 (d, 2H), 7.70 (br d, 1H), 7.45 (d, 2H), 2.94 (sept, 1H), 1.16 (d, 6H).
LCMS (Method C), (M+H$^+$) 409, RT=2.30 min.

Naphthalene-1-sulfonic acid [5-(2-amino-[1,2,4]triazolo[1,5-a]pyridin-6-yl)-pyridin-3-yl]-amide HCl salt

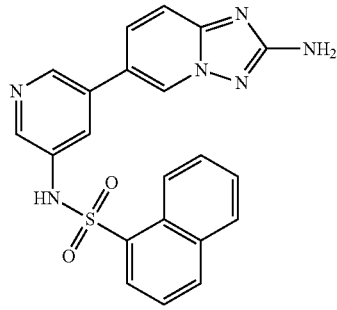 [SMILES: Nc1nc2ccc(-c3cncc(NS(=O)(=O)c4cccc5ccccc45)c3)cn2n1]

$^1$H NMR (d$_6$-DMSO) δ 11.43 (br s, 1H), 9.08 (br s, 1H), 8.73 (d, 1H), 8.61 (br s, 1H), 8.34 (dd, 1H), 8.30-8.25 (m, 2H), 8.10 (d, 1H), 7.84-7.75 (m, 3H), 7.71-7.63 (m, 3H).

LCMS (Method C), (M+H$^+$) 417, RT=2.18 min.

N-[5-(2-Amino-[1,2,4]triazolo[1,5-a]pyridin-6-yl)-pyridin-3-yl]-4

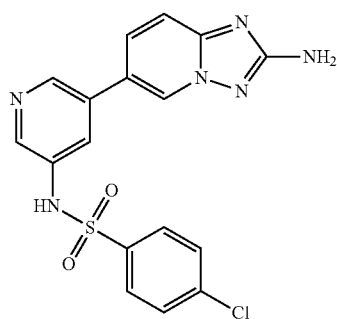 [SMILES: Nc1nc2ccc(-c3cncc(NS(=O)(=O)c4ccc(Cl)cc4)c3)cn2n1]

$^1$H NMR (d$_6$-DMSO) δ 11.22 (br s, 1H), 9.23 (br s, 1H), 8.76 (br s, 1H), 8.38 (br s, 1H), 8.01 (dd, 1H), 7.98 (t, 1H), 7.86 (d, 2H), 7.73 (d, 1H), 7.06 (d, 2H).

LCMS (Method C), (M+H$^+$) 401, RT=2.12 min.

6-(3,4-Dimethoxyphenyl)-8-chloro-[1,2,4]triazolo[1,5-a]pyridine-2-ylamine

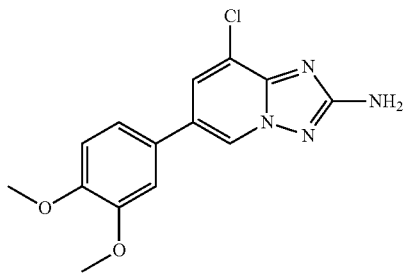 [SMILES: COc1ccc(-c2cc(Cl)c3nc(N)nn3c2)cc1OC]

$^1$H NMR (d$_6$-DMSO) δ 8.83 (s, 1H), 7.91 (s, 1H), 7.24-7.19 (m, 2H), 6.95 (d, 1H), 6.22 (br s, 2H), 3.80 (s, 3H), 3.73 (s, 3H).

N-[5-(2-Amino-[1,2,4]triazolo[1,5-a]pyridin-6-yl)pyridine-3-yl]-3-trifluoromethoxybenzene-sulfonamide HCl

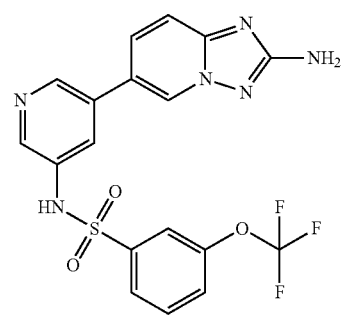 [SMILES: Nc1nc2ccc(-c3cncc(NS(=O)(=O)c4cccc(OC(F)(F)F)c4)c3)cn2n1]

$^1$H NMR (d$_6$-DMSO) δ 9.20 (br s, 1H), 8.75 (d, 1H), 8.33 (d, 1H), 7.97 (dd, 1H), 7.94 (t, 1H), 7.86 (dt, 1H), 7.78 (br s, 1H), 7.75-7.68 (m, 3H).

LCMS (Method C), (M+H$^+$) 451, RT=2.29 min.

N-[5-(2-Amino-[1,2,4]triazolo[1,5-a]pyridin-6-yl)pyridine-3-yl]-C-(2-trifluoromethylphenyl)methane-sulfonamide HCl

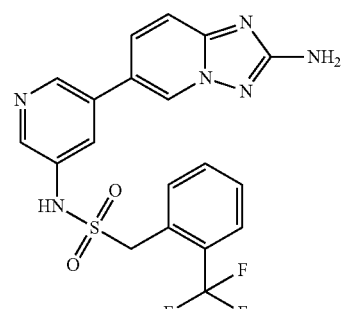

$^1$H NMR (d$_6$-DMSO) δ 10.86 (br s, 1H), 9.23 (br s, 1H), 8.76 (d, 1H), 8.44 (d, 1H), 7.99 (dd, 1H), 7.94 (t, 1H), 7.76-7.66 (m, 4H), 7.57 (t, 1H), 4.85 (s, 2H).

LCMS (Method C), (M+H$^+$) 449, RT=2.14 min.

N-[5-(2-Amino-[1,2,4]triazolo[1,5-a]pyridin-6-yl) pyridine-3-yl]-C-(4-trifluoromethylphenyl)methane- sulfonamide HCl

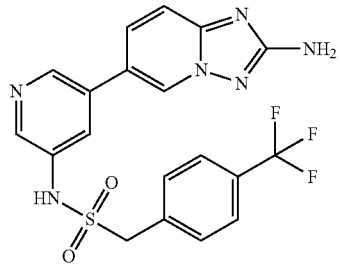 [SMILES: Nc1nc2ccc(-c3cncc(NS(=O)(=O)Cc4ccc(C(F)(F)F)cc4)c3)cn2n1]

$^1$H NMR (d$_6$-DMSO) δ 10.59 (br s, 1H), 9.22 (br s, 1H), 8.74 (d, 1H), 8.40 (d, 1H), 7.96 (dd, 1H), 7.87 (t, 1H), 7.74-7.68 (m, 3H), 7.59 (d, 2H), 4.90 (s, 2H).
LCMS (Method C), (M+H$^+$) 449, RT=2.18 min.

N-[5-(2-Amino-[1,2,4]triazolo[1,5-a]pyridin-6-yl) pyridine-3-yl]-C-(4-chlorophenyl)methanesulfona- mide HCl

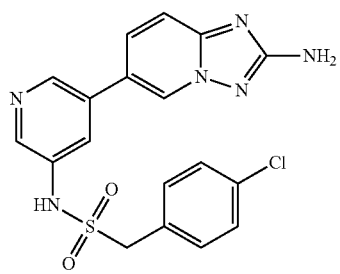 [SMILES: Nc1nc2ccc(-c3cncc(NS(=O)(=O)Cc4ccc(Cl)cc4)c3)cn2n1]

$^1$H NMR (d$_6$-DMSO) δ 10.60 (br s, 1H), 9.21 (br s, 1H), 8.73 (br s, 1H), 8.38 (br s, 1H), 7.95 (dd, 1H), 7.82 (t, 1H), 7.69 (d, 1H), 7.39 (d, 2H), 7.35 (d, 2H), 4.76 (s, 2H).
LCMS (Method C), (M+H$^+$) 415, RT=2.04 min.

N-[5-(2-Amino-[1,2,4]triazolo[1,5-a]pyridin-6-yl)- pyridin-3-yl]-3,5-bis-trifluoromethylbenzene- sulfonamide

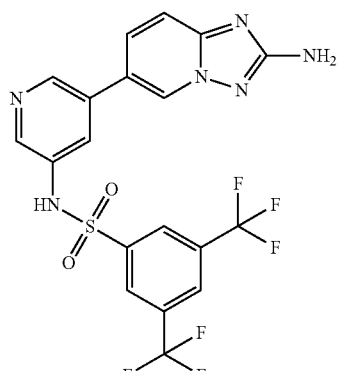

$^1$H NMR (d$_6$-DMSO) δ 10.99 (br s, 1H), 8.95 (d, 1H), 8.73 (d, 1H), 8.53 (br s, 1H), 8.36 (br s, 2H), 8.25 (d, 1H), 7.82 (t, 1H), 7.67 (dd, 1H), 7.46 (dd, 1H), 6.17 (s, 2H).
LCMS (Method A), (M+H$^+$) 503, RT=5.42 min.

5-(2-amino-[1,2,4]triazolo[1,5-a]pyridin-6-yl)-N-(4- (trifluoromethyl)phenyl)pyridine-3-sulfonamide

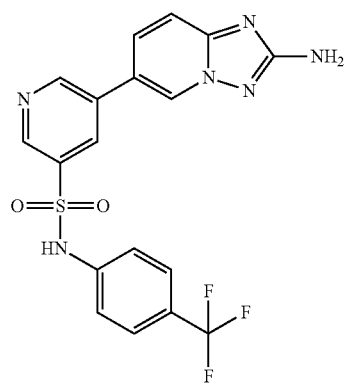 [SMILES: Nc1nc2ccc(-c3cncc(S(=O)(=O)Nc4ccc(C(F)(F)F)cc4)c3)cn2n1]

$^1$H NMR (CD$_3$OD) δ 9.39-9.45 (m, 1H), 9.21-9.31 (m, 2H), 8.75 (d, 1H), 8.30-8.85 (m, 2H), 7.87-7.97 (m, 2H), 7.40-7.61 (m, 2H).
LCMS (method A), (M+H$^+$) 435, Rt=5.13 min 5-(2-amino-[1,2,4]triazolo[1,5-a]pyridin-6-yl)-N-(2- (trifluoromethyl)phenyl)pyridine-3

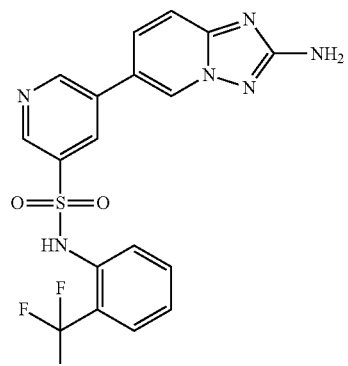

$^1$H NMR (CD$_3$OD and CDCl$_3$) δ 8.59 (s, 2H), 8.39 (d, 2H), 7.94 (t, 1H), 7.69 (dd, 1H), 7.29 (d, 1H), 7.11 (d, 1H), 7.09 (s, 1H), 6.88-6.94 (m, 1H).
LCMS (method A), (M+H$^+$) 435, Rt=4.51 min.

47

5-(2-amino-[1,2,4]triazolo[1,5-a]pyridin-6-yl)-N-(3-(trifluoromethyl)phenyl)pyridine-3-sulfonamide

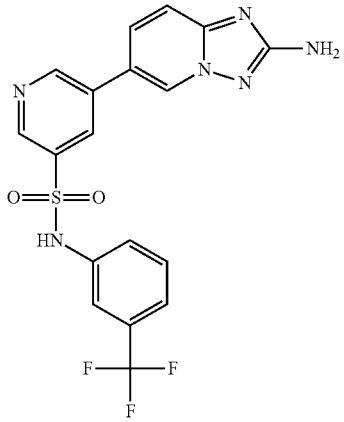 [SMILES: Nc1nc2ccc(-c3cncc(S(=O)(=O)Nc4cccc(C(F)(F)F)c4)c3)cn2n1]

$^1$H NMR (CD$_3$OD) δ 9.20 (br, s, 2H), 9.15 (s, 1H), 8.49 (s, 1H), 8.23 (d, 1H), 7.83 (d, 1H), 7.39-7.49 (m, 4H).
LCMS (method A), (M+H$^+$) 435, Rt=4.98 min.

5-(2-amino-[1,2,4]triazolo[1,5-a]pyridin-6-yl)-N-methyl-N-(3-(trifluoromethyl)phenyl)pyridine-3-sulfonamide

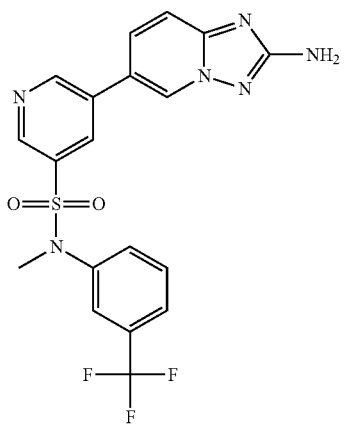 [SMILES: CN(c1cccc(C(F)(F)F)c1)S(=O)(=O)c1cncc(-c2ccc3nc(N)nn3c2)c1]

$^1$H NMR (CD$_3$OD) δ 9.20 (br, d, 1H), 9.19 (br, d, 1H), 8.70 (d, 1H), 8.29 (t, 1H), 8.25 (dd, 1H), 7.85 (d, 1H), 7.66 (d, 1H), 7.58 (t, 1H), 7.54 (br, s, 1H), 4.49 (d, 1H), 3.33 (s, 3H).
LCMS (method A), (M+H$^+$) 449, Rt=5.34 min.

48

5-(2-amino-[1,2,4]triazolo[1,5-a]pyridin-6-yl)-N-(4-(trifluoromethoxy)phenyl)pyridine-3-sulfonamide

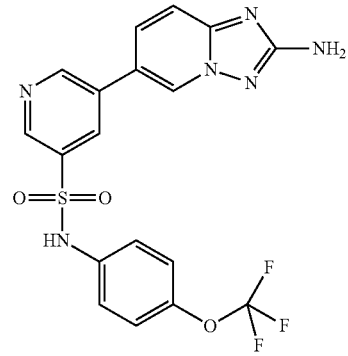 [SMILES: Nc1nc2ccc(-c3cncc(S(=O)(=O)Nc4ccc(OC(F)(F)F)cc4)c3)cn2n1]

$^1$H NMR (CD$_3$OD) δ 9.21 (s, 1H), 9.19 (br, s, 1H), 9.01 (br, s, 1H), 8.58 (s, 1H), 8.27 (d, 1H), 7.86 (d, 1H), 7.27 (d, 2H), 7.19 (d, 2H).
LCMS (method A), (M+H$^+$) 449, Rt=5.34 min.

5-(2-amino-[1,2,4]triazolo[1,5-a]pyridin-6-yl)-N-phenylpyridine-3-sulfonamide

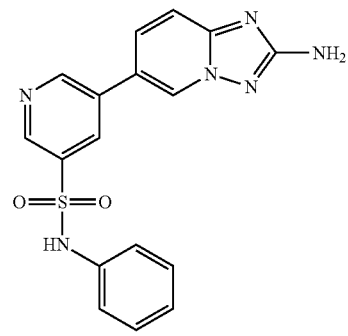 [SMILES: Nc1nc2ccc(-c3cncc(S(=O)(=O)Nc4ccccc4)c3)cn2n1]

$^1$H NMR (CD$_3$OD) δ 9.14 (br, s, 1H), 8.97 (br, s, 1H), 8.50 (t, 1H), 8.23 (dd, 1H), 7.85 (d, 1H), 7.25-7.29 (m, 2H), 7.11-7.17 (m, 3H).
LCMS (method A), (M+H$^+$) 367, Rt=4.06 min.

5-(2-amino-[1,2,4]triazolo[1,5-a]pyridin-6-yl)-N-(3-(trifluoromethoxy)phenyl)pyridine-3-sulfonamide

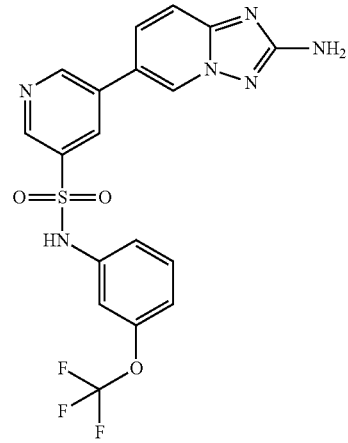 [SMILES: Nc1nc2ccc(-c3cncc(S(=O)(=O)Nc4cccc(OC(F)(F)F)c4)c3)cn2n1]

¹H NMR (d₆-DMSO) δ 10.90 (br, s, 1H), 9.17 (d, 1H), 9.09 (d, 1H), 8.85 (d, 1H), 8.42 (t, 1H), 7.77 (dd, 1H), 7.49 (dd, 1H), 7.37 (t, 1H), 7.15 (dd, 1H), 7.10 (br, s, 1H), 7.02 (d, 1H), 6.21 (s, 2H).

LCMS (method A), (M+H⁺) 451, Rt=2.42 min.

5-(2-amino-[1,2,4]triazolo[1,5-a]pyridin-6-yl)-N-(3-(1,1,2,2-tetrafluoroethoxy)phenyl)pyridine-3-sulfonamide

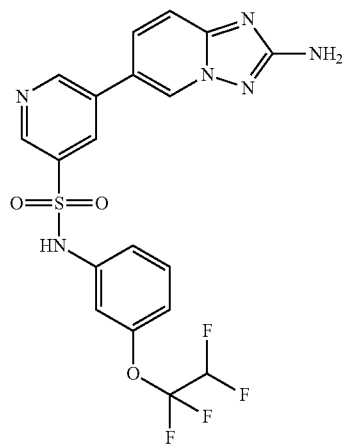 [SMILES: Nc1nc2ccc(-c3cncc(S(=O)(=O)Nc4cccc(OC(F)(F)C(F)F)c4)c3)cn2n1]

¹H NMR (d₆-DMSO) δ 9.11 (d, 1H), 9.06 (br, s, 1H), 8.82-8.84 (m, 1H), 8.37 (t, 1H), 7.75 (dd, 1H), 7.47 (d, 1H), 7.26 (t, 1H), 7.03 (d, 1H), 6.98-7.05 (m, 1H), 6.80 (d, 1H), 6.61-6.88 (m, 1H), 6.20 (s, 2H).

LCMS (method A), (M+H⁺) 483, Rt=5.26 min.

5-(2-amino-[1,2,4]triazolo[1,5-a]pyridin-6-yl)-N-(3-(difluoromethoxy)phenyl)pyridine-3-sulfonamide

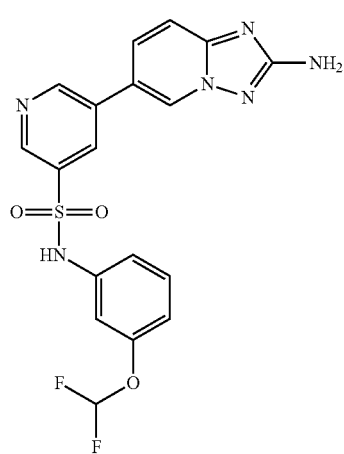 [SMILES: Nc1nc2ccc(-c3cncc(S(=O)(=O)Nc4cccc(OC(F)F)c4)c3)cn2n1]

¹H NMR (d₆-DMSO) δ 9.15 (d, 1H), 9.07-9.08 (m, 1H), 8.85 (d, 1H), 8.41 (t, 1H), 7.77 (dd, 1H), 7.49 (dd, 1H), 7.24-7.28 (m, 1H), 6.96-6.99 (m, 1H), 6.96 (t, 1H), 6.90-6.91 (m, 1H), 6.79 (d, 1H), 6.21 (s, 2H).

LCMS (method A), (M+H⁺) 433, Rt=4.63 min.

5-(2-amino-[1,2,4]triazolo[1,5-a]pyridin-6-yl)-N-(4-(difluoromethoxy)phenyl)pyridine-3-sulfonamide

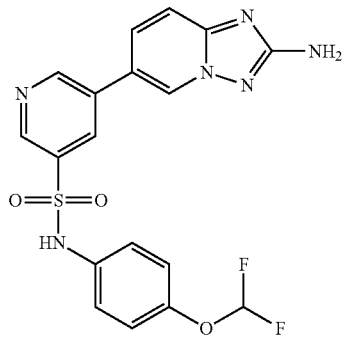 [SMILES: Nc1nc2ccc(-c3cncc(S(=O)(=O)Nc4ccc(OC(F)F)cc4)c3)cn2n1]

¹H NMR (d₆-DMSO) δ 10.5 (br, s, 1H), 9.13 (d, 1H), 9.09 (d, 1H), 8.80 (d, 1H), 8.38 (t, 1H), 7.74 (dd, 1H), 7.10 (t, 1H), 7.03 (d, 1H), 6.90 (t, 1H), 6.21 (s, 2H).

LCMS (method A), (M+H⁺) 433, Rt=4.65 min.

6-(5-(trifluoromethyl)pyridin-3-yl)-[1,2,4]triazolo[1,5-a]pyridin-2-amine

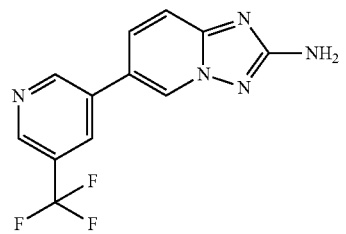 [SMILES: Nc1nc2ccc(-c3cncc(C(F)(F)F)c3)cn2n1]

¹H NMR (CD₃OD) δ 9.17 (d, 1H), 8.95 (dd, 1H), 8.92 (d, 1H), 8.49 (s, 1H), 7.93 (dd, 1H), 7.53 (dd, 1H).

LCMS (method C), (M+H⁺) 280, Rt=1.99 min.

6-(4-isopropoxy-3-methoxyphenyl)-[1,2,4]triazolo[1,5-a]pyridin-2-amine

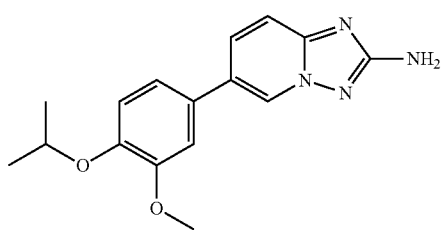 [SMILES: COc1cc(-c2ccc3nc(N)nn3c2)ccc1OC(C)C]

¹H NMR (CD₃OD) δ 8.65 (s, 1H), 7.82 (dd, 1H), 7.43 (d, 1H), 7.24-7.25 (m, 1H), 7.18 (dd, 1H), 7.06 (d, 1H), 4.59-4.65 (m, 1H), 3.93 (s, 3H), 1.36 (s, 3H), 1.35 (s, 3H).

LCMS (method C), (M+H⁺) 299, Rt=2.19 min.

| 51 | 52 |
|---|---|
| 5-(2-amino-[1,2,4]triazolo[1,5-a]pyridine-6-yl)-N-(2-methyl-1-(pyrrolidin-1-yl)propan-2-yl)pyridine-3-sulfonamide | 6-(5-(4-methylpiperizin-1-ylsulfonyl)pyridine-3-yl)-[1,2,4]triazolo[1,5-a]pyridine-2-amine |

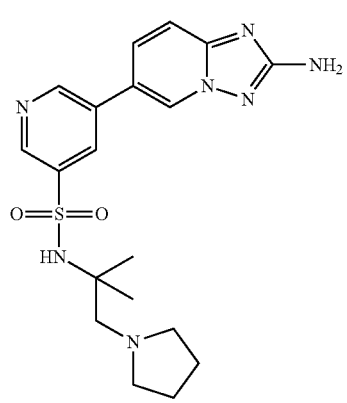 [SMILES: CC(C)(CN1CCCC1)NS(=O)(=O)c1cncc(-c2ccc3nc(N)nn3c2)c1]

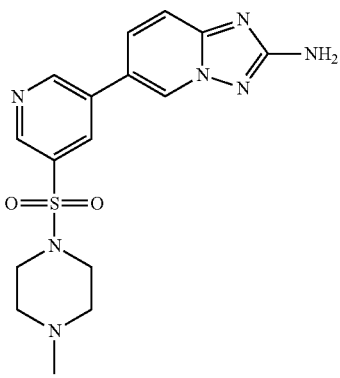

¹H NMR (d₄-MeOH) δ 9.13 (d, 1H), 9.05 (d, 1H), 8.91 (d, 1H), 8.57 (t, 1H), 8.34 (br s, 2H), 7.89 (dd, 1H), 7.52 (d, 1H), 3.57-3.52 (m, 6H), 2.15-2.11 (m, 4H), 1.28 (s, 3H), 1.20 (s, 3H).

LCMS (method C), (M+H⁺) 416, Rt=1.38 min.

¹H NMR (d₄-MeOH) δ 9.16 (d, 1H), 8.94-8.93 (m, 2H), 8.43 (t, 1H), 7.90 (dd, 1H), 7.51 (dd, 1H), 3.17 (br s, 4H), 2.61 (t, 4H), 2.33 (s, 3H).

LCMS (method 42), (M+H⁺) 374, Rt=1.89 min.

6-(5-(4-fluoropiperidin-1-ylsulfonyl)pyridine-3-yl)-[1,2,4]triazolo[1,5-a]pyridine-2-amine 2-(5-(2-amino-[1,2,4]triazolo[1,5-a]pyridine-6-yl)pyridine-3-sulfoamido)-N,N-dimethylacetamide

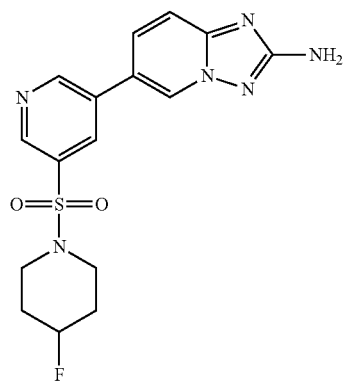 [SMILES: Nc1nc2ccc(-c3cncc(S(=O)(=O)N4CCC(F)CC4)c3)cn2n1]

¹H NMR (d₆-DMSO) δ 9.28 (d, 1H), 9.20 (d, 1H), 8.90 (d, 1H), 8.42 (t, 1H), 7.93 (dd, 1H), 7.49 (d, 1H), 4.84-4.80 (m, 1H), 3.20-3.14 (m, 2H), 3.09-3.03 (m, 2H), 2.00-1.78 (m, 4H).

LCMS (method C), (M+H⁺) 377, Rt=2.01 min.

¹H NMR (d₆-DMSO) δ 9.19 (d, 1H), 9.13 (dd, 1H), 8.92 (d, 1H), 8.53 (t, 1H), 8.00 (br s, 1H), 7.88 (dd, 1H), 7.52 (dd, 1H), 6.20 (br s, 2H), 3.90 (br s, 2H), 2.88 (s, 3H), 2.73 (s, 3H).

LCMS (method 42), (M+H⁺) 376, Rt=1.46 min.

53

5-(2-amino-[1,2,4]triazolo[1,5-a]pyridine-6-yl)-N-(2-(oxoimidazolidin-1-yl)ethyl)pyridine-3-sulfonamide

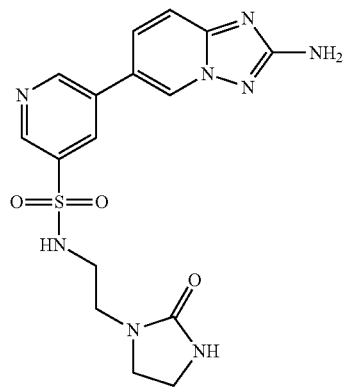 [SMILES: Nc1nc2ccc(-c3cncc(S(=O)(=O)NCCN4CCNC4=O)c3)cn2n1]

$^1$H NMR (d$_6$-DMSO) δ 9.20 (d, 1H), 9.15-9.14 (m, 1H), 8.91 (d, 1H), 8.45 (t, 1H), 7.88 (dd, 1H), 7.50 (d, 1H), 6.31 (br s, 1H), 6.20 (br s, 2H), 3.28 (t, 2H), 3.16-3.08 (m, 4H), 2.97 (t, 2H).

LCMS (method 42), (M+H$^+$) 403, Rt=1.59 min.

5-(2-amino-[1,2,4]triazolo[1,5-a]pyridine-6-yl)-N-(2-(dimethylamino)ethyl)-N-methylpyridine-3-sulfonamide

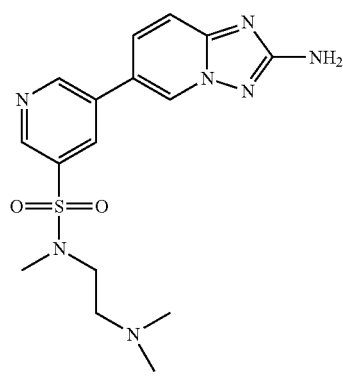 [SMILES: CN(C)CCN(C)S(=O)(=O)c1cncc(-c2ccc3nc(N)nn3c2)c1]

$^1$H NMR (d$_6$-DMSO) δ 9.18 (d, 1H), 9.01 (d, 1H), 8.95-8.94 (m, 1H), 8.52 (t, 1H), 8.42 (br s, 2H), 7.92 (dd, 1H), 7.51 (d, 1H), 3.46 (br t, 2H), 3.24 (br t, 2H), 2.89 (s, 3H), 2.86 (br s, 6H).

LCMS (method 42), (M+H$^+$) 376, Rt=1.92 min.

54

5-(2-amino-[1,2,4]triazolo[1,5-a]pyridine-6-yl)-N-(3-(dimethylamino)propyl)pyridine-3-sulfonamide

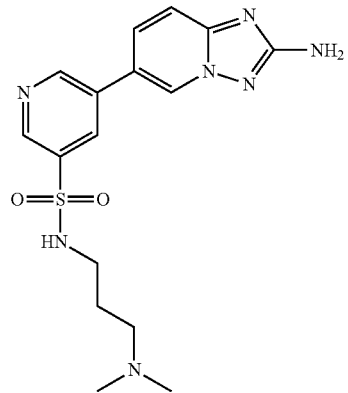 [SMILES: CN(C)CCCNS(=O)(=O)c1cncc(-c2ccc3nc(N)nn3c2)c1]

$^1$H NMR (d$_6$-DMSO) δ 9.22 (d, 1H), 9.15 (br d, 1H), 8.90 (d, 1H), 8.44 (t, 1H), 8.26 (br s, 1H), 7.87 (dd, 1H), 7.51 (d, 1H), 6.21 (br s, 2H), 2.86 (t, 2H), 2.18 (t, 2H), 2.05 (s, 6H), 1.51 (pentet, 2H).

LCMS (method 42), (M+H$^+$) 376, Rt=1.82 min.

5-(2-amino-[1,2,4]triazolo[1,5-a]pyridine-6-yl)-N-butyl-N-methylpyridine-3-sulfonamide

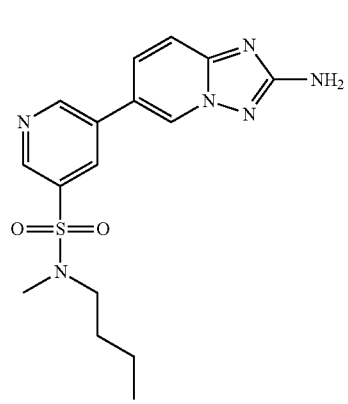 [SMILES: CCCCN(C)S(=O)(=O)c1cncc(-c2ccc3nc(N)nn3c2)c1]

$^1$H NMR (d$_6$-DMSO) δ 9.45 (br s, 1H), 9.29 (d, 1H), 8.98 (d, 1H), 8.51 (t, 1H), 8.26 (dd, 1H), 7.74 (d, 1H), 3.06 (t, 2H), 2.76 (s, 3H), 1.48 (pentet, 2H), 1.29 (sextet, 2H), 0.89 (t, 3H).

LCMS (method C), (M+H$^+$) 361, Rt=2.28 min.

55

5-(2-amino-[1,2,4]triazolo[1,5-a]pyridine-6-yl)-N-isopentylpyridine-3-sulfonamide

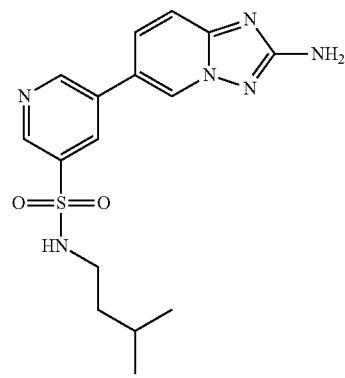 [SMILES: CC(C)CCNS(=O)(=O)c1cncc(-c2ccc3nc(N)nn3c2)c1]

$^1$H NMR (d$_6$-DMSO) δ 9.37 (br s, 1H), 9.24 (d, 1H), 8.97 (d, 1H), 8.53 (t, 1H), 8.17 (dd, 1H), 7.92 (t, 1H), 7.71 (d, 1H), 2.85 (q, 2H), 1.60-1.52 (m, 1H), 1.30-1.23 (m, 2H), 0.79 (d, 6H).

LCMS (method C), (M+H$^+$) 361, Rt=2.22 min.

5-(2-amino-[1,2,4]triazolo[1,5-a]pyridine-6-yl)-N-(cyclopropylmethyl)pyridine-3-sulfonamide

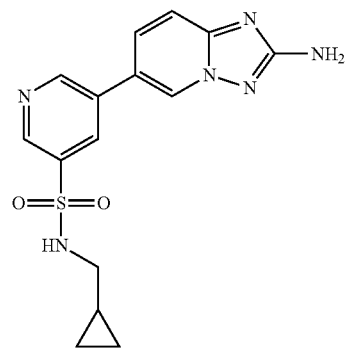 [SMILES: Nc1nc2ccc(-c3cncc(S(=O)(=O)NCC4CC4)c3)cn2n1]

$^1$H NMR (d$_6$-DMSO) δ 9.38 (br s, 1H), 9.23 (d, 1H), 8.98 (d, 1H), 8.55 (t, 1H), 8.20 (dd, 1H), 8.13 (t, 1H), 7.74 (d, 1H), 2.77 (t, 2H), 0.85-0.79 (m, 1H), 0.36-0.31 (m, 2H), 0.12-0.08 (m, 2H).

LCMS (method C), (M+H$^+$) 345, Rt=1.94 min.

56

6-(5-isoindolin-2-ylsulfonyl)pyridine-3-yl)-[1,2,4]triazolo[1,5-a]pyridin-2-amine

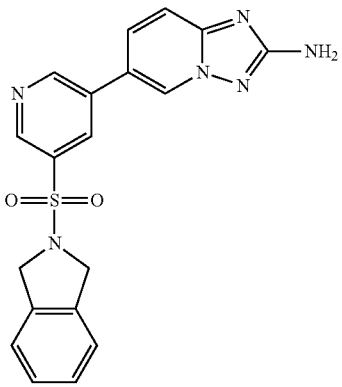 [SMILES: Nc1nc2ccc(-c3cncc(S(=O)(=O)N4Cc5ccccc5C4)c3)cn2n1]

$^1$H NMR (d$_6$-DMSO) δ 9.35 (br s, 1H), 9.24 (d, 1H), 9.05 (d, 1H), 8.54 (t, 1H), 8.14 (dd, 1H), 7.66 (d, 1H), 7.24-7.23 (m, 4H), 4.72 (s, 4H).

LCMS (method C), (M+H$^+$) 393, Rt=2.28 min.

6-(5-piperazin-1-ylsulfonyl)pyridine-3-yl)-[1,2,4]triazolo[1,5-a]pyridin-2-amine

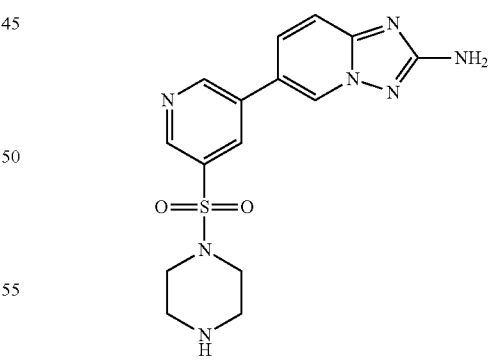

$^1$H NMR (d$_6$-DMSO) δ 9.29 (d, 1H), 9.22-9.20 (m, 1H), 8.86 (d, 1H), 8.39 (t, 1H), 8.22 (br s, 1H), 7.93 (dd, 1H), 7.49 (d, 1H), 6.20 (br s, 2H), 2.91 (t, 4H), 2.74 (t, 4H).

LCMS (method C), (M+H$^+$) 360, Rt=1.27 min.

5-(2-amino-[1,2,4]triazolo[1,5-a]pyridin-6-yl)-N-benzyl-N-methylpyridine-3-sulfonamide

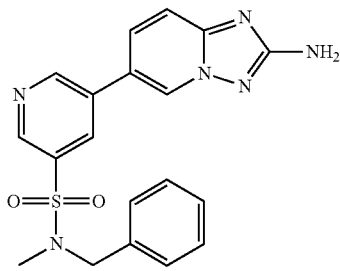 [SMILES: CN(Cc1ccccc1)S(=O)(=O)c1cncc(-c2ccc3nc(N)nn3c2)c1]

$^1$H NMR (d$_6$-DMSO) δ 9.29 (d, 1H), 9.24-9.23 (m, 1H), 8.99 (d, 1H), 8.52 (t, 1H), 7.96 (dd, 1H), 7.51 (dd, 1H), 7.40-7.29 (m, 5H), 6.20 (br s, 2H), 4.29 (s, 2H), 2.67 (s, 3H).
LCMS (method C), (M+H$^+$) 395, Rt=2.36 min.

5-(2-amino-[1,2,4]triazolo[1,5-a]pyridin-6-yl)-N-((2,4-dimethyloxazol-5-yl)methyl)pyridine-3-sulfonamide

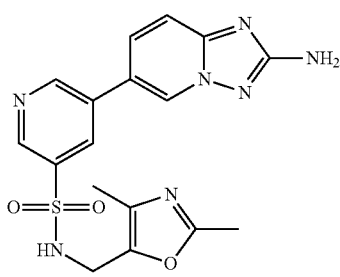 [SMILES: Cc1nc(C)c(CNS(=O)(=O)c2cncc(-c3ccc4nc(N)nn4c3)c2)o1]

$^1$H NMR (d$_6$-DMSO) δ 9.15 (d, 1H), 9.11-9.10 (m, 1H), 8.79 (d, 1H), 8.33 (t, 1H), 7.84 (dd, 1H), 7.53 (dd, 1H), 6.22 (br s, 2H), 3.94 (s, 2H), 2.09 (s, 3H), 2.04 (s, 3H).
LCMS (method C), (M+H$^+$) 400, Rt=1.86 min.

5-(2-amino-[1,2,4]triazolo[1,5-a]pyridin-6-yl)-N-benzyl-N-butylpyridine-3-sulfonamide

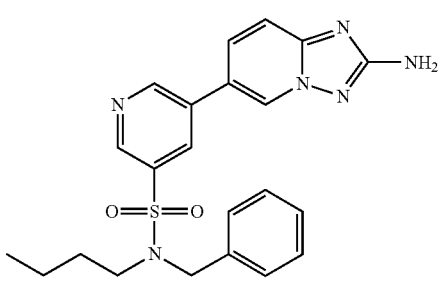 [SMILES: CCCCN(Cc1ccccc1)S(=O)(=O)c1cncc(-c2ccc3nc(N)nn3c2)c1]

$^1$H NMR (d$_6$-DMSO) δ 9.25 (d, 1H), 9.21-9.20 (m, 1H), 8.99 (d, 1H), 8.52 (t, 1H), 7.93 (dd, 1H), 7.49 (d, 1H), 7.35 (d, 4H), 7.31-7.25 (m, 1H), 6.20 (s, 2H), 4.44 (s, 2H), 3.18 (t, 2H), 1.28-1.20 (m, 2H), 1.13-1.04 (m, 2H), 0.68 (t, 3H)
LCMS (method C), (M+H$^+$) 437, Rt=2.70 min.

6-(5-(3,4-dihydroisoquinolin-2(1H)-ylsulfonyl)pyridine-3-yl-[1,2,4]triazolo[1,5-a]pyridin-amine

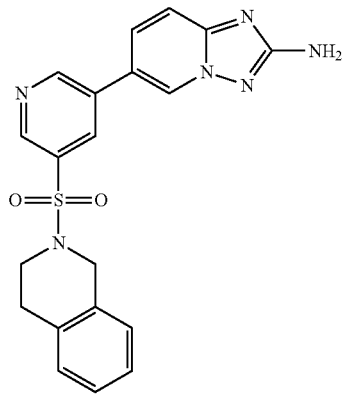 [SMILES: Nc1nc2ccc(-c3cncc(S(=O)(=O)N4CCc5ccccc5C4)c3)cn2n1]

$^1$H NMR (d$_6$-DMSO) δ 9.23 (d, 1H), 9.15-9.14 (m, 1H), 8.96 (d, 1H), 8.46 (t, 1H), 7.86 (dd, 1H), 7.48 (d, 1H), 7.19-7.08 (m, 4H), 6.20 (s, 2H), 4.39 (s, 2H), 3.48 (t, 2H), 2.84 (t, 2H).
LCMS (method C), (M+H$^+$) 407, Rt=2.35 min.

5-(2-amino-[1,2,4]triazolo[1,5-a]pyridin-6-yl)-N-(2,3-dichlorobenzyl)-N-methylpyridine-3-sulfonamide

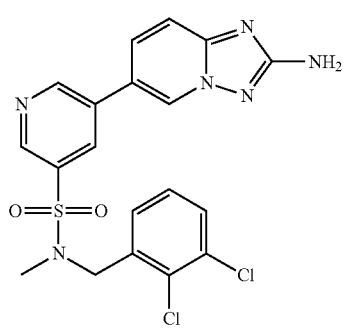 [SMILES: CN(Cc1cccc(Cl)c1Cl)S(=O)(=O)c1cncc(-c2ccc3nc(N)nn3c2)c1]

$^1$H NMR (d$_6$-DMSO) δ 9.30 (d, 1H), 9.25-9.24 (m, 1H), 9.00 (d, 1H), 8.56 (t, 1H), 7.97 (dd, 1H), 7.63 (dd, 1H), 7.51-7.41 (m, 3H), 6.21 (br s, 2H), 4.46 (s, 2H), 2.75 (s, 3H).
LCMS (method C), (M+H$^+$) 464, Rt=2.60 min.

5-(2-amino-[1,2,4]triazolo[1,5-a]pyridin-6-yl)-N-cyclopropyl-N-(2-fluorobenzyl)pyridine-3-sulfonamide

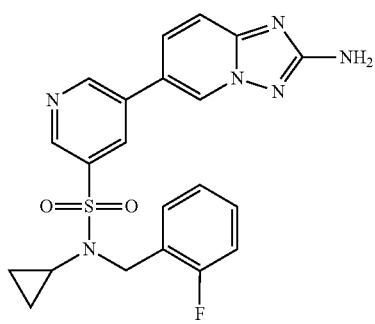 [SMILES: Nc1nc2ccc(-c3cncc(S(=O)(=O)N(Cc4ccccc4F)C4CC4)c3)cn2n1]

¹H NMR (d₆-DMSO) δ 9.27 (d, 1H), 9.19-9.18 (m, 1H), 8.97 (d, 1H), 8.43 (t, 1H), 7.90 (dd, 1H), 7.50 (dd, 1H), 7.46 (td, 1H), 7.36-7.31 (m, 1H), 7.22-7.14 (m, 2H), 6.20 (br s, 2H), 4.51 (s, 2H), 2.26-2.19 (m, 1H), 0.68-0.64 (m, 2H), 0.61-0.57 (m, 2H).

LCMS (method C), (M+H⁺) 439, Rt=2.50 min.

5-(2-amino-[1,2,4]triazolo[1,5-a]pyridin-6-yl)-N-(2-phenylpropan-2-yl)pyridine-3-sulfonamide

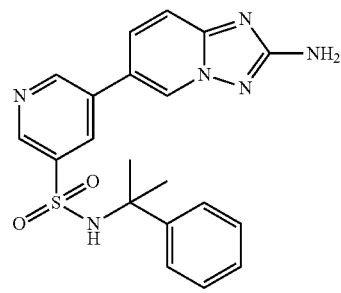 [SMILES: CC(C)(NS(=O)(=O)c1cncc(-c2ccc3nc(N)nn3c2)c1)c1ccccc1]

¹H NMR (d₆-DMSO) δ 8.98 (d, 1H), 8.96 (d, 1H), 8.57 (d, 1H), 8.33 (brs, 1H), 7.88 (dd, 1H), 7.69 (dd, 1H), 7.50 (d, 1H), 7.22 (d, 2H), 6.98 (t, 2H), 6.92 (t, 1H), 6.21 (s, 2H), 1.60 (s, 6H).

LCMS (method C), (M+H⁺) 409, Rt=2.18 min.

5-(2-amino-[1,2,4]triazolo[1,5-a]pyridin-6-yl)-N-(2-(4-fluorophenyl)propan-2

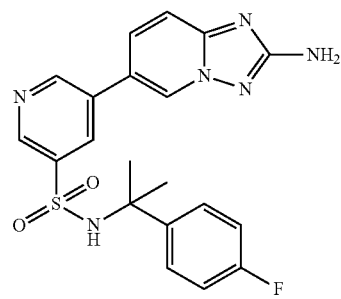 [SMILES: CC(C)(NS(=O)(=O)c1cncc(-c2ccc3nc(N)nn3c2)c1)c1ccc(F)cc1]

¹H NMR (CD₃OD) δ 8.92 (d, 1H), 8.77 (d, 1H), 8.65 (d, 1H), 7.83 (t, 1H), 7.76 (dd, 1H), 7.52 (d, 1H), 7.22-7.26 (m, 2H), 6.69-6.73 (m, 2H), 1.71 (s, 6H).

LCMS (method C), (M+H⁺) 427, Rt=2.21 min.

5-(2-amino-[1,2,4]triazolo[1,5-a]pyridin-6-yl)-N-(4-fluorobenzyl)pyridine-3-sulfonamide

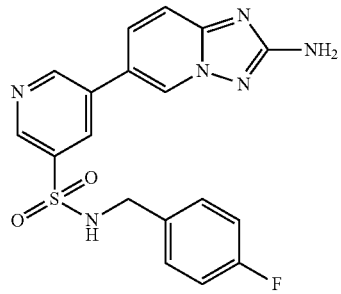 [SMILES: Nc1nc2ccc(-c3cncc(S(=O)(=O)NCc4ccc(F)cc4)c3)cn2n1]

¹H NMR (d₆-DMSO) δ 9.16 (d, 1H), 9.10 (d, 1H), 8.86 (d, 1H), 8.47 (brs, 1H), 8.32 (t, 1H), 7.81 (dd, 1H), 7.51 (d, 1H), 7.26 (dd, 2H), 7.04 (dd, 2H), 6.21 (brs, 2H), 4.13 (s, 2H).

LCMS (method C), (M+H⁺) 399, Rt=2.12 min.

5-(2-amino-[1,2,4]triazolo[1,5-a]pyridin-6-yl)-N,N-diethylpyridine-3-sulfonamide

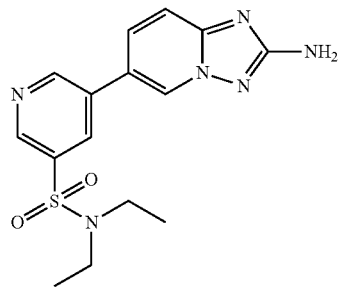 [SMILES: CCN(CC)S(=O)(=O)c1cncc(-c2ccc3nc(N)nn3c2)c1]

¹H NMR (d₆-DMSO) δ 9.23 (d, 1H), 9.21 (d, 1H), 8.94 (d, 1H), 8.48 (t, 1H), 7.94 (dd, 1H), 7.49 (d, 1H), 6.20 (s, 2H), 3.27 (q, 4H), 1.09 (t, 6H).

LCMS (method C), (M+H⁺) 347, Rt=2.07 min.

5-(2-amino-[1,2,4]triazolo[1,5-a]pyridin-6-yl)-N-(1,1,1-trifluoro-2-methylpropan-2-yl)pyridine-3-sulfonamide

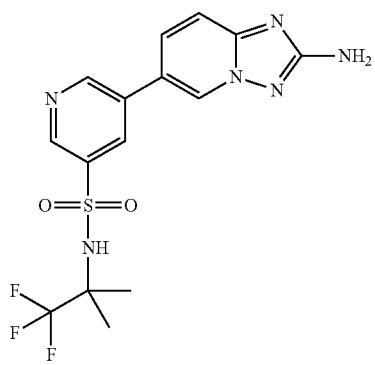 [SMILES: CC(C)(NS(=O)(=O)c1cncc(-c2ccc3nc(N)nn3c2)c1)C(F)(F)F]

61

¹H NMR (CD₃OD) δ 9.30 (s, 2H), 9.20 (s, 1H), 8.81 (s, 1H), 8.38 (d, 1H), 7.91 (d, 1H), 1.53 (s, 6H).
LCMS (method A), (M+H⁺) 401, Rt=7.48 min.

5-(2-amino-[1,2,4]triazolo[1,5-a]pyridin-6-yl)pyridine-3-sulfonamide

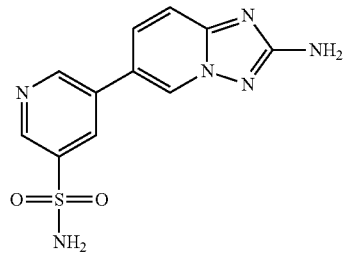 [SMILES: Nc1nc2ccc(-c3cncc(S(N)(=O)=O)c3)cn2n1]

¹H NMR (CD₃OD) δ 9.29 (s, 1H), 9.18 (d, 2H), 8.73 (t, 1H), 8.38 (dd, 1H), 7.89 (d, 1H).
LCMS (method A), (M+H⁺) 291, Rt=5.02 min.

5-(2-amino-[1,2,4]triazolo[1,5-a]pyridin-6-yl)-N-butylpyridine-3-sulfonamide

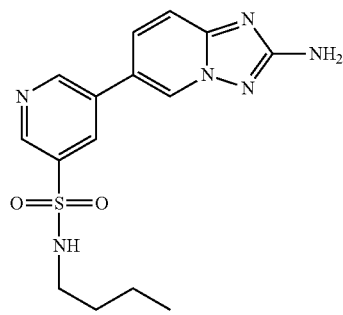 [SMILES: CCCCNS(=O)(=O)c1cncc(-c2ccc3nc(N)nn3c2)c1]

¹H NMR (CD₃OD) δ 9.36 (br, s, 1H), 9.29 (br, s, 2H), 8.90 (br, s, 1H), 8.45 (br, s, 1H), 7.93 (br, s, 1H). 7.35-7.84 (br, m, 1H), 3.03 (br, m, 2H), 1.51 (br, m, 2H), 1.37 (br, m, 1H), 0.89 (m, 1H).
LCMS (method A), (M+H⁺) 347, Rt=7.38 min.

6-(5-(morpholinosulfonyl)pyridin-3-yl)-[1,2,4]triazolo[1,5-a]pyridin-2-amine

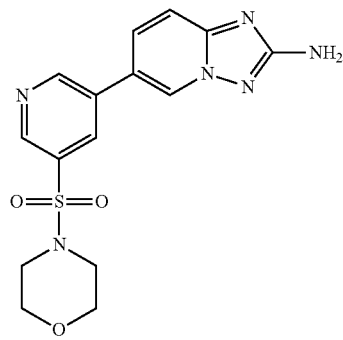 [SMILES: Nc1nc2ccc(-c3cncc(S(=O)(=O)N4CCOCC4)c3)cn2n1]

62

¹H NMR (CD₃OD, CDCl₃) δ 9.26 (s, 1H), 9.10 (s, 1H), 8.93 (s, 1H), 8.47 (s, 1H), 7.94 (d, 1H). 7.71 (d, 1H), 3.95 (m, 4H), 3.28 (m, 4H), 1.37 (br, m, 1H).
LCMS (method A), (M+H⁺) 361, Rt=6.33 min.

5-(2-amino-[1,2,4]triazolo[1,5-a]pyridin-6-yl)-N-(3,3,3-trifluoropropyl)pyridine-3-sulfonamide

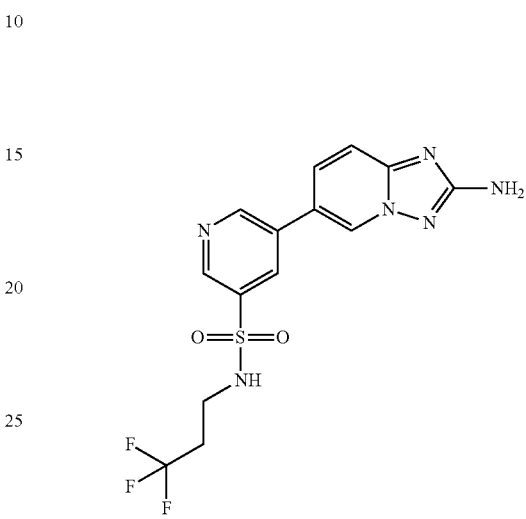

¹H NMR (d₆-DMSO) δ 9.36 (s, 1H), 9.26 (s, 1H), 8.98 (s, 1H), 8.55 (s, 1H), 8.31 (t, 1H). 8.15 (d, 1H), 7.70 (d, 1H), 3.56 (s, 2H), 3.07-3.12 (m, 2H).
LCMS (method A), (M+H⁺) 387, Rt=7.28 min.

5-(2-amino-[1,2,4]triazolo[1,5-a]pyridin-6-yl)-N,N-dimethylpyridine-3-sulfonamide

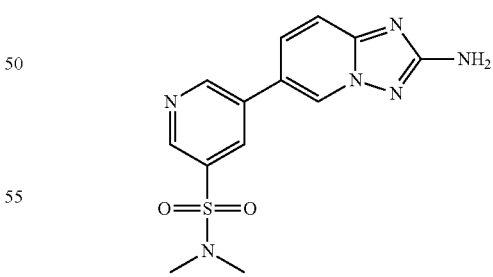

¹H NMR (d₆-DMSO) δ 9.28 (d, 1H), 9.21-9.21 (m, 1H), 8.90 (d, 1H), 8.42 (t, 1H), 7.92 (dd, 1H). 7.49 (dm, 1H), 6.20 (s, 2H), 2.72 (s, 6H).
LCMS (method A), (M+H⁺) 319, Rt=6.34 min.

63

5-(2-amino-[1,2,4]triazolo[1,5-a]pyridin-6-yl)-N-neopentylpyridine-3-sulfonamide

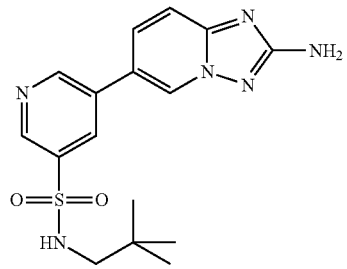 [SMILES: CC(C)(C)CNS(=O)(=O)c1cncc(-c2ccc3nc(N)nn3c2)c1]

$^1$H NMR (d$_6$-DMSO) δ 9.21 (m, 1H), 9.15 (s, 1H), 8.92 (m, 1H), 8.47 (m, 1H), 7.89 (dm, 1H). 7.81 (br, s, 1H), 7.51 (d, 1H), 6.21 (s, 2H), 2.59 (s, 2H), 0.85 (s, 9H).
LCMS (method B), (M+H$^+$) 361, Rt=2.22 min.

5-(2-amino-[1,2,4]triazolo[1,5-a]pyridin-6-yl)-N-cyclopentylpyridine-3-sulfonamide

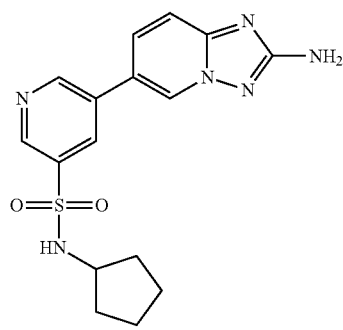 [SMILES: Nc1nc2ccc(-c3cncc(S(=O)(=O)NC4CCCC4)c3)cn2n1]

$^1$H NMR (CD$_3$OD, CDCl$_3$) δ 9.02 (d, 1H), 8.99 (d, 1H), 8.77-8.78 (m, 1H), 8.44 (t, 1H), 8.11 (s, 1H), 7.80 (dd, 1H), 7.51 (dd, 1H), 3.56-3.67 (m, 1H), 1.78 (m, 2H), 1.65 (m. 2H), 1.49 (m, 2H) 1.39 (m, 2H).
LCMS (method A), (M+H$^+$) 359, Rt=7.36 min.

5-(2-amino-[1,2,4]triazolo[1,5-a]pyridin-6-yl)-N-(3,4-dichlorobenzyl)pyridine-3-sulfonamide

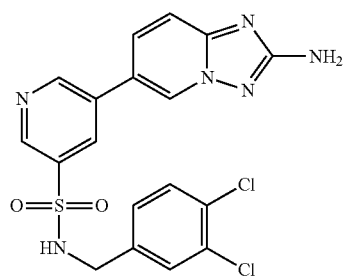 [SMILES: Nc1nc2ccc(-c3cncc(S(=O)(=O)NCc4ccc(Cl)c(Cl)c4)c3)cn2n1]

$^1$H NMR (CD$_3$OD) δ 9.23 (d, 1H), 9.10 (d, 1H), 8.99 (d, 1H), 8.34 (t, 1H), 8.30 (dd, 1H), 7.88 (d, 1H), 7.32-7.36 (m, 2H), 7.15 (dd, 1H), 4.26 (s, 2H).
LCMS (method A), (M+H$^+$) 449, Rt=8.44 min.

64

3-(2-amino-[1,2,4]triazolo[1,5-a]pyridin-6-yl)-N-(2-(dimethylamino)ethyl)benzenesulfonamide

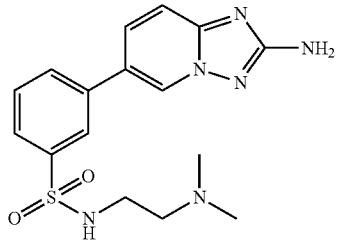 [SMILES: CN(C)CCNS(=O)(=O)c1cccc(-c2ccc3nc(N)nn3c2)c1]

$^1$H NMR (d$_6$-DMSO) δ 8.99 (br s, 1H), 8.13 (s, 1H), 8.02 (d, 1H), 7.83-7.78 (m, 2H), 7.71-7.67 (m, 1H), 7.59 (br s, 1H), 7.50 (d, 1H), 6.16 (br s, 2H), 2.89-2.85 (m, 2H), 2.27-2.23 (m, 2H), 2.05 (s, 6H).
LCMS (method 31), (M+H$^+$) 361, Rt=1.27 min.

3-(2-amino-[1,2,4]triazolo[1,5-a]pyridin-6-yl)-N-(2-(dimethylamino)ethyl)-N-methylbenzenesulfonamide

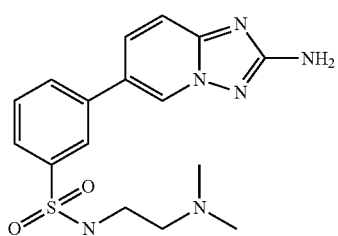

$^1$H NMR (d$_6$-DMSO) δ 9.04 (s, 1H), 8.08-8.04 (m, 2H), 7.84 (dd, 1H), 7.78 (ddd, 1H), 7.75-7.71 (m, 1H), 7.47 (d, 1H), 6.16 (s, 2H), 3.12 (t, 2H), 2.78 (s, 3H), 2.52-2.50 (m, 2H), 2.15 (s, 6H).
LCMS (method B), (M+H$^+$) 375, Rt=1.41 min.

3-(2-amino-[1,2,4]triazolo[1,5-a]pyridin-6-yl)-N-tert-butylbenzenesulfonamide

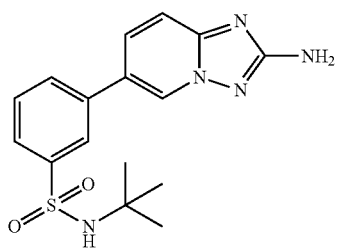 [SMILES: CC(C)(C)NS(=O)(=O)c1cccc(-c2ccc3nc(N)nn3c2)c1]

$^1$H NMR (d$_6$-DMSO) δ 9.12 (br s, 1H), 8.17 (s, 1H), 8.05-7.95 (m, 2H), 7.86 (d, 1H), 7.69 (t, 1H), 7.65-7.59 (m, 2H), 1.11 (s, 9H).
LCMS (method B), (M+H$^+$) 346, Rt=2.19 min.

65

2-(3-(2-amino-[1,2,4]triazolo[1,5-a]pyridin-6-yl)phenylsulfonamido)acetic acid

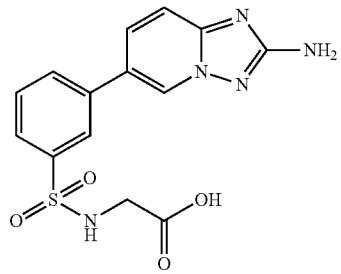 [SMILES: Nc1nc2ccc(-c3cccc(S(=O)(=O)NCC(=O)O)c3)cn2n1]

¹H NMR (d₆-DMSO) δ 8.99 (s, 1H), 8.13 (s, 1H), 7.99 (d, 1H), 7.83-7.77 (m, 2H), 7.68-7.64 (m, 2H), 7.47 (d, 1H), 6.16 (s, 2H), 3.54 (s, 2H).

LCMS (method B), (M+H⁺) 348, Rt=1.73 min.

3-(2-amino-[1,2,4]triazolo[1,5-a]pyridin-6-yl)-N-(3-(dimethylamino)propyl)benzenesulfonamide

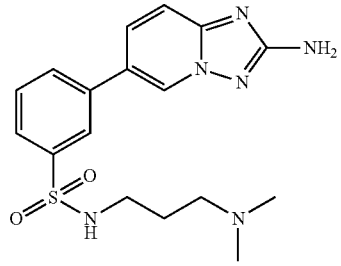 [SMILES: CN(C)CCCNS(=O)(=O)c1cccc(-c2ccc3nc(N)nn3c2)c1]

¹H NMR (d₆-DMSO) δ 8.99 (s, 1H), 8.09 (s, 1H), 8.03 (d, 1H), 7.84-7.77 (m, 2H), 7.72-7.68 (m, 1H), 7.49 (d, 1H), 6.16 (s, 2H), 2.80 (m, 2H), 2.14 (m, 2H), 2.02 (s, 6H), 1.49 (m, 2H).

LCMS (method B), (M+H⁺) 375, Rt=1.35 min.

6-(5-chloropyridin-3-yl)-[1,2,4]triazolo[1,5-a]pyridin-2-amine

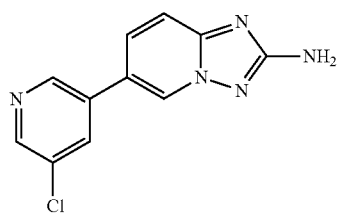 [SMILES: Nc1nc2ccc(-c3cncc(Cl)c3)cn2n1]

¹H NMR (d₆-DMSO) δ 9.13 (s, 1H), 8.95 (s, 1H), 8.63 (s, 1H), 8.37 (s, 1H), 7.89 (d, 1H), 7.49 (d, 1H), 6.18 (s, 2H).

LCMS (method D), (M+H⁺) 246, Rt=1.66 min.

66

5-(2-amino-[1,2,4]triazolo[1,5-a]pyridin-6-yl)-N-cyclopropylpyridine-3-sulfonamide

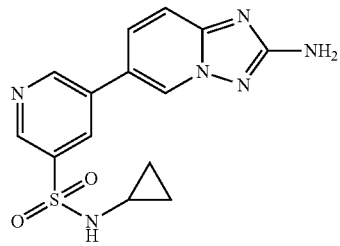 [SMILES: Nc1nc2ccc(-c3cncc(S(=O)(=O)NC4CC4)c3)cn2n1]

¹H NMR (d₆-DMSO) δ 9.24 (s, 1H), 9.16 (s, 1H), 8.93 (s, 1H), 8.45 (s, 1H), 8.17 (s, 1H), 7.87 (d, 1H), 7.51 (d, 1H), 6.21 (s, 2H), 2.29-2.17 (m, 1H), 0.56-0.49 (m, 2H), 0.43-0.36 (m, 2H).

LCMS (method D), (M+H⁺) 331, Rt=1.78 min.

6-(5-(pyrrolidin-1-ylsulfonyl)pyridin-3-yl)-[1,2,4]triazolo[1,5-a]pyridin-2-amine

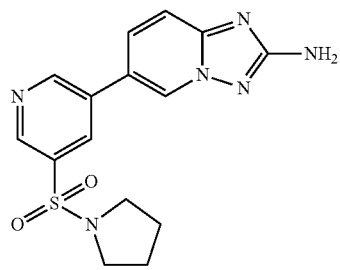 [SMILES: Nc1nc2ccc(-c3cncc(S(=O)(=O)N4CCCC4)c3)cn2n1]

¹H NMR (d₆-DMSO) δ 9.27-9.26 (m, 1H), 9.20 (s, 1H), 8.96-8.95 (m, 1H), 8.46-8.45 (m, 1H), 7.94 (d, 1H), 7.49 (d, 1H), 6.20 (s, 2H), 3.29-3.26 (m, 4H), 1.73-1.67 (m, 4H).

LCMS (method D), (M+H⁺) 345, Rt=2.02 min.

5-(2-amino-[1,2,4]triazolo[1,5-a]pyridin-6-yl)-N-tert-butyl-N-methylpyridine-3-sulfonamide

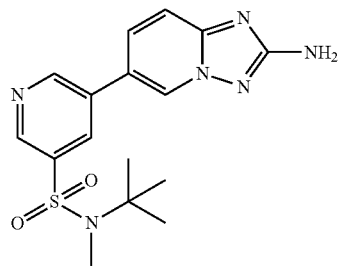 [SMILES: CN(C(C)(C)C)S(=O)(=O)c1cncc(-c2ccc3nc(N)nn3c2)c1]

¹H NMR (d₆-DMSO) δ 9.21-9.20 (m, 1H), 9.18-9.17 (m, 1H), 8.98-8.95 (m, 1H), 8.46-8.39 (m, 1H), 7.91 (d, 1H), 7.46 (d, 1H), 6.20 (s, 2H), 2.97 (s, 3H), 1.31 (s, 9H).

LCMS (method D), (M+H⁺) 361, Rt=2.22 min.

6-(5-(piperidin-1-ylsulfonyl)pyridin-3-yl)-[1,2,4]triazolo[1,5-a]pyridin-2-amine

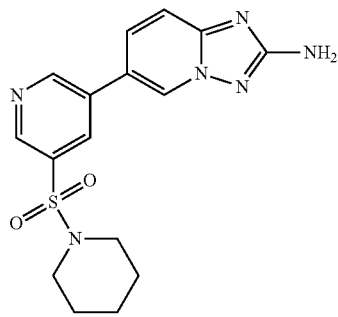 [SMILES: Nc1nc2ccc(-c3cncc(S(=O)(=O)N4CCCCC4)c3)cn2n1]

¹H NMR (d₆-DMSO) δ 9.30-9.28 (m, 1H), 9.21-9.20 (m, 1H), 8.86 (s, 1H), 8.43-8.39 (m, 1H), 8.00-7.83 (m, 1H), 7.53-7.48 (m, 1H), 6.20 (s, 2H), 3.06-2.91 (m, 4H), 1.63-1.47 (m, 4H), 1.42-1.33 (m, 2H).

LCMS (method D), (M+H⁺) 359, Rt=2.20 min.

5-(2-amino-[1,2,4]triazolo[1,5-a]pyridin-6-yl)-N-isobutylpyridine-3-sulfonamide

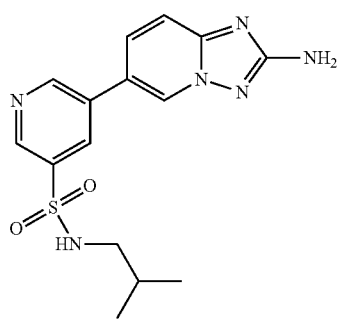 [SMILES: CC(C)CNS(=O)(=O)c1cncc(-c2ccc3nc(N)nn3c2)c1]

¹H NMR (d₆-DMSO) δ 9.22-9.21 (m, 1H), 9.16-9.15 (m, 1H), 8.91-8.90 (m, 1H), 8.46-8.45 (m, 1H), 7.89-7.86 (m, 2H), 7.53-7.49 (m, 1H), 6.20 (s, 2H), 2.71-2.62 (m, 2H), 1.72-1.55 (m, 1H), 0.83 (d, 6H).

LCMS (method D), (M+H⁺) 347, Rt=2.12 min.

5-(2-amino-[1,2,4]triazolo[1,5-a]pyridin-6-yl)-N-isopropylpyridine-3-sulfonamide

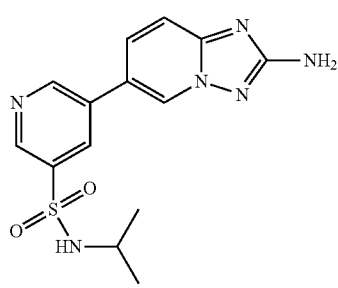 [SMILES: CC(C)NS(=O)(=O)c1cncc(-c2ccc3nc(N)nn3c2)c1]

¹H NMR (d₆-DMSO) δ 9.22-9.21 (m, 1H), 9.16-9.15 (m, 1H), 8.93-8.92 (m, 1H), 8.48-8.47 (m, 1H), 7.88-7.86 (m, 2H), 7.53-7.50 (m, 1H), 6.21 (s, 2H), 4.15-4.11 (m, 1H), 0.98 (d, 6H).

LCMS (method D), (M+H⁺) 333, Rt=1.92 min.

5-(2-amino-[1,2,4]triazolo[1,5-a]pyridin-6-yl)-N-(2,3-dichlorobenzyl)pyridine-3-sulfonamide

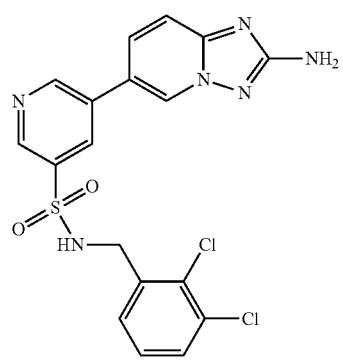 [SMILES: Nc1nc2ccc(-c3cncc(S(=O)(=O)NCc4cccc(Cl)c4Cl)c3)cn2n1]

¹H NMR (d₆-DMSO) δ 9.17-9.16 (m, 1H), 9.10 (s, 1H), 8.85-8.80 (m, 1H), 8.62 (br s, 1H), 8.36-8.35 (m, 1H), 7.83-7.81 (m, 1H), 7.53-7.40 (m, 3H), 7.29-7.25 (m, 1H), 6.22 (s, 2H), 4.27 (s, 2H).

LCMS (method B), (M+H⁺) 449, Rt=2.28 min.

5-(2-amino-[1,2,4]triazolo[1,5-a]pyridin-6-yl)-N-propylpyridine-3-sulfonamide

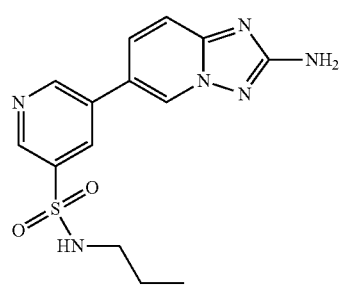 [SMILES: CCCNS(=O)(=O)c1cncc(-c2ccc3nc(N)nn3c2)c1]

¹H NMR (d₆-DMSO) δ 9.22-9.21 (m, 1H), 9.16-9.15 (m, 1H), 8.92-8.91 (m, 1H), 8.45-8.44 (m, 1H), 7.89-7.86 (m, 2H), 7.52-7.50 (m, 1H), 6.21 (s, 2H), 2.82-2.79 (m, 2H), 1.43-1.38 (m, 2H), 0.83-0.80 (t, 3H).

LCMS (method B), (M+H⁺) 333, Rt=1.91 min.

5-(2-amino-[1,2,4]triazolo[1,5-a]pyridin-6-yl)-N-(2,2,2-trifluoroethyl)pyridine-3-sulfonamide

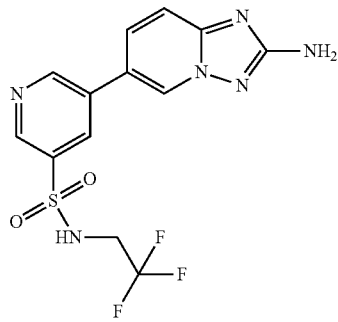 [SMILES: Nc1nc2ccc(-c3cncc(S(=O)(=O)NCC(F)(F)F)c3)cn2n1]

$^1$H NMR (d$_6$-DMSO) δ 9.24-9.23 (m, 1H), 9.19-9.18 (m, 1H), 8.96-8.95 (m, 1H), 8.91 (br s, 1H), 8.53-8.52 (m, 1H), 7.93-7.90 (m, 1H), 7.53-7.51 (m, 1H), 6.22 (s, 2H), 3.93-3.86 (m, 2H).
LCMS (method B), (M+H$^+$) 373, Rt=1.93 min.

5-(2-amino-[1,2,4]triazolo[1,5-a]pyridin-6-yl)-N-cyclohexylpyridine-3-sulfonamide

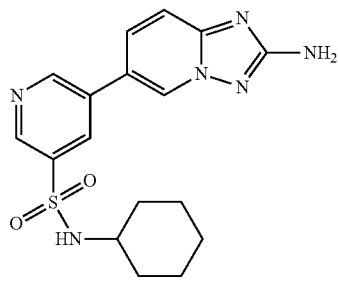 [SMILES: Nc1nc2ccc(-c3cncc(S(=O)(=O)NC4CCCCC4)c3)cn2n1]

$^1$H NMR (d$_6$-DMSO) δ 9.21-9.20 (m, 1H), 9.18-9.15 (m, 1H), 8.94-8.93 (m, 1H), 8.50-8.49 (m, 1H), 7.90 (br s, 1H), 7.88-7.85 (m, 1H), 7.53-7.51 (m, 1H), 6.21 (s, 2H), 3.11-3.10 (m, 1H), 1.60-1.57 (m, 4H), 1.46-1.43 (m, 1H), 1.22-1.10 (m, 4H), 1.09-0.99 (m, 1H).
LCMS (method B), (M+H$^+$) 373, Rt=2.20 min.

5-(2-amino-[1,2,4]triazolo[1,5-a]pyridin-6-yl)-N-(tetrahydro-2H-pyran-4-yl)pyridine-3-sulfonamide

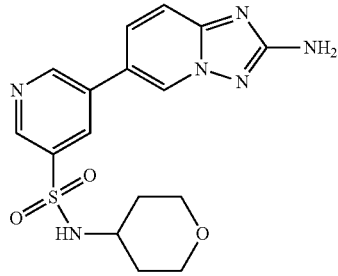 [SMILES: Nc1nc2ccc(-c3cncc(S(=O)(=O)NC4CCOCC4)c3)cn2n1]

$^1$H NMR (d$_6$-DMSO) δ 9.22-9.21 (m, 1H), 9.16-9.15 (m, 1H), 8.92-8.91 (m, 1H), 8.46-8.45 (m, 1H), 7.92 (br s, 1H), 7.89-7.86 (m, 1H), 7.53-7.50 (m, 1H), 6.21 (s, 2H), 3.82-3.79 (m, 2H), 3.25-3.18 (m, 2H), 1.57-1.53 (m, 2H), 1.18-1.04 (m, 2H), (one extra 2H not visible as under solvent peak).
LCMS (method B), (M+H$^+$) 375, Rt=1.75 min.

5-(2-amino-[1,2,4]triazolo[1,5-a]pyridin-6-yl)-N-((tetrahydro-2H-pyran-4-yl)methyl)pyridine-3-sulfonamide

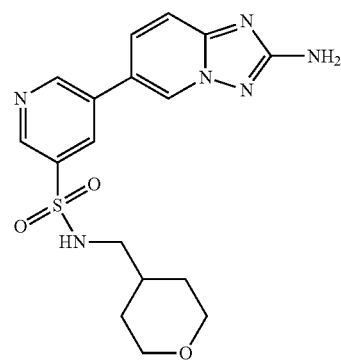 [SMILES: Nc1nc2ccc(-c3cncc(S(=O)(=O)NCC4CCOCC4)c3)cn2n1]

$^1$H NMR (d$_6$-DMSO) δ 9.22-9.21 (m, 1H), 9.16-9.15 (m, 1H), 8.92-8.91 (m, 1H), 8.46-8.45 (m, 1H), 7.92 (br s, 1H), 7.89-7.87 (m, 1H), 7.53-7.50 (m, 1H), 6.21 (s, 2H), 3.82-3.79 (m, 2H), 3.25-3.18 (m, 2H), 2.78-2.66 (m, 2H), 1.66-1.59 (m, 1H), 1.57-1.53 (m, 2H), 1.16-1.04 (m, 2H).
LCMS (method B), (M+H$^+$) 389, Rt=1.83 min.

5-(2-amino-[1,2,4]triazolo[1,5-a]pyridin-6-yl)-N-(4-hydroxycyclohexyl)pyridine-3-sulfonamide

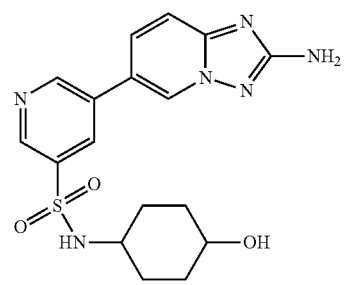 [SMILES: Nc1nc2ccc(-c3cncc(S(=O)(=O)NC4CCC(O)CC4)c3)cn2n1]

$^1$H NMR (CD$_3$OD) δ 9.12-9.11 (m, 1H), 9.02-9.01 (m, 1H), 8.94-8.93 (m, 1H), 8.54-8.53 (m, 1H), 7.93-7.90 (m, 1H), 7.55-7.53 (m, 1H), 3.51-3.45 (m, 1H), 3.20-3.14 (m, 1H), 1.89-1.79 (m, 4H), 1.37-1.22 (m, 4H).
LCMS (method B), (M+H$^+$) 389, Rt=1.66 min.

71

6-(5-(4,4-difluoropiperidin-1-ylsulfonyl)pyridin-3-yl)-[1,2,4]triazolo[1,5-a]pyridin-2-amine

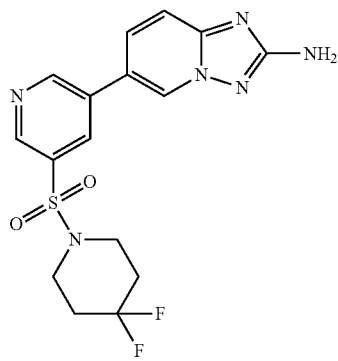 [SMILES: Nc1nc2ccc(-c3cncc(S(=O)(=O)N4CCC(F)(F)CC4)c3)cn2n1]

$^1$H NMR (d$_6$-DMSO) δ 9.30-9.29 (m, 1H), 9.22-9.21 (m, 1H), 8.94-8.93 (m, 1H), 8.46-8.45 (m, 1H), 7.96-7.93 (m, 1H), 7.51-7.49 (m, 1H), 6.21 (s, 2H), 3.25-3.22 (m, 4H), (one extra 4H not visible as under solvent peak).

LCMS (method B), (M+H$^+$) 395, Rt=2.16 min.

6-(5-(azepan-1-ylsulfonyl)pyridin-3-yl)-[1,2,4]triazolo[1,5-a]pyridin-2-amine

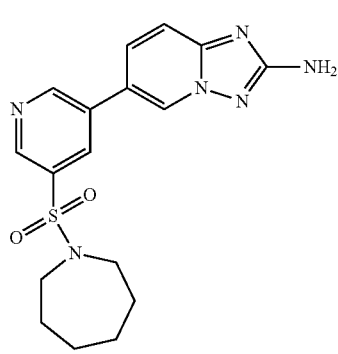 [SMILES: Nc1nc2ccc(-c3cncc(S(=O)(=O)N4CCCCCC4)c3)cn2n1]

$^1$H NMR (d$_6$-DMSO) δ 9.24-9.23 (m, 1H), 9.21-9.20 (m, 1H), 8.93-8.92 (m, 1H), 8.46-8.45 (m, 1H), 7.95-7.92 (m, 1H), 7.50-7.48 (m, 1H), 6.20 (s, 2H), 3.33-3.30 (m, 4H), 1.66-1.65 (m, 4H), 1.54-1.52 (m, 4H).

LCMS (method B), (M+H$^+$) 373, Rt=2.26 min.

72

6-(5-(azetidin-1-ylsulfonyl)pyridin-3-yl)-[1,2,4]triazolo[1,5-a]pyridin-2-amine

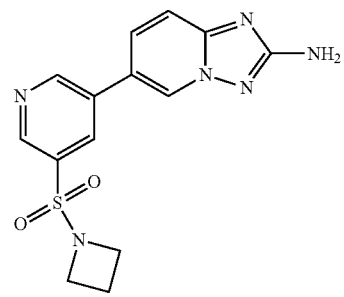 [SMILES: Nc1nc2ccc(-c3cncc(S(=O)(=O)N4CCC4)c3)cn2n1]

$^1$H NMR (d$_6$-DMSO) δ 9.33-9.32 (m, 1H), 9.25-9.24 (m, 1H), 8.95-8.94 (m, 1H), 8.47-8.46 (m, 1H), 7.98-7.95 (m, 1H), 7.51-7.49 (m, 1H), 6.21 (s, 2H), 3.83-3.79 (m, 4H), 2.09-2.01 (m, 2H).

LCMS (method B), (M+H$^+$) 331, Rt=1.82 min.

5-(2-amino-[1,2,4]triazolo[1,5-a]pyridin-6-yl)-N-(cyclobutylmethyl)pyridine-3-sulfonamide

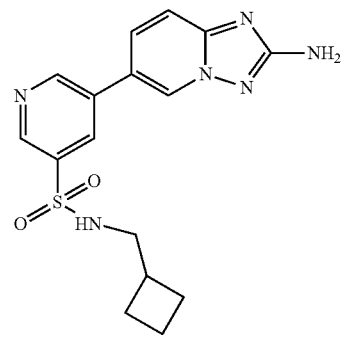 [SMILES: Nc1nc2ccc(-c3cncc(S(=O)(=O)NCC4CCC4)c3)cn2n1]

$^1$H NMR (d$_6$-DMSO) δ 9.22-9.21 (m, 1H), 9.16-9.15 (m, 1H), 8.92-8.91 (m, 1H), 8.46-8.45 (m, 1H), 7.89-7.84 (m, 2H), 7.54-7.51 (m, 1H), 6.21 (s, 2H), 2.89-2.85 (m, 2H), 2.38-2.31 (m, 1H), 1.94-1.86 (m, 2H), 1.81-1.71 (m, 2H), 1.65-1.56 (m, 2H).

LCMS (method B), (M+H$^+$) 359, Rt=2.14 min.

73

5-(2-amino-[1,2,4]triazolo[1,5-a]pyridin-6-yl)-N-ethylpyridine-3-sulfonamide

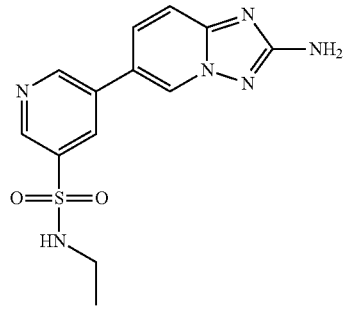 [SMILES: CCNS(=O)(=O)c1cncc(-c2ccc3nc(N)nn3c2)c1]

$^1$H NMR (d$_6$-DMSO) δ 9.21 (d, 1H), 9.16 (d, 1H), 8.92 (d, 2H), 8.44 (t, 1H), 7.89-7.82 (m, 2H), 7.51 (d, 1H), 6.20 (s, 2H), 2.89 (quin, 2H), 1.03 (t, 3H).
LCMS (method B), (M+H$^+$) 319, Rt=1.73 min.

5-(2-amino-[1,2,4]triazolo[1,5-a]pyridin-6-yl)-N-methylpyridine-3-sulfonamide

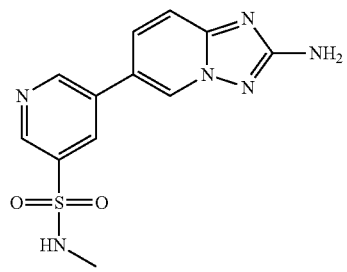 [SMILES: CNS(=O)(=O)c1cncc(-c2ccc3nc(N)nn3c2)c1]

$^1$H NMR (d$_6$-DMSO) δ 9.23 (d, 1H), 9.17 (d, 1H), 8.91 (d, 1H), 8.43 (t, 1H), 7.88 (dd, 1H), 7.70 (br s, 1H), 7.50 (d, 1H), 6.21 (s, 2H), 3.35 (s, 3H).
LCMS (method B), (M+H$^+$) 305, Rt=1.62 min.

6-(3,4-dimethoxyphenyl)-8-fluoro-[1,2,4]triazolo[1,5-a]pyridin-2-amine

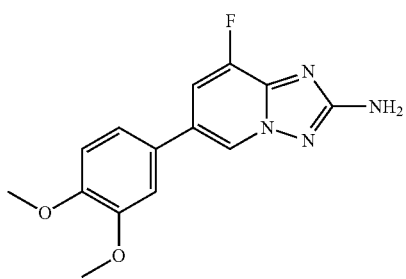 [SMILES: COc1ccc(-c2cc(F)c3nc(N)nn3c2)cc1OC]

$^1$H NMR (d$_6$-DMSO) δ 8.85 (d, 1H), 7.83 (dd, 1H), 7.33 (d, 1H), 7.29 (dd, 1H), 7.03 (d, 1H), 6.26 (s, 2H), 3.87 (s, 3H), 3.80 (s, 3H).
LCMS (method C), (M+H$^+$) 289, Rt=2.13 min.

74

6-(3,4-dimethoxyphenyl)-8-methyl-[1,2,4]triazolo[1,5-a]pyridin-2-amine

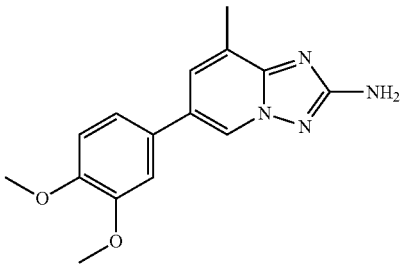 [SMILES: COc1ccc(-c2cc(C)c3nc(N)nn3c2)cc1OC]

$^1$H NMR (d$_6$-DMSO) δ 8.99 (s, 1H), 7.99 (s, 1H), 7.31-7.35 (m, 2H), 7.07 (d, 1H), 3.88 (s, 3H), 3.81 (s, 3H), 1.24 (s, 3H).
LCMS (method C), (M+H$^+$) 285, Rt=1.99 min.

6-(5-(benzylsulfonyl)pyridin-3-yl)-[1,2,4]triazolo[1,5-a]pyridin-2-amine

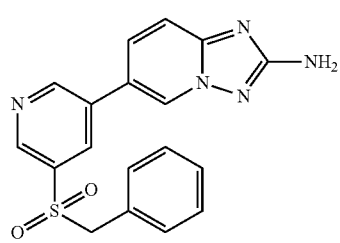 [SMILES: Nc1nc2ccc(-c3cncc(S(=O)(=O)Cc4ccccc4)c3)cn2n1]

$^1$H NMR (d$_6$-DMSO) δ 9.05 (d, 1H), 8.75 (d, 1H), 8.46 (d, 1H), 8.12 (t, 1H), 7.82 (dd, 1H), 7.39-7.47 (m, 3H), 7.23-7.34 (m, 3H), 6.16 (brs, 2H), 4.42 (s, 2H).
LCMS (method C), (M+H$^+$) 334, Rt=2.34 min.

6-(5-(tert-Butylsulfonyl)pyridin-3-yl)-[1,2,4]triazolo[1,5-a]pyridin-2-amine

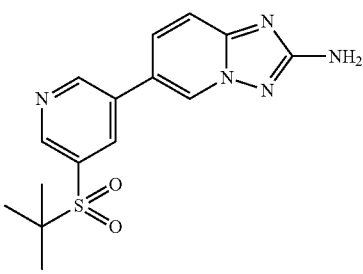 [SMILES: CC(C)(C)S(=O)(=O)c1cncc(-c2ccc3nc(N)nn3c2)c1]

$^1$H NMR (d$_6$-DMSO) δ 9.42 (s, 1H), 9.36 (s, 1H), 8.99 (s, 1H), 8.53 (s, 1H), 8.22 (d, 1H), 7.71 (d, 1H), 1.32 (s, 9H);
LCMS (method C), (M+H$^+$) 332, Rt=1.88 min.

5-(2-amino-[1,2,4]triazolo[1,5-a]pyridin-6-yl)-N-ethyl-N-methylpyridine-3-sulfonamide

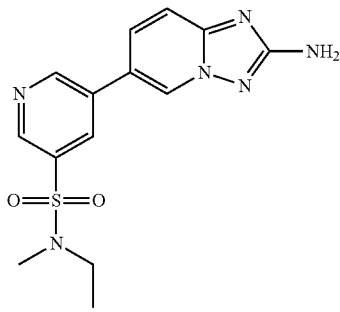 [SMILES: CCN(C)S(=O)(=O)c1cncc(-c2ccc3nc(N)nn3c2)c1]

$^1$H NMR (d$_6$-DMSO) δ 9.26 (d, 1H), 9.21 (d, 1H), 8.92 (d, 1H), 8.44 (t, 1H), 7.93 (dd, 1H), 7.49 (dd, 1H), 7.19 (s, 2H), 3.16 (q, 2H), 2.78 (s, 3H), 1.03 (t, 3H).

LCMS (method B), (M+H$^+$) 333, Rt=1.93 min.

5-(2-amino-8-fluoro-[1,2,4]triazolo[1,5-a]pyridin-6-yl)-N-tert-butylpyridine-3-sulfonamide

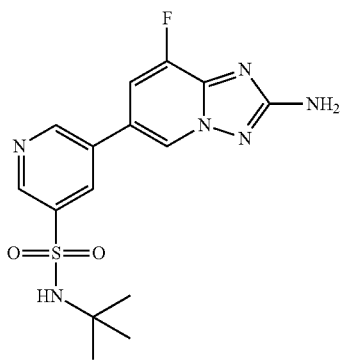 [SMILES: CC(C)(C)NS(=O)(=O)c1cncc(-c2cc(F)c3nc(N)nn3c2)c1]

$^1$H NMR (d$_6$-DMSO) δ 9.19 (d, 1H), 9.08 (d, 1H, 8.97 (d, 1H), 8.54 (t, 1H), 7.95 (dd, 1H), 7.76 (s, 1H), 6.41 (s, 2H), 1.15 (s, 9H).

LCMS (method B), (M+H$^+$) 365, Rt=2.10 min.

6-(5-isobutoxypyridin-3-yl)-[1,2,4]triazolo[1,5-a]pyridin-2-amine

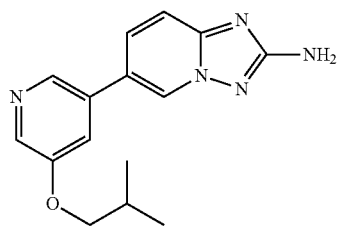 [SMILES: CC(C)COc1cncc(-c2ccc3nc(N)nn3c2)c1]

$^1$H NMR (d$_6$-DMSO) δ 9.07 (s, 1H), 8.54 (s, 1H), 8.28-8.27 (m, 1H), 7.88-7.86 (m, 1H), 7.73 (s, 1H), 7.46-7.44 (m, 1H), 6.12 (br s, 2H), 3.95-3.93 (m, 2H), 2.10-2.04 (m, 1H), 1.03-1.01 (d, 6H).

LCMS (method B), (M+H$^+$) 284, Rt=2.04 min.

6-(5-(benzyloxy)pyridin-3-yl)-[1,2,4]triazolo[1,5-a]pyridin-2-amine

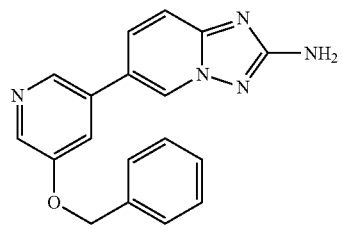 [SMILES: Nc1nc2ccc(-c3cncc(OCc4ccccc4)c3)cn2n1]

$^1$H NMR (d$_6$-DMSO) δ 9.07-9.06 (m, 1H), 8.58-8.57 (m, 1H), 8.36-8.35 (m, 1H), 7.88-7.87 (m, 1H), 7.86-7.85 (m, 1H), 7.52-7.48 (m, 2H), 7.45-7.41 (m, 2H), 7.38-7.35 (m, 2H), 6.13 (br s, 2H), 5.30 (s, 2H).

LCMS (method B), (M+H$^+$) 318, Rt=2.22 min.

6-(5-phenoxypyridin-3-yl)-[1,2,4]triazolo[1,5-a]pyridin-2-amine

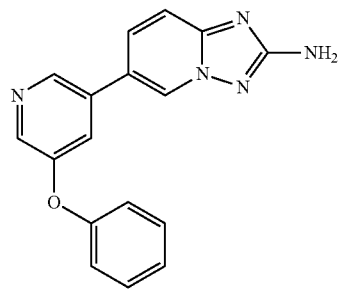 [SMILES: Nc1nc2ccc(-c3cncc(Oc4ccccc4)c3)cn2n1]

$^1$H NMR (d$_6$-DMSO) δ 9.09 (s, 1H), 8.82-8.76 (m, 1H), 8.33-8.31 (m, 1H), 7.92-7.86 (m, 1H), 7.84-7.80 (m, 1H), 7.49-7.40 (m, 3H), 7.22-7.19 (m, 1H), 7.15-7.13 (m, 2H), 6.12 (br s, 2H).

LCMS (method B), (M+H$^+$) 304, Rt=2.20 min.

6-(5-(neopentyloxy)pyridin-3-yl)-[1,2,4]triazolo[1,5-a]pyridin-2-amine

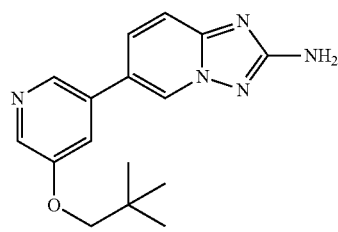 [SMILES: CC(C)(C)COc1cncc(-c2ccc3nc(N)nn3c2)c1]

$^1$H NMR (d$_6$-DMSO) δ 9.08 (s, 1H), 8.55 (s, 1H), 8.30-8.29 (m, 1H), 7.89-7.86 (m, 1H), 7.74-7.73 (m, 1H), 7.46-7.44 (m, 1H), 6.12 (br s, 2H), 3.83 (s, 2H), 2.51 (s, 9H).

LCMS (method B), (M+H$^+$) 298, Rt=2.23 min.

77

6-(5-(neopentylsulfonyl)pyridin-3-yl)-[1,2,4]triazolo[1,5-a]pyridin-2-amine

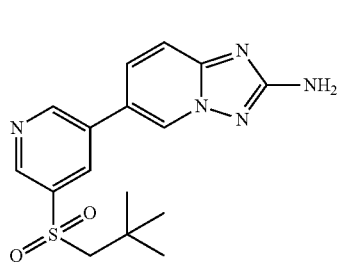 [SMILES: CC(C)(C)CS(=O)(=O)c1cncc(-c2ccc3nc(N)nn3c2)c1]

¹H NMR (d₆-DMSO) δ 9.30-9.29 (m, 1H), 9.24-9.23 (m, 1H), 9.01-9.00 (m, 1H), 8.60-8.59 (m, 1H), 7.98-7.95 (m, 1H), 7.52-7.50 (m, 1H), 6.20 (br s, 2H), 3.51 (s, 2H), 1.14 (s, 9H).

LCMS (method B), (M+H⁺) 346, Rt=2.18 min.

5-(2-amino-[1,2,4]triazolo[1,5-a]pyridin-6-yl)-N-(cyclopentylmethyl)pyridine-3-sulfonamide

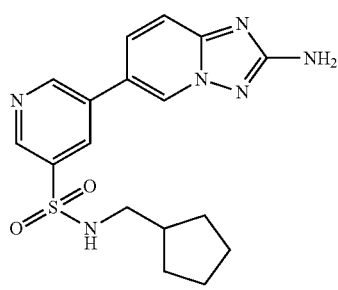 [SMILES: Nc1nc2ccc(-c3cncc(S(=O)(=O)NCC4CCCC4)c3)cn2n1]

¹H NMR (d₆-DMSO) δ 9.21 (d, 1H), 9.15 (s, 1H), 8.91 (d, 1H), 8.46-8.45 (m, 1H), 7.92-7.83 (m, 2H), 7.55-7.47 (m, 1H), 6.21 (br s, 2H), 2.76 (t, 2H), 1.99-1.90 (m, 1H), 1.66-1.57 (m, 2H), 1.55-1.38 (m, 2H), 1.20-1.10 (m, 2H).

LCMS (method C), (M+H⁺) 373, RT=2.28 min.

5-(2-amino-[1,2,4]triazolo[1,5-a]pyridin-6-yl)-N-(cycloheptylmethyl)pyridine-3-sulfonamide

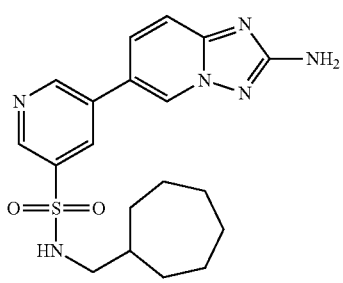 [SMILES: Nc1nc2ccc(-c3cncc(S(=O)(=O)NCC4CCCCCC4)c3)cn2n1]

¹H NMR (CD₃OD) δ 9.10 (d, 1H), 8.98 (d, 1H), 8.90-8.92 (m, 1H), 8.48 (t, 1H), 7.89 (dd, 1H), 7.52 (d, 1H), 2.77 (d, 2H), 1.49-1.77 (m, 9H), 1.32-1.49 (m, 2H), 1.08-1.22 (m, 2H).

LCMS (method C), (M+H⁺) 401, RT=2.52 min.

78

5-(2-amino-[1,2,4]triazolo[1,5-a]pyridin-6-yl)-N-(3-isopropylphenyl)pyridine-3-sulfonamide

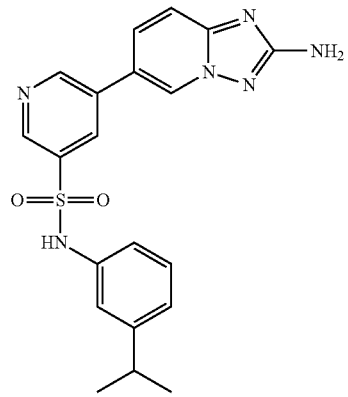 [SMILES: CC(C)c1cccc(NS(=O)(=O)c2cncc(-c3ccc4nc(N)nn4c3)c2)c1]

¹H NMR (CD₃OD) δ 9.02 (d, 1H), 8.82 (d, 1H), 8.73-8.75 (m, 1H), 8.23 (t, 1H), 7.70 (dd, 1H), 7.48 (dm, 1H), 7.17-7.22 (m, 1H), 7.02 (dm, 1H), 6.95-6.99 (m, 2H), 2.80 (quintet, 1H), 1.14 (d, 6H).

LCMS (method A), (M+H⁺) 409, RT=8.85 min.

5-(2-amino-[1,2,4]triazolo[1,5-a]pyridin-6-yl)-N-(2-fluorophenyl)pyridine-3-sulfonamide

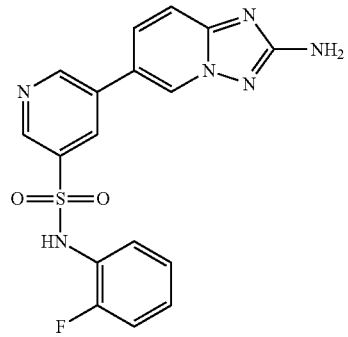 [SMILES: Nc1nc2ccc(-c3cncc(S(=O)(=O)Nc4ccccc4F)c3)cn2n1]

¹H NMR (CD₃OD) δ 9.04 (d, 1H), 8.82 (d, 1H), 8.78-8.80 (m, 1H), 8.54 (s, 0.5H), 8.36 (t, 1H), 7.76 (dd, 1H), 7.51-7.55 (m, 1H), 7.50 (dm, 1H), 7.13-7.20 (m, 2H), 6.99-7.06 (m, 2H).

LCMS (method A), (M+H⁺) 385, RT=7.40 min.

5-(2-amino-[1,2,4]triazolo[1,5-a]pyridin-6-yl)-N-(4-isopropylphenyl)pyridine-3-sulfonamide

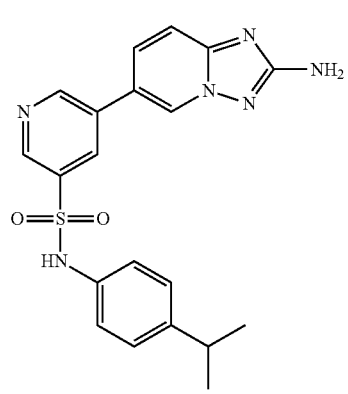 [SMILES: CC(C)c1ccc(NS(=O)(=O)c2cncc(-c3ccc4nc(N)nn4c3)c2)cc1]

¹H NMR (CD₃OD) δ 9.02 (d, 1H), 8.81 (d, 1H), 8.76-8.78 (m, 1H), 8.22 (t, 1H), 7.69 (dd, 1H), 7.47 (d, 1H), 7.14 (d, 2H), 7.04 (d, 2H), 2.84 (quintet, 1H), 1.18 (d, 6H).
LCMS (method A), (M+H⁺) 409, RT=8.98 min.

5-(2-amino-[1,2,4]triazolo[1,5-a]pyridin-6-yl)-N-(2-methoxyphenyl)pyridine-3-sulfonamide

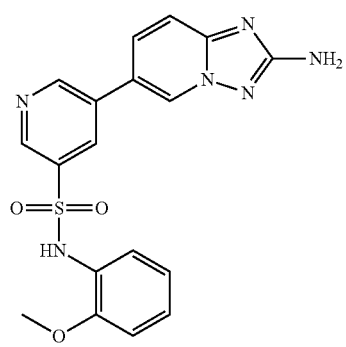 [SMILES: COc1ccccc1NS(=O)(=O)c1cncc(-c2ccc3nc(N)nn3c2)c1]

¹H NMR (CD₃OD) δ 9.02 (d, 1H), 8.77 (d, 1H), 8.75 (s, 1H), 8.25 (t, 1H), 8.12 (s, 1H), 7.74 (dd, 1H), 7.45-7.51 (m, 2H), 7.17-7.23 (tm, 1H), 6.94-7.01 (tm, 1H), 6.84 (d, 1H), 3.45 (s, 3H).
LCMS (method A), (M+H⁺) 397, RT=7.51 min.

5-(2-amino-[1,2,4]triazolo[1,5-a]pyridin-6-yl)-N-(2,4-difluorophenyl)pyridine-3-sulfonamide

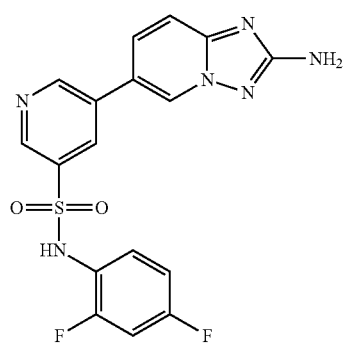 [SMILES: Nc1nc2ccc(-c3cncc(S(=O)(=O)Nc4ccc(F)cc4F)c3)cn2n1]

¹H NMR (CD₃OD) δ 9.07 (d, 1H), 8.82-8.83 (m, 1H), 8.80 (d, 1H), 8.50 (s, 0.5H), 8.39 (t, 1H), 7.79 (dd, 1H), 7.48-7.56 (m, 2H), 6.90-7.02 (m, 2H).
LCMS (method A), (M+H⁺) 403, RT=7.55 min.

5-(2-amino-[1,2,4]triazolo[1,5-a]pyridin-6-yl)-N-tert-butylnicotinamide

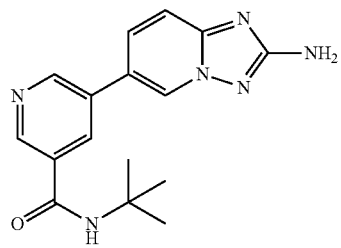 [SMILES: CC(C)(C)NC(=O)c1cncc(-c2ccc3nc(N)nn3c2)c1]

¹H NMR (d₆-CD₃OD) δ 8.98 (d, 1H), 8.91 (dd, 2H), 8.54 (t, 1H), 7.92 (dd, 1H), 7.51 (d, 1H), 1.51 (s, 9H).
LCMS (method C), (M+H⁺) 346, RT=2.18 min.

5-(2-amino-[1,2,4]triazolo[1,5-a]pyridin-6-yl)-N-(4-methoxyphenyl)pyridine-3-sulfonamide

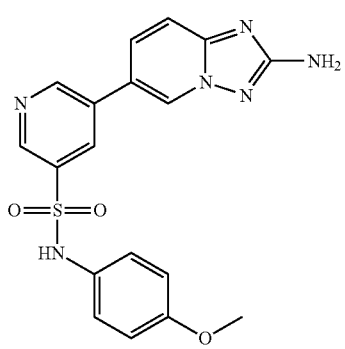 [SMILES: COc1ccc(NS(=O)(=O)c2cncc(-c3ccc4nc(N)nn4c3)c2)cc1]

¹H NMR (CD₃OD/CDCl₃) δ 9.02 (d, 1H), 8.75 (d, 1H), 8.73-8.74 (m, 1H), 8.20 (t, 1H), 7.71 (dd, 1H), 7.40 (dd, 1H), 7.00-7.05 (m, 2H), 6.80-6.85 (m, 2H), 3.74 (s, 3H).
LCMS (method A), (M+H⁺) 397, RT=7.39 min.

5-(2-amino-[1,2,4]triazolo[1,5-a]pyridin-6-yl)-N-(3-fluorophenyl)pyridine-3-sulfonamide

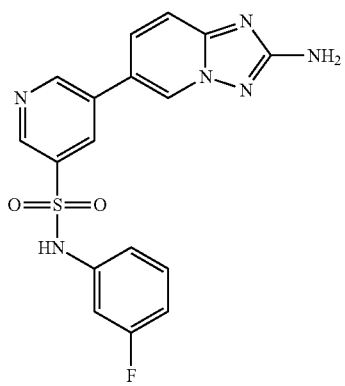 [SMILES: Nc1nc2ccc(-c3cncc(S(=O)(=O)Nc4cccc(F)c4)c3)cn2n1]

¹H NMR (CD₃OD/CDCl₃) δ 9.01 (d, 1H), 8.89 (d, 1H), 8.73-8.74 (m, 1H), 8.34 (t, 1H), 7.72 (dd, 1H), 7.49 (dd, 1H), 7.20-7.30 (m, 1H), 6.90-7.00 (m, 2H), 6.78-6.86 (m, 1H).
LCMS (method A), (M+H⁺) 385, RT=7.69 min.

81

5-(2-amino-[1,2,4]triazolo[1,5-a]pyridin-6-yl)-N-(3,4-difluorophenyl)pyridine-3-sulfonamide

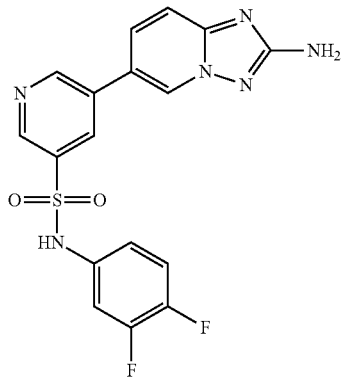 [SMILES: Nc1nc2ccc(-c3cncc(S(=O)(=O)Nc4ccc(F)c(F)c4)c3)cn2n1]

¹H NMR (CD₃OD/CDCl₃) δ 9.01-9.02 (m, 1H), 8.86 (d, 1H), 8.78-8.80 (m, 1H), 8.55 (s, 0.5H), 8.37 (t, 1H), 7.77 (dd, 1H), 7.50 (d, 1H), 7.02-7.14 (m, 2H), 6.82-6.90 (m, 1H).
LCMS (method A), (M+H⁺) 403, RT=7.94 min.

5-(2-amino-[1,2,4]triazolo[1,5-a]pyridin-6-yl)-N-(2-isopropylphenyl)pyridine-3-sulfonamide

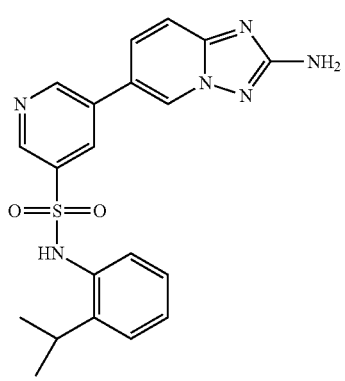 [SMILES: CC(C)c1ccccc1NS(=O)(=O)c1cncc(-c2ccc3nc(N)nn3c2)c1]

¹H NMR (CD₃OD/CDCl₃) δ 9.04 (d, 1H), 8.78 (d, 1H), 8.71 (dd, 1H), 8.20 (t, 1H), 7.70 (dd, 1H), 7.48 (dd, 1H), 7.25-7.30 (m, 2H), 7.08-7.14 (m, 1H), 7.02 (dd, 1H), 3.31 (m, 1H under methanol peak) 0.98 (d, 6H).
LCMS (method A), (M+H⁺) 409, RT=8.46 min.

5-(2-amino-[1,2,4]triazolo[1,5-a]pyridin-6-yl)-N-(3,5-difluorophenyl)pyridine-3-sulfonamide

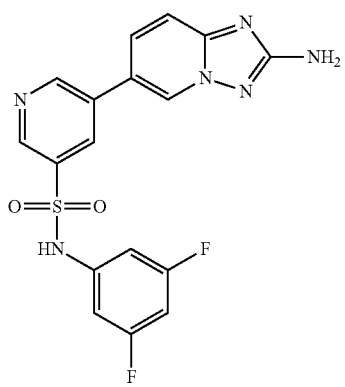 [SMILES: Nc1nc2ccc(-c3cncc(S(=O)(=O)Nc4cc(F)cc(F)c4)c3)cn2n1]

82

¹H NMR (CD₃OD/CDCl₃) δ 9.05 (d, 1H), 8.94 (d, 1H), 8.78-8.79 (m, 1H), 8.42 (t, 1H), 7.76-7.79 (dd, 1H under CHCl3 peak), 7.50 (dd, 1H), 6.74-6.81 (m, 2H), 6.58-6.65 (m, 1H).
LCMS (method A), (M+H⁺) 403, RT=8.08 min.

5-(2-amino-[1,2,4]triazolo[1,5-a]pyridin-6-yl)-N-(3-methoxyphenyl)pyridine-3-sulfonamide

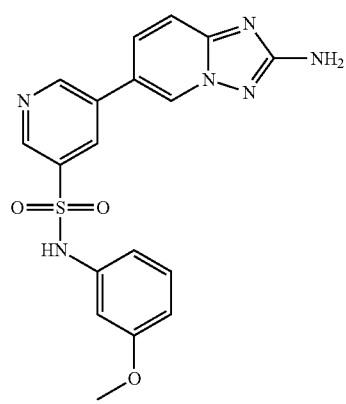 [SMILES: COc1cccc(NS(=O)(=O)c2cncc(-c3ccc4nc(N)nn4c3)c2)c1]

¹H NMR (CD₃OD/CDCl₃) δ 8.95 (d, 1H), 8.88 (d, 1H), 8.62-8.63 (m, 1H), 8.24 (t, 1H), 7.66 (dd, 1H), 7.47 (dd, 1H), 7.15 (t, 1H), 6.73 (t, 1H), 6.65-6.71 (m, 2H), 3.73 (s, 3H).
LCMS (method A), (M+H⁺) 397, RT=7.53 min.

5-(2-amino-[1,2,4]triazolo[1,5-a]pyridin-6-yl)-N-(2,3-difluorophenyl)pyridine-3-sulfonamide

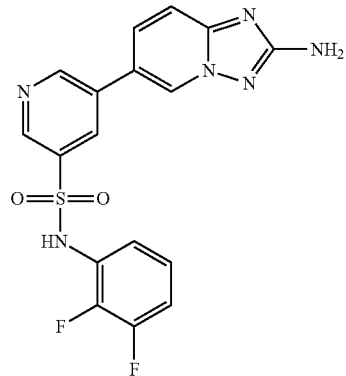 [SMILES: Nc1nc2ccc(-c3cncc(S(=O)(=O)Nc4cccc(F)c4F)c3)cn2n1]

¹H NMR (CD₃OD/CDCl₃) δ 9.06 (d, 1H), 8.88 (d, 1H), 8.83 (br s, 1H), 8.43 (t, 1H), 7.80 (dd, 1H), 7.50 (d, 1H), 7.26-7.36 (m, 1H), 6.98-7.11 (m, 2H).
LCMS (method A), (M+H⁺) 403, RT=7.61 min.

83

5-(2-amino-[1,2,4]triazolo[1,5-a]pyridin-6-yl)-N-(1-methylcyclobutyl)pyridine-3-sulfonamide

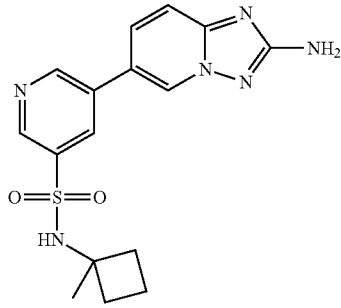 [SMILES: CC1(NS(=O)(=O)c2cncc(-c3ccc4nc(N)nn4c3)c2)CCC1]

¹H NMR (CD₃OD/CDCl₃) δ 9.39 (br s, 1H), 9.10 (s, 1H), 8.50 (s, 1H), 8.24 (s, 1H), 7.88 (s, 1H), 7.54-7.57 (m, 1H under CHCl3 peak), 2.14-2.29 (m, 2H), 1.84-1.89 (m, 2H), 1.66-1.72 (m, 2H), 1.36 (s, 3H).
LCMS (method A), (M+H⁺) 359, RT=7.26 min.

5-(2-amino-[1,2,4]triazolo[1,5-a]pyridin-6-yl)-N-(2-aminoethyl)pyridine-3-sulfonamide

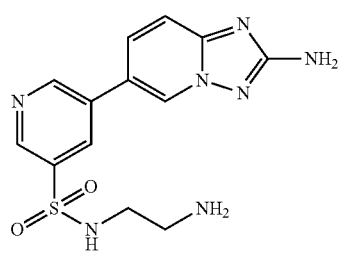 [SMILES: NCCNS(=O)(=O)c1cncc(-c2ccc3nc(N)nn3c2)c1]

¹H NMR (d₆-DMSO) δ 9.22 (d, 1H), 9.15 (s, 1H), 8.93 (d, 1H), 8.46 (t, 1H), 7.89-7.86 (dd, 1H), 7.51 (d, 1H), 6.20 (br s, 2H), 2.84 (t, 2H), 2.55 (t, 2H), one extra 2H not visible under water peak.
LCMS (method E), (M+H⁺) 334, RT=1.52 min.

5-(2-amino-8-fluoro-[1,2,4]triazolo[1,5-a]pyridin-6-yl)-N-methylpyridine-3-sulfonamide

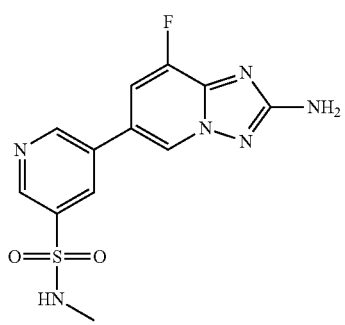 [SMILES: CNS(=O)(=O)c1cncc(-c2cc(F)c3nc(N)nn3c2)c1]

¹H NMR (d₆-DMSO) δ 9.24 (d, 1H), 9.11 (d, 1H), 8.91 (d, 1H), 8.46 (t, 1H), 7.99 (dd, 1H), 7.72 (q, 1H), 6.42 (s, 2H), (one extra 3H not visible as under solvent peak).
LCMS (method A), (M+H⁺) 323, RT=6.09 min.

84

5-(2-amino-8-fluoro-[1,2,4]triazolo[1,5-a]pyridin-6-yl)-N-isopropylpyridine-3-sulfonamide

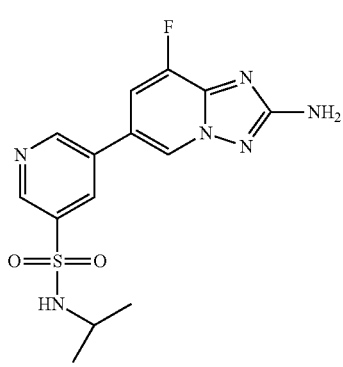 [SMILES: CC(C)NS(=O)(=O)c1cncc(-c2cc(F)c3nc(N)nn3c2)c1]

¹H NMR (d₆-DMSO) δ 9.21 (d, 1H), 9.10 (d, 1H), 8.94 (d, 1H), 8.50 (t, 1H), 7.98 (dd, 1H), 7.83 (d, 1H), 6.42 (s, 2H), 3.45-3.37 (m, 1H), 0.98 (d, 6H).
LCMS (method A), (M+H⁺) 351, RT=7.09 min.

5-(2-amino-8-fluoro-[1,2,4]triazolo[1,5-a]pyridin-6-yl)-N-propylpyridine-3-sulfonamide

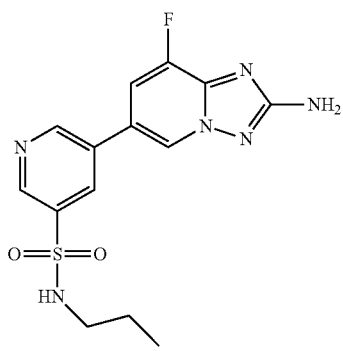 [SMILES: CCCNS(=O)(=O)c1cncc(-c2cc(F)c3nc(N)nn3c2)c1]

¹H NMR (d₆-DMSO) δ 9.22 (d, 1H), 9.10 (d, 1H), 8.92 (d, 1H), 8.47 (t, 1H), 7.98 (dd, 1H), 7.83 (br s, 1H), 6.42 (s, 2H), 2.80 (br s, 1H), 1.45-1.36 (m, 2H), 0.81 (t, 3H).
LCMS (method A), (M+H⁺) 351, RT=7.27 min.

6-(5-(azetidin-1-ylsulfonyl)pyridin-3-yl)-8-fluoro-[1,2,4]triazolo[1,5-a]pyridin-2-amine

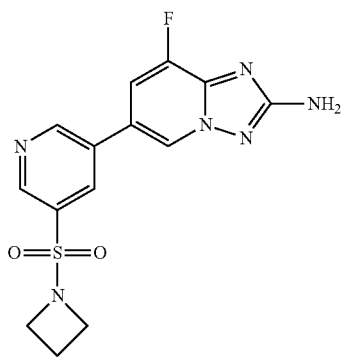 [SMILES: Nc1nc2c(F)cc(-c3cncc(S(=O)(=O)N4CCC4)c3)cn2n1]

¹H NMR (d₆-DMSO) δ 9.34 (d, 1H), 9.21 (d, 1H), 8.95 (d, 1H), 8.51 (t, 1H), 8.10 (dd, 1H), 6.42 (s, 2H), 6.42 (s, 2H), 3.81 (t, 4H), 2.04 (q, 2H).
LCMS (method A), (M+H⁺) 349, RT=6.90 min.

5-(2-amino-8-fluoro-[1,2,4]triazolo[1,5-a]pyridin-6-yl)-N-(2,2,2-trifluoroethyl)pyridine-3-sulfonamide 8-fluoro-6-(3-(methylsulfonyl)phenyl)-[1,2,4]triazolo[1,5-a]pyridin-2-amine

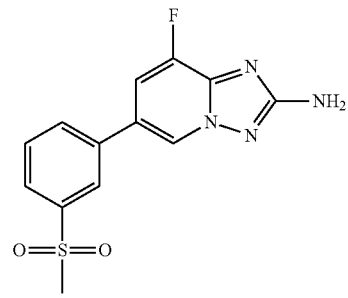

LCMS (method C), (M+H⁺) 307, RT=1.88 min.

6-(6-amino-5-(trifluoromethyl)pyridin-3-yl)-[1,2,4]triazolo[1,5-a]pyridin-2-amine

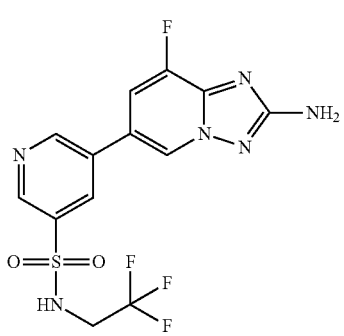 [SMILES: Nc1nc2c(F)cc(-c3cncc(S(=O)(=O)NCC(F)(F)F)c3)cn2n1]

¹H NMR (d₆-DMSO) δ 9.25 (d, 1H), 9.15 (d, 1H), 8.96 (d, 1H), 8.90 (t, 1H), 8.55 (t, 1H), 8.03 (dd, 1H), 6.43 (s, 2H) 3.94-3.85 (m, 2H).
LCMS (method A), (M+H⁺) 391, RT=7.44 min.

5-(2-amino-8-fluoro-[1,2,4]triazolo[1,5-a]pyridin-6-yl)-N-ethyl-N-methylpyridine-3-sulfonamide

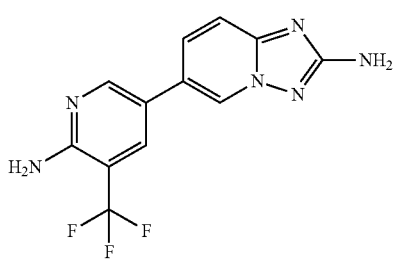

¹H NMR (d₆-DMSO+D₂O) δ 9.07 (d, 1H), 8.58 (d, 1H), 8.14 (d, 1H), 8.00 (dd, 1H), 7.57 (d, 1H).
LCMS (method C), (M+H 295, RT=1.78 min.

5-(3-(2-amino-[1,2,4]triazolo[1,5-a]pyridin-6-yl)phenylsulfonamido)pentanoic acid

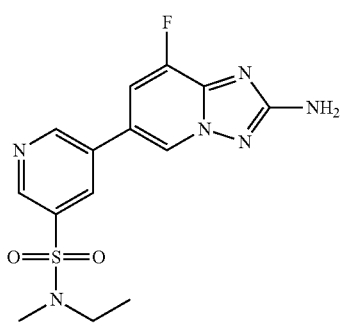 [SMILES: CCN(C)S(=O)(=O)c1cncc(-c2cc(F)c3nc(N)nn3c2)c1]

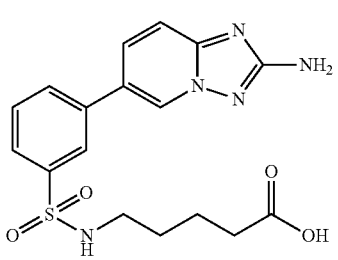 [SMILES: Nc1nc2ccc(-c3cccc(S(=O)(=O)NCCCCC(=O)O)c3)cn2n1]

¹H NMR (d₆-DMSO) δ 9.28 (d, 1H), 9.18 (d, 1H), 8.93 (d, 1H), 8.49 (t, 1H), 8.08 (dd, 1H), 6.97 (s, 0.4H), 3.15 (q, 2H), 2.78 (s, 3H), 1.08 (t, 3H).
LCMS (method A), (M+H⁺) 351, RT=7.45 min.

LCMS (method A), (M+H⁺) 390, RT=1.89 min.

4-(3-(2-amino-[1,2,4]triazolo[1,5-a]pyridin-6-yl)phenylsulfonamido)butanoic acid

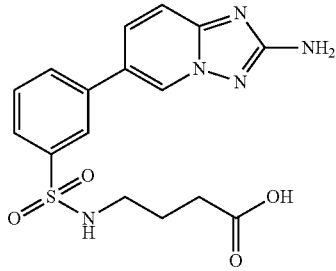 [SMILES: Nc1nc2ccc(-c3cccc(S(=O)(=O)NCCCC(=O)O)c3)cn2n1]

LCMS (method A), (M+H⁺) 376, RT=1.80 min.

6-(5-(benzylthio)pyridin-3-yl)-[1,2,4]triazolo[1,5-a]pyridin-2-amine

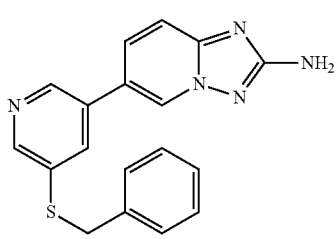 [SMILES: Nc1nc2ccc(-c3cncc(SCc4ccccc4)c3)cn2n1]

¹H NMR (d₆-DMSO) δ 9.05 (d, 1H), 8.75 (d, 1H), 8.46 (d, 1H), 8.12 (t, 1H), 7.82 (dd, 1H), 7.39-7.47 (m, 3H), 7.23-7.34 (m, 3H), 6.16 (brs, 2H), 4.42 (s, 2H).
LCMS (method C), (M+H⁺) 334, Rt=2.34 min.

8-fluoro-6-(5-(trifluoromethyl)pyridin-3-yl)-[1,2,4]triazolo[1,5-a]pyridin-2-amine

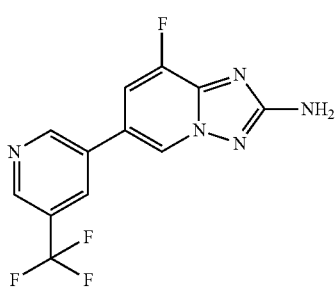 [SMILES: Nc1nc2c(F)cc(-c3cncc(C(F)(F)F)c3)cn2n1]

¹H NMR (d₆-DMSO) δ 9.31 (d, 1H), 9.18 (d, 1H), 8.98 (d, 1H), 8.63 (s, 1H), 8.08 (dd, 1H), 6.42 (s, 2H).
LCMS (05), (M+H⁺) 298, Rt=7.87 min.

6-(4-fluorophenyl)-[1,2,4]triazolo[1,5-a]pyridin-2-amine hydrochloride

¹H NMR (d₆-DMSO) δ 9.17 (s, 1H), 8.13 (d, 1H), 7.86 (d, 1H), 7.84 (d, 1H), 7.69 (d, 1H), 7.37 (dd, 2H).
LCMS (method C), (M+H⁺) 229, RT=7.40 min.

6-(3-methoxyphenyl)-[1,2,4]triazolo[1,5-a]pyridin-2-amine hydrochloride

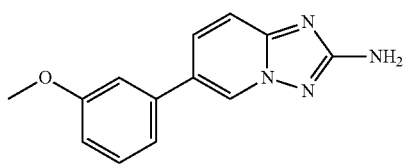 [SMILES: COc1cccc(-c2ccc3nc(N)nn3c2)c1]

¹H NMR (d₆-DMSO) δ 9.19 (s, 1H), 8.15 (d, 1H), 7.69 (d, 1H), 7.43 (dd, 1H), 7.36 (d, 1H), 7.34 (s, 1H), 7.02 (d, 1H), 3.85 (s, 3H).
LCMS (method C), (M+H⁺) 241, RT=7.34 min.

6-(3,4,5-trimethoxyphenyl)-[1,2,4]triazolo[1,5-a]pyridin-2-amine hydrochloride

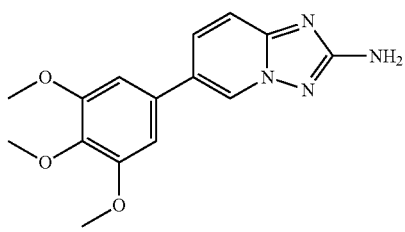 [SMILES: COc1cc(-c2ccc3nc(N)nn3c2)cc(OC)c1OC]

¹H NMR (d₆-DMSO) δ 9.13 (s, 1H), 8.10 (d, 1H), 7.57 (d, 1H), 6.93 (s, 2H), 3.75 (s, 6H), 3.56 (s, 3H).
LCMS (method C), (M+H⁺) 301, RT=6.88 min.

6-m-tolyl-[1,2,4]triazolo[1,5-a]pyridin-2-amine

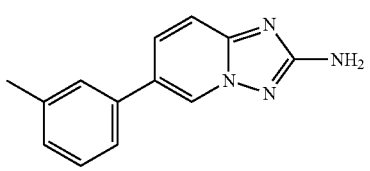 [SMILES: Cc1cccc(-c2ccc3nc(N)nn3c2)c1]

¹H NMR (d₆-DMSO) δ 8.96 (s, 1H), 7.76 (d, 1H), 7.56 (d, 1H), 7.51 (d, 1H), 7.42 (d, 1H), 7.36 (dd, 1H), 7.19 (d, 1H), 6.08 (s, 2H), 2.38 (s, 3H).
LCMS (method A), (M+H 225, RT=7.94 min.

3-(2-amino-[1,2,4]triazolo[1,5-a]pyridin-6-yl)benzonitrile

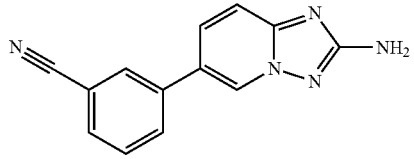 [SMILES: N#Cc1cccc(-c2ccc3nc(N)nn3c2)c1]

¹H NMR (d₆-DMSO) δ 9.06 (s, 1H), 8.28 (s, 1H), 8.10 (d, 1H), 7.87 (d, 1H), 7.83 (d, 1H), 7.68 (dd, 1H), 7.45 (d, 1H), 6.16 (s, 2H).
LCMS (method A), (M+H⁺) 236, RT=7.02 min.

6-(3-chlorophenyl)-[1,2,4]triazolo[1,5-a]pyridin-2-amine

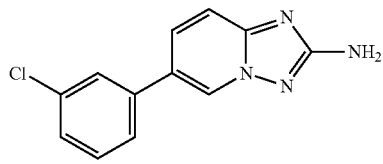 [SMILES: Nc1nc2ccc(-c3cccc(Cl)c3)cn2n1]

¹H NMR (d₆-DMSO) δ 8.99 (s, 1H), 7.84 (s, 1H), 7.80 (d, 1H), 7.72 (d, 1H), 7.50 (dd, 1H), 7.43 (d, 2H), 6.13 (s, 2H).
LCMS (method A), (M+H 245, RT=8.22 min.

6-phenyl-[1,2,4]triazolo[1,5-a]pyridin-2-amine

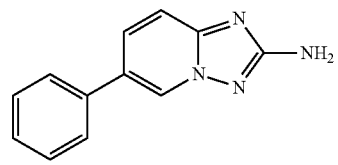 [SMILES: Nc1nc2ccc(-c3ccccc3)cn2n1]

¹H NMR (d₆-DMSO) δ 8.90 (s, 1H), 7.77 (d, 1H), 7.73 (d, 2H), 7.48 (dd, 2H), 7.43 (d, 1H), 7.38 (dd, 1H).
LCMS (method A), (M+H⁺) 211, RT=7.14 min.

6-(2-methoxyphenyl)-[1,2,4]triazolo[1,5-a]pyridin-2-amine

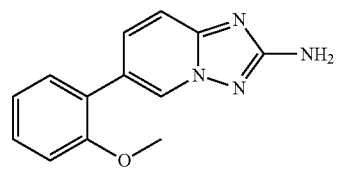 [SMILES: COc1ccccc1-c1ccc2nc(N)nn2c1]

¹H NMR (d₆-DMSO) δ 8.62 (s, 1H), 7.56 (dd, 1H), 7.42-7.36 (m, 3H), 7.14 (d, 1H), 7.05 (dd, 1H), 6.04 (s, 2H), 3.81 (s, 3H);
LCMS (method A), (M+H⁺) 241, RT=7.20 min.

6-(3-(ethylamino)phenyl)-[1,2,4]triazolo[1,5-a]pyridin-2-amine

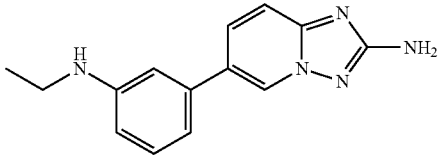 [SMILES: CCNc1cccc(-c2ccc3nc(N)nn3c2)c1]

¹H NMR (d₆-DMSO) δ 8.75 (s, 1H), 7.68 (dd, 1H), 7.40 (d, 1H), 7.16 (dd, 1H), 6.84-6.81 (m, 2H), 6.57 (dd, 1H), 6.06 (s, 2H), 5.66 (br s, 1H), 3.10 (quartet, 2H), 1.18 (t, 3H).
LCMS (method A), (M+H⁺) 254, RT=5.19 min.

4-(2-amino-[1,2,4]triazolo[1,5-a]pyridin-6-yl)benzamide

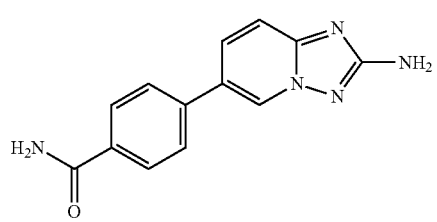 [SMILES: NC(=O)c1ccc(-c2ccc3nc(N)nn3c2)cc1]

¹H NMR (d₆-DMSO) δ 9.01 (s, 1H), 8.07 (s, 1H), 7.97 (d, 2H), 7.88-7.83 (m, 3H), 7.46-7.44 (m, 2H), 6.14 (s, 2H).
LCMS (method A), (M+H⁺) 254, RT=5.02 min.

6-(pyrimidin-5-yl)-[1,2,4]triazolo[1,5-a]pyridin-2-amine hydrochloride

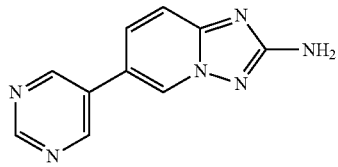 [SMILES: Nc1nc2ccc(-c3cncnc3)cn2n1]

¹H NMR (d₆-DMSO) δ 9.40 (s, 1H), 9.27-9.25 (m, 3H), 8.22 (dd, 1H), 7.56 (d, 1H).
LCMS (method A), (M+H⁺) 213, RT=4.65 min.

6-(1-methyl-1H-pyrazol-4-yl)-[1,2,4]triazolo[1,5-a]pyridin-2-amine hydrochloride

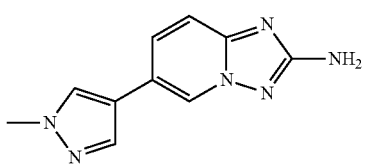 [SMILES: Cn1cc(-c2ccc3nc(N)nn3c2)cn1]

¹H NMR (d₆-DMSO) δ 9.19 (s, 1H), 8.36 (s, 1H), 8.14 (dd, 1H), 8.07 (s, 1H), 7.72 (d, 1H), 3.89 (s, 3H).
LCMS (method A), (M+H⁺) 215, RT=4.80 min.

3-(2-amino-[1,2,4]triazolo[1,5-a]pyridin-6-yl)phenol

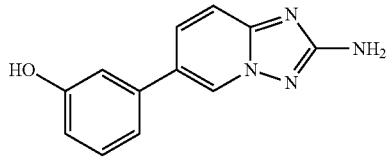 [SMILES: Nc1nc2ccc(-c3cccc(O)c3)cn2n1]

¹H NMR (d₆-DMSO) δ 9.64 (s, 1H), 8.79 (s, 1H), 7.67 (dd, 1H), 7.41 (d, 1H), 7.27 (dd, 1H), 7.12 (d, 1H), 7.06-7.05 (m, 1H), 6.78 (dd, 1H), 6.09 (s, 2H).
LCMS (method A), (M+H⁺) 227, RT=5.96 min.

6-(3-(trifluoromethyl)phenyl)-[1,2,4]triazolo[1,5-a]pyridin-2-amine hydrochloride

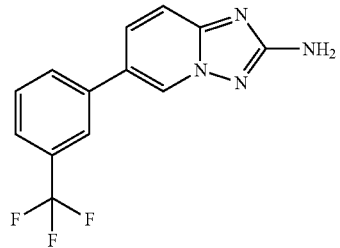 [SMILES: Nc1nc2ccc(-c3cccc(C(F)(F)F)c3)cn2n1]

¹H NMR (d₆-DMSO) δ 9.16 (s, 1H), 8.12 (s, 1H), 8.08 (d, 1H), 7.99 (d, 1H), 7.71-7.78 (m, 2H), 7.54 (d, 1H).
LCMS (method A), (M+H⁺) 279, RT=8.67 min.

6-(benzo[d][1,3]dioxol-5-yl)-[1,2,4]triazolo[1,5-a]pyridin-2-amine hydrochloride

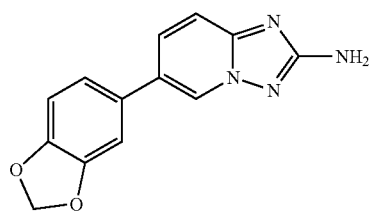 [SMILES: Nc1nc2ccc(-c3ccc4c(c3)OCO4)cn2n1]

¹H NMR (d₆-DMSO) δ 9.03 (s, 1H), 7.99 (d, 1H), 7.57 (d, 1H), 7.41 (d, 1H), 7.26 (dd, 1H), 7.05 (d, 1H), 6.10 (s, 2H), 3.17 (s, 2H).
LCMS (method A), (M+H⁺) 255, RT=7.00 min.

6-(3,4-dimethoxyphenyl)-7-methyl-[1,2,4]triazolo[1,5-a]pyridin-2-amine hydrochloride

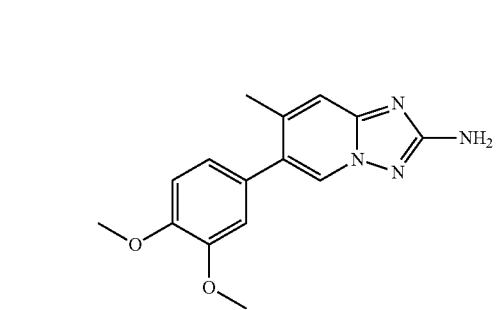 [SMILES: COc1ccc(-c2cn3nc(N)nc3cc2C)cc1OC]

¹H NMR (d₆-DMSO) δ 8.61 (s, 1H), 7.49 (s, 1H), 7.06 (d, 1H), 7.00-7.01 (m, 1H), 6.93-6.98 (m, 1H), 3.81 (s, 3H), 3.80 (s, 3H), 2.35 (s, 3H).
LCMS (method A), (M+H⁺) 285, RT=6.37 min.

6-(3,4-difluorophenyl)-[1,2,4]triazolo[1,5-a]pyridin-2-amine hydrochloride

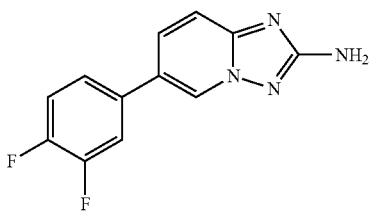 [SMILES: Nc1nc2ccc(-c3ccc(F)c(F)c3)cn2n1]

¹H NMR (d₆-DMSO) δ 9.13 (s, 1H), 8.00 (dd, 1H), 7.93-7.98 (m, 1H), 7.64-7.68 (m, 1H), 7.54-7.57 (m, 2H).
LCMS (method A), (M+H⁺) 247, RT=7.87 min.

6-(3-fluorophenyl)-[1,2,4]triazolo[1,5-a]pyridin-2-amine hydrochloride

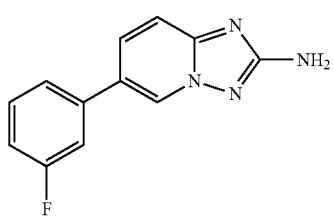 [SMILES: Nc1nc2ccc(-c3cccc(F)c3)cn2n1]

¹H NMR (d₆-DMSO) δ 9.16 (s, 1H), 8.05 (dd, 1H), 7.69 (dt, 1H), 7.65 (d, 1H), 7.60 (d, 1H), 7.52-7.58 (m, 1H), 7.26 (dt, 1H).
LCMS (method A), (M+H⁺) 229, RT=7.55 min.

6-(4-methoxyphenyl)-[1,2,4]triazolo[1,5-a]pyridin-2-amine

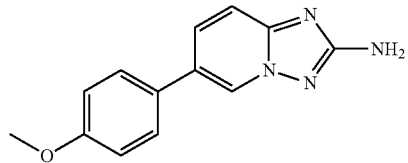 [SMILES: COc1ccc(-c2ccc3nc(N)nn3c2)cc1]

¹H NMR (d₆-DMSO) δ 8.81-8.82 (m, 1H), 7.73 (dd, 1H), 7.67 (d, 2H), 7.40 (d, 1H), 7.03 (d, 2H), 6.05 (s, 2H), 3.80 (s, 3H).

LCMS (method A), (M+H⁺) 241, RT=7.10 min.

N-(3-(2-amino-[1,2,4]triazolo[1,5-a]pyridin-6-yl)phenyl)acetamide

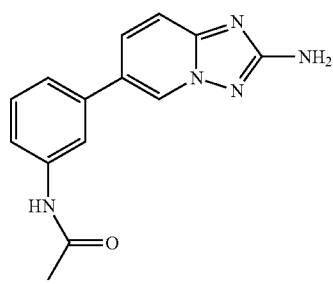 [SMILES: CC(=O)Nc1cccc(-c2ccc3nc(N)nn3c2)c1]

¹H NMR (d₆-DMSO) δ 10.08 (s, 1H), 8.78 (s, 1H), 7.89 (s, 1H), 7.67 (dd, 1H), 7.54-7.59 (m, 1H), 7.45 (d, 1H), 7.37-7.40 (m, 2H), 6.11 (s, 2H), 2.08 (s, 3H).

LCMS (method A), (M+H⁺) 268, RT=5.85 min.

6-(2,3-dihydrobenzo[b][1,4]dioxin-6-yl)-[1,2,4]triazolo[1,5-a]pyridin-2-amine

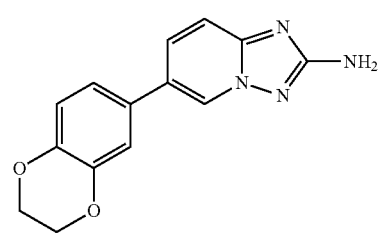 [SMILES: Nc1nc2ccc(-c3ccc4c(c3)OCCO4)cn2n1]

¹H NMR (d₆-DMSO) δ 8.62-8.63 (m, 1H), 7.54 (dd, 1H), 7.21 (d, 1H), 7.08 (d, 1H), 7.02 (dd, 1H), 6.77 (d, 1H), 5.88 (s, 2H), 4.11 (s, 4H).

LCMS (method A), (M+H⁺) 269, RT=7.05 min.

3-(2-amino-[1,2,4]triazolo[1,5-a]pyridin-6-yl)benzenesulfonamide

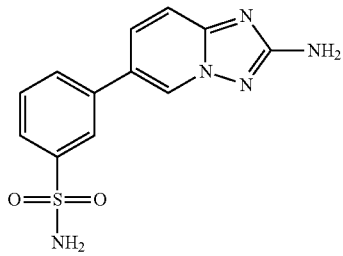 [SMILES: Nc1nc2ccc(-c3cccc(S(N)(=O)=O)c3)cn2n1]

¹H NMR (d₆-DMSO) δ 8.97-8.98 (m, 1H), 8.16 (t, 1H), 7.98-8.00 (m, 1H), 7.79-7.82 (m, 2H), 7.67 (t, 1H), 7.50 (d, 1H), 7.42 (s, 2H), 6.16 (s, 2H).

LCMS (method A), (M+H⁺) 290, RT=5.50 min 4-(2-amino-[1,2,4]triazolo[1,5-a]pyridin-6-yl)benzenesulfonamide

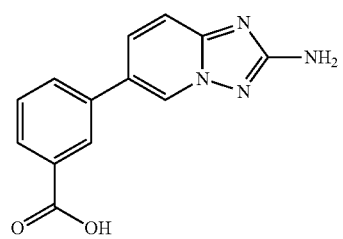 [SMILES: Nc1nc2ccc(-c3cccc(C(=O)O)c3)cn2n1]

¹H NMR (d₆-DMSO) δ 9.03-9.04 (m, 1H), 7.95 (d, 2H), 7.89 (d, 2H), 7.84 (dd, 1H), 7.47 (d, 1H), 7.44 (s, 2H), 6.17 (s, 2H).

LCMS (method A), (M+H⁺) 290, RT=5.38 min 3-(2-amino-[1,2,4]triazolo[1,5-a]pyridin-6-yl)benzoic acid ¹H NMR (d₆-DMSO) δ 8.95-8.96 (m, 1H), 8.20-8.21 (m, 1H), 7.93-7.97 (m, 2H), 7.79 (dd, 1H), 7.57-7.61 (m, 1H), 7.45 (d, 1H), 6.13 (s, 2H).

LCMS (method A), (M+H⁺) 255, RT=1.75 min

6-(pyridin-4-yl)-[1,2,4]triazolo[1,5-a]pyridin-2-amine

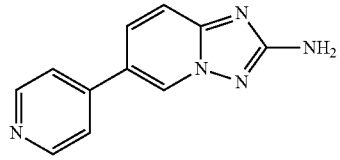 [SMILES: Nc1nc2ccc(-c3ccncc3)cn2n1]

$^1$H NMR (d$_6$-DMSO) δ 9.16-9.16 (m, 1H), 8.63-8.64 (m, 2H), 7.92 (dd, 1H), 7.81-7.83 (m, 2H), 7.48 (dd, 1H), 6.21 (s, 2H).
LCMS (method C), (M+H$^+$) 212, RT=1.89 min

6-(1H-pyrazol-3-yl)-[1,2,4]triazolo[1,5-a]pyridin-2-amine

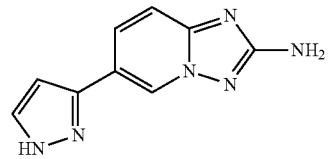 [SMILES: Nc1nc2ccc(-c3cc[nH]n3)cn2n1]

$^1$H NMR (d$_6$-DMSO) δ13.03 (br s, 1H), 8.95 (s, 1H), 7.91 (d, 1H), 7.78 (d, 1H), 7.41 (d, 1H), 6.83 (d, 1H), 6.08 (s, 2H).
LCMS (method A), (M+H$^+$) 201, RT=4.71 min.

6-(thiophen-2-yl)-[1,2,4]triazolo[1,5-a]pyridin-2-amine

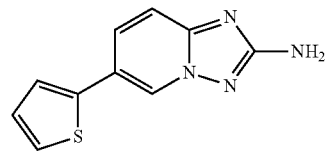 [SMILES: Nc1nc2ccc(-c3cccs3)cn2n1]

$^1$H NMR (d$_6$-DMSO) 68.92 (s, 1H), 7.70 (d, 1H), 7.58 (d, 1H), 7.57 (d, 1H), 7.40 (d, 1H), 7.16 (t, 1H), 6.08 (s, 2H).
LCMS (method A), (M+H$^+$) 217, RT=7.05 min.

6-(1H-pyrazol-4-yl)-[1,2,4]triazolo[1,5-a]pyridin-2-amine

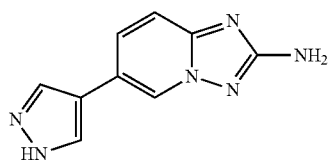 [SMILES: Nc1nc2ccc(-c3cn[nH]c3)cn2n1]

$^1$H NMR (d$_6$-DMSO) δ12.99 (br s, 1H), 8.88 (s, 1H), 8.15 (s, 2H), 7.71 (d, 1H), 7.35 (d, 1H), 5.99 (s, 2H).
LCMS (method A), (M+H$^+$) 201, RT=4.25 min.

Determination of the Effect of the Compounds According to the Invention on PI3K

The compounds of the present invention as described in example 1 can be tested in the PI3K kinobeads assay as described (EP-A 1 887 359). Briefly, test compounds (at various concentrations) and the affinity matrix with the immobilized phenylthiazole ligand 1 are added to cell lysate aliquots and allowed to bind to the proteins in the lysate sample. After the incubation time the beads with captured proteins are separated from the lysate. Bound proteins are then eluted and the presence of PI3K gamma is detected and quantified using a specific antibody in a dot blot procedure and the Odyssey infrared detection system.

Conventionally, PI3K lipid kinase activity can be measured using purified or recombinant enzyme in a solution-based assay with phopholipid vesicles.

The reaction is terminated by the addition of acidified organic solvents and subsequent phase separation by extraction or thin layer chromatography analysis (Carpenter et al., 1990, J. Biol. Chem. 265, 19704-19711).

Another assay described in the art is based on the phosphate transfer from radiolabeled ATP to phosphatidylinositol immobilized on plates. This assay type also uses recombinant PI3K gamma enzyme but can be performed in a high throughput mode (Fuchikami et al., 2002, J. Biomol. Screening 7, 441-450).

In general, compounds of the invention are effective for the inhibition of PI3K gamma, with an IC$_{50}$ of <10 μM.

The invention claimed is:

1. A pharmaceutical composition comprising a compound of formula (I)

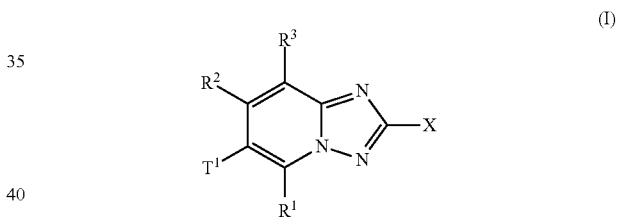

or a pharmaceutically acceptable salt thereof, wherein
X is NH$_2$;
R$^1$, R$^2$, R$^3$ are independently selected from the group consisting of H; halogen; CN; C(O)OR$^4$; OR$^4$; C(O)R$^4$; C(O)N(R$^4$R$^{4a}$); S(O)$_2$N(R$^4$R$^{4a}$); S(O)N(R$^4$R$^{4a}$); S(O)$_2$R$^4$; S(O)R$^4$; N(R$^4$)S(O)$_2$N(R$^{4a}$R$^{4b}$); N(R$^4$)S(O)N(R$^{4a}$R$^{4b}$); SR$^4$; N(R$^4$R$^{4a}$); OC(O)R$^4$; N(R$^4$)C(O)R$^{4a}$; N(R$^4$)S(O)$_2$R$^{4a}$; N(R$^4$)S(O)R$^{4a}$; N(R$^4$)C(O)N(R$^{4a}$R$^{4b}$); N(R$^4$)C(O)OR$^{4a}$; OC(O)N(R$^4$R$^{4a}$); and C$_{1-6}$ alkyl, wherein C$_{1-6}$ alkyl is optionally substituted with one or more halogen, which are the same or different;
R$^4$, R$^{4a}$, R$^{4b}$ are independently selected from the group consisting of H; and
C$_{1-6}$ alkyl, wherein C$_{1-6}$ alkyl is optionally substituted with one or more halogen, which are the same or different;
T$^1$ is 4 to 7 membered heterocyclyl; 9 to 11 membered heterobicyclyl; phenyl; naphthyl; indenyl; or indanyl; wherein T$^1$ is optionally substituted with one or more R$^5$ and/or one or more R$^6$;
R$^5$ is halogen; CN; C(O)OR$^7$; OR$^7$; oxo (=O), where the ring is at least partially saturated; C(O)R$^7$; C(O)N(R$^7$R$^{7a}$); S(O)$_2$N(R$^7$R$^{7a}$); S(O)N(R$^7$R$^{7a}$); S(O)$_2$R$^7$; S(O)R$^7$; N(R$^7$)S(O)$_2$N(R$^{7a}$R$^{7b}$); N(R$^7$)S(O)N(R$^{7a}$R$^{7b}$); SR$^7$; N(R$^7$R$^{7a}$); OC(O)R$^7$; N(R$^7$)C(O)R$^7$; N(R$^7$)S(O)$_2$R$^{7a}$; N(R$^7$)S(O)R$^{7a}$; N(R$^7$)C(O)N(R$^{7a}$R$^{7b}$); N(R$^7$)C (O)OR$^{7a}$; OC(O)N(R$^7$R$^{7a}$); or C$_{1-6}$ alkyl, wherein C$_{1-6}$ alkyl is optionally substituted with one or more R$^8$;

R$^6$ is T$^2$; C(O)OR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); N(R$^9$)S(O)N(R$^{9a}$R$^{9b}$); SR$^9$; N(R$^9$R$^{9a}$); OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)N(R$^{9a}$R$^{9b}$); N(R$^9$)C(O)OR$^{9a}$; OC(O)N(R$^9$R$^{9a}$); or C$_{1-6}$ alkyl substituted with one or more T$^2$ and optionally substituted with one or more R$^8$;

R$^9$, R$^{9a}$, R$^{9b}$ are independently selected from the group consisting of R$^{9c}$; and R$^{9d}$, provided that at least one of R$^9$, R$^{9a}$, R$^{9b}$ is R$^{9c}$;

R$^{9c}$ is T$^2$; or C$_{1-6}$ alkyl, wherein C$_{1-6}$ alkyl is substituted with one or more T$^2$ and optionally substituted with one or more R$^8$;

R$^7$, R$^{7a}$, R$^{7b}$, R$^{9d}$ are independently selected from the group consisting of H; and C$_{1-6}$ alkyl, wherein C$_{1-6}$ alkyl is optionally substituted with one or more R$^8$;

R$^8$ is halogen; CN; C(O)OR$^{10}$; OR$^{10}$; C(O)R$^{10}$; C(O)N(R$^{10}$R$^{10a}$); S(O)$_2$N(R$^{10}$R$^{10a}$); S(O)N(R$^{10}$R$^{10a}$); S(O)$_2$R$^{10}$; S(O)R$^{10}$; N(R$^{10}$)S(O)$_2$N(R$^{10a}$R$^{10b}$); N(R$^{10}$)S(O)N(R$^{10a}$R$^{10b}$); SR$^{10}$; N(R$^{10}$R$^{10a}$); OC(O)R$^{10}$; N(R$^{10}$)C(O)R$^{10a}$; N(R$^{10}$)S(O)$_2$R$^{10a}$; N(R$^{10}$)S(O)R$^{10a}$; N(R$^{10}$)C(O)N(R$^{10a}$R$^{10b}$); N(R$^{10}$)C(O)OR$^{10a}$; OC(O)N(R$^{10}$R$^{10a}$); or C$_{1-6}$ alkyl, wherein C$_{1-6}$ alkyl is optionally substituted with one or more halogen, which are the same or different;

R$^{10}$; R$^{10a}$; R$^{10b}$ are independently selected from the group consisting of H; and C$_{1-6}$ alkyl, wherein C$_{1-6}$ alkyl is optionally substituted with one or more halogen, which are the same or different;

T$^2$ is C$_{3-7}$ cycloalkyl; 4 to 7 membered heterocyclyl; 9 to 11 membered heterobicyclyl;

phenyl; naphthyl; indenyl; or indanyl, wherein T$^2$ is optionally substituted with one or more R$^{11}$;

R$^{11}$ is halogen; CN; C(O)OR$^{12}$; OR$^{12}$; oxo (=O), where the ring is at least partially saturated; C(O)R$^{12}$; C(O)N(R$^{12}$R$^{12a}$); S(O)$_2$N(R$^{12}$R$^{12a}$); S(O)N(R$^{12}$R$^{12a}$); S(O)$^2$R$^{12}$; S(O)R$^{12}$; N(R$^{12}$)S(O)$_2$N(R$^{12a}$R$^{12b}$); N(R$^{12}$)S(O)N(R$^{12a}$R$^{12b}$); SR$^{12}$; N(R$^{12}$R$^{12a}$); OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)N(R$^{12a}$R$^{12b}$); N(R$^{12}$)C(O)OR$^{12a}$; OC(O)N(R$^{12}$R$^{12a}$); or C$_{1-6}$ alkyl, wherein C$_{1-6}$ alkyl is optionally substituted with one or more halogen which are the same or different;

R$^{12}$; R$^{12a}$, R$^{12b}$ are independently selected from the group consisting of H; and C$_{1-6}$ alkyl, wherein C$_{1-6}$ alkyl is optionally substituted with one or more halogen, which are the same or different, together with a pharmaceutically acceptable carrier.

2. A pharmaceutical composition according to claim 1, wherein R$^1$ and R$^2$ are independently H or CH$_3$.

3. A pharmaceutical composition according to claim 1, wherein R$^3$ is H, CH$_3$ or halogen.

4. A pharmaceutical composition according to claim 1, wherein T$^1$ is unsubstituted phenyl; substituted phenyl; unsubstituted 4 to 7 membered heterocyclyl; substituted 4 to 7 membered heterocyclyl; unsubstituted 9 to 11 membered heterobicyclyl; or substituted 9 to 11 membered heterobicyclyl.

5. A pharmaceutical composition according to claim 1, wherein T$^1$ is unsubstituted, substituted with one R$^5$, two R$^5$, one R$^6$, two R$^6$, or one R$^5$ and one R$^6$.

6. A pharmaceutical composition according to claim 1, wherein T$^1$ is phenyl; pyrrolyl; furyl; thienyl; pyrazolyl; oxazolyl; thiazolyl; pyridyl and N-oxide thereof; pyrimidinyl; indolyl; indolinyl; indazolyl; quinolinyl; isoquinolinyl; benzodioxolyl; dihydrobenzofuryl; dihydrobenzoxazinyl; dihydrobenzodioxinyl; benzodioxanyl; or benzothiazole dioxide.

7. A pharmaceutical composition according to claim 1, wherein T$^1$ is phenyl or pyridyl.

8. A pharmaceutical composition according to claim 1, wherein R$^5$ is oxo (=O), where the ring is at least partially substituted; F; Cl; CN; N(R$^7$R$^{7a}$); OR$^7$; C(O)OR$^7$; C(O)N(R$^7$R$^{7a}$); N(R$^7$)S(O)$_2$R$^{7a}$; S(O)$_2$N(R$^7$R$^{7a}$); S(O)$_2$R$^7$; S(O)R$^7$; N(R$^7$)C(O)R$^{7a}$; or C$_{1-6}$ alkyl, which is optionally substituted with one or more R$^8$.

9. A pharmaceutical composition according to claim 1, wherein R$^7$, R$^{7a}$ are independently selected from the group consisting of H; CH$_3$; CH$_2$CH$_3$; n-butyl; tert.-butyl; iso-propyl; n-pentyl; isopentyl; neopentyl; 2-ethylbutyl; CF$_3$; CH$_2$CH$_2$OH; CH$_2$CH$_2$CH$_2$OH; CH$_2$C(CH$_3$)$_2$CH$_2$OH; CH$_2$CH$_2$OCH$_3$; CH$_2$CH$_2$NH$_2$; CH$_2$CF$_3$; CH$_2$CH$_2$CF$_3$; CH$_2$CH$_2$CH$_2$CF$_3$; C(CH$_3$)$_2$CF$_3$; CH$_2$CH$_2$NHCH$_3$; CH$_2$CH$_2$N(CH$_3$)$_2$; CH$_2$CH$_2$CH$_2$N(CH$_3$)$_2$; CH$_2$C(O)OH; and CH$_2$C(O)N(CH$_3$)$_2$.

10. A pharmaceutical composition according to claim 1, wherein R$^8$ is F; Cl; Br; OH; CH$_3$; or CH$_2$CH$_3$.

11. A pharmaceutical composition according to claim 1, wherein R$^5$ is oxo (=O), where the ring is at least partially substituted; F; Cl; NH$_2$; NH(CH$_3$); N(CH$_3$)$_2$; NH(CH$_2$)$_2$OH; N((CH$_2$)$_2$OH)$_2$; OH; OCH$_3$; OCF$_3$; OCH(CH$_3$)$_2$; CH$_2$OH; CH$_2$OCH$_3$; CH$_2$Br; CH$_3$; CH$_2$CH$_3$; CH(CH$_3$)$_2$; C(CH$_3$)$_3$; CF$_3$; C(O)OH; C(O)OCH$_3$; C(O)OCH$_2$CH$_3$; C(O)NH$_2$; C(O)NH(CH$_3$); C(O)(CH$_3$)$_2$; C(O)NHCH$_2$CH$_3$; C(O)N(CH$_3$)CH$_2$CH$_3$; C(O)NHCH$_2$CH$_2$OH; C(O)N(CH$_3$)CH$_2$CH$_2$OH; C(O)NHCH$_2$CH$_2$OCH$_3$; C(O)N(CH$_3$)CH$_2$CH$_2$OCH$_3$; C(O)NHCH$_2$CH$_2$NH$_2$; C(O)N(CH$_3$)CH$_2$CH$_2$NH$_2$; C(O)NHCH$_2$CH$_2$NHCH$_3$; C(O)N(CH$_3$)CH$_2$CH$_2$NHCH$_3$; C(O)NHCH$_2$CH$_2$N(CH$_3$)$_2$; C(O)N(CH$_3$)CH$_2$CH$_2$N(CH$_3$)$_2$; HNC(O)H$_3$; S(O)$_2$CH$_3$; S(O)CH$_3$; S(O)$_2$NH$_2$; S(O)$_2$NHC(CH$_3$)$_3$; S(O)$_2$NHCH$_2$CH(CH$_2$CH$_3$)$_2$; S(O)$_2$NH(CH$_2$)$_2$OH; S(O)$_2$NH(CH$_2$)$_2$CF$_3$; S(O)$_2$NH(CH$_2$)$_3$CF$_3$; S(O)$_2$NH(CH$_2$)$_3$OH; S(O)$_2$NHCH$_2$C(CH$_3$)$_2$CH$_2$OH; S(O)$_2$NH(CH$_2$)$_2$OCH$_3$; or NHS(O)$_2$CH$_3$.

12. A pharmaceutical composition according to claim 1, wherein R$^6$ is S(O)$_2$N(R$^9$R$^{9a}$); N(R$^9$)S(O)$_2$R$^{9a}$; S(O)$_2$R$^9$; OR$^9$; or SR$^9$.

13. A pharmaceutical composition according to claim 1, wherein R$^6$ is S(O)$_2$N(R$^{9c}$R$^{9d}$); N(R$^{9d}$)S(O)$_2$R$^{9c}$; S(O)$_2$R$^{9c}$; or OR$^{9c}$.

14. A pharmaceutical composition according to claim 1, wherein R$^{9c}$ is T$^2$; CH$_2$-T$^2$; or C$_{1-4}$ alkyl-T$^2$.

15. A pharmaceutical composition according to claim 1, wherein R$^{9d}$ is H or methyl.

16. A pharmaceutical composition according to claim 1, wherein T$^2$ is phenyl; naphthyl; C$_{3-4}$ cycloalkyl; or 4 to 7 membered heterocyclyl, wherein T$^2$ is optionally substituted with up to three R$^{11}$.

17. A pharmaceutical composition according to claim 1, wherein T$^2$ is azetidinyl; imidazolidinyl; pyrrolidinyl; piperidinyl; piperizinyl; isoindolinyl; oxazolyl; dihydroisoquinolinyl; morpholinyl; pyranyl; azepanyl; azetidinyl; thiamorpholine dioxide; cyclopropyl; cyclobutyl; cyclopentyl; cyclohexyl; cycloheptyl; phenyl; or naphthyl.

18. A pharmaceutical composition according to claim 1, wherein R$^{11}$ is oxo (=O), where the ring is at least partially saturated; F; Cl; CH$_3$; CH$_2$CH$_3$; CH$_2$CH$_2$CH$_3$; CH(CH$_3$)$_2$; CF$_3$; OH; OCH$_3$; OCF$_3$; NH$_2$; NHCH$_3$; N(CH$_3$)$_2$.

19. A pharmaceutical composition according to claim 1 of formula (Ia)

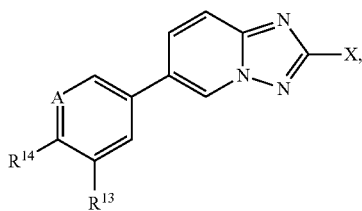

wherein
X has the meaning as indicated in claim 1;
A is CH; or N;
$R^{14}$ is H; or $R^5$;
$R^{13}$ is H; $R^5$; or $R^6$.

20. A pharmaceutical composition according to claim 19, wherein $R^{13}$ is $R^5$ or $R^6$.

21. A pharmaceutical composition according to claim 19, wherein $R^{13}$ is H; OH; or $OCH_3$.

22. A pharmaceutical composition according to claim 1 wherein the compound of formula (I) or pharmaceutically acceptable salt thereof is selected from the group consisting of:

3-(2-Amino-[1,2,4]triazolo[1,5-a]pyridin-6-yl)-N-(2-hydroxy-ethyl)-benzenesulfonamide;
6-(5-Methanesulfonyl-pyridin-3-yl)-[1,2,4]triazolo[1,5-a]pyridin-2-ylamine;
5-(2-Amino-[1,2,4]triazolo[1,5-a]pyridin-6-yl)-pyridine-3-sulfonic acid butylamide;
5-(2-Amino-[1,2,4]triazolo[1,5-a]pyridin-6-yl)-2-methoxy-phenol;
5-(2-Amino-[1,2,4]triazolo[1,5-a]pyridin-6-yl)-pyridine-3-sulfonic acid tert-butylamide;
5-(2-Amino-[1,2,4]triazolo[1,5-a]pyridin-6-yl)-pyridine-3-sulfonic acid benzylamide;
5-(2-Amino-[1,2,4]triazolo[1,5-a]pyridin-6-yl)-pyridine-3-sulfonic acid (2-ethyl-butyl)-amide;
5-(2-Amino-[1,2,4]triazolo[1,5-a]pyridin-6-yl)-pyridine-3-sulfonic acid (4-chloro-phenyl)-amide;
5-(2-Amino-[1,2,4]triazolo[1,5-a]pyridin-6-yl)-pyridine-3-sulfonic acid (3,5-bis-trifluoromethyl-phenyl)-amide;
5-(2-Amino-[1,2,4]triazolo[1,5-a]pyridin-6-yl)-pyridine-3-sulfonic acid (4-fluoro-phenyl)-amide;
6-(3-Methanesulfonyl-phenyl)-[1,2,4]triazolo[1,5-a]pyridin-2-ylamine;
6-(3,4-dimethoxyphenyl)-[1,2,4]triazolo[1,5-a]pyridin-2-amine;
3-(2-amino-[1,2,4]triazolo[1,5-a]pyridin-6-yl)-N-(2-aminoethyl)benzenesulfonamide;
6-(3-isopropoxy-4-methoxyphenyl)-[1,2,4]triazolo[1,5-a]pyridin-2-amine;
4-(2-Amino-[1,2,4]triazolo[1,5-a]pyridin-6-yl)-2-methoxyphenol;
3-(2-Amino-[1,2,4]triazolo[1,5-a]pyridin-6-yl)-N-butyl-benzenesulfonamide;
4,4,4-Trifluorobutane-1-sulfonic acid [5-(2-amino-[1,2,4]triazolo[1,5-a]pyridin-6-yl)-pyridin-3-yl]amide;
N-[5-(2-Amino-[1,2,4]triazolo[1,5-a]pyridin-6-yl)-pyridin-3-yl]-3-trifluoromethylbenzenesulfonamide HCl salt;
N-[5-(2-Amino-[1,2,4]triazolo[1,5-a]pyridin-6-yl)-pyridin-3-yl]-2-trifluoromethylbenzenesulfonamide HCl salt;
N-[5-(2-Amino-[1,2,4]triazolo[1,5-a]pyridin-6-yl)-pyridin-3-yl]-4-trifluoromethylbenzenesulfonamide HCl salt;
Naphthalene-2-sulfonic acid [5-(2-amino-[1,2,4]triazolo[1,5-a]pyridin-6-yl)-pyridin-3-yl]-amide HCl salt;
N-[5-(2-Amino-[1,2,4]triazolo[1,5-a]pyridin-6-yl)-pyridin-3-yl]-4-isopropylbenzenesulfonamide HCl salt;
Naphthalene-1-sulfonic acid [5-(2-amino-[1,2,4]triazolo[1,5-a]pyridin-6-yl)-pyridin-3-yl]-amide HCl salt;
N-[5-(2-Amino-[1,2,4]triazolo[1,5-a]pyridin-6-yl)-pyridin-3-yl]-4-chlorobenzenesulfonamide HCl salt;
6-(3,4-Dimethoxyphenyl)-8-chloro-[1,2,4]triazolo[1,5-a]pyridine-2-ylamine;
N-[5-(2-Amino-[1,2,4]triazolo[1,5-a]pyridin-6-yl)pyridine-3-yl]-3-trifluoromethoxybenzenesulfonamide HCl;
N-[5-(2-Amino-[1,2,4]triazolo[1,5-a]pyridin-6-yl)pyridine-3-yl]-C-(2-trifluoromethylphenyl)methanesulfonamide HCl;
N-[5-(2-Amino-[1,2,4]triazolo[1,5-a]pyridin-6-yl)pyridine-3-yl]-C-(4-trifluoromethylphenyl)methanesulfonamide HCl;
N-[5-(2-Amino-[1,2,4]triazolo[1,5-a]pyridin-6-yl)pyridine-3-yl]-C-(4-chlorophenyl)methanesulfonamide HCl;
N-[5-(2-Amino-[1,2,4]triazolo[1,5-a]pyridin-6-yl)-pyridin-3-yl]-3,5-bis-trifluoromethylbenzenesulfonamide;
5-(2-amino-[1,2,4]triazolo[1,5-a]pyridin-6-yl)-N-(4-(trifluoromethyl)phenyl)pyridine-3-sulfonamide;
5-(2-amino-[1,2,4]triazolo[1,5-a]pyridin-6-yl)-N-(2-(trifluoromethyl)phenyl)pyridine-3-sulfonamide;
5-(2-amino-[1,2,4]triazolo[1,5-a]pyridin-6-yl)-N-(3-(trifluoromethyl)phenyl)pyridine-3-sulfonamide;
5-(2-amino-[1,2,4]triazolo[1,5-a]pyridin-6-yl)-N-methyl-N-(3-(trifluoromethyl)phenyl)pyridine-3-sulfonamide;
5-(2-amino-[1,2,4]triazolo[1,5-a]pyridin-6-yl)-N-(4-(trifluoromethoxy)phenyl)pyridine-3-sulfonamide;
5-(2-amino-[1,2,4]triazolo[1,5-a]pyridin-6-yl)-N-phenylpyridine-3-sulfonamide;
5-(2-amino-[1,2,4]triazolo[1,5-a]pyridin-6-yl)-N-(3-(trifluoromethoxy)phenyl)pyridine-3-sulfonamide;
5-(2-amino-[1,2,4]triazolo[1,5-a]pyridin-6-yl)-N-(3-(1,1,2,2-tetrafluoroethoxy)phenyl)pyridine-3-sulfonamide;
5-(2-amino-[1,2,4]triazolo[1,5-a]pyridin-6-yl)-N-(3-(difluoromethoxy)phenyl)pyridine-3-sulfonamide;
5-(2-amino-[1,2,4]triazolo[1,5-a]pyridin-6-yl)-N-(4-(difluoromethoxy)phenyl)pyridine-3-sulfonamide;
6-(5-(trifluoromethyl)pyridin-3-yl)-[1,2,4]triazolo[1,5-a]pyridin-2-amine;
6-(4-isopropoxy-3-methoxyphenyl)-[1,2,4]triazolo[1,5-a]pyridin-2-amine;
5-(2-amino-[1,2,4]triazolo[1,5-a]pyridine-6-yl)-N-(2-methyl-1-(pyrrolidin-1-yl)propan-2-yl)pyridine-3-sulfonamide;
6-(5-(4-fluoropiperidin-1-ylsulfonyl)pyridine-3-yl)-[1,2,4]triazolo[1,5-a]pyridine-2-amine;
6-(5-(4-methylpiperizin-1-ylsulfonyl)pyridine-3-yl)-[1,2,4]triazolo[1,5-a]pyridine-2-amine;
2-(5-(2-amino-[1,2,4]triazolo[1,5-a]pyridine-6-yl)pyridine-3-sulfoamido)-N,N-dimethylacetamide;
5-(2-amino-[1,2,4]triazolo[1,5-a]pyridine-6-yl)-N-(2-(oxoimidazolidin-1-yl)ethyl)pyridine-3-sulfonamide;
5-(2-amino-[1,2,4]triazolo[1,5-a]pyridine-6-yl)-N-(2-(dimethylamino)ethyl)-N-methylpyridine-3-sulfonamide;
5-(2-amino-[1,2,4]triazolo[1,5-a]pyridine-6-yl)-N-(3-(dimethylamino)propyl)pyridine-3-sulfonamide;
5-(2-amino-[1,2,4]triazolo[1,5-a]pyridine-6-yl)-N-butyl-N-methylpyridine-3-sulfonamide;

5-(2-amino-[1,2,4]triazolo[1,5-a]pyridine-6-yl)-N-isopentylpyridine-3-sulfonamide;
5-(2-amino-[1,2,4]triazolo[1,5-a]pyridine-6-yl)-N-(cyclopropylmethyl)pyridine-3-sulfonamide;
6-(5-isoindolin-2-ylsulfonyl)pyridine-3-yl)-[1,2,4]triazolo[1,5-a]pyridin-2-amine;
6-(5-piperazin-1-ylsulfonyl)pyridine-3-yl)-[1,2,4]triazolo[1,5-a]pyridin-2-amine;
5-(2-amino-[1,2,4]triazolo[1,5-a]pyridine-6-yl)-N-benzyl-N-methylpyridine-3-sulfonamide;
5-(2-amino-[1,2,4]triazolo[1,5-a]pyridine-6-yl)-N-(2,4-dimethyloxazol-5-yl)methyl)pyridine-3-sulfonamide;
5-(2-amino-[1,2,4]triazolo[1,5-a]pyridine-6-yl)-N-benzyl-N-butylpyridine-3-sulfonamide;
6-(5-(3,4-dihydroisoquinolin-2(1H)-ylsulfonyl)pyridine-3-yl-[1,2,4]triazolo[1,5-a]pyridin-amine;
5-(2-amino-[1,2,4]triazolo[1,5-a]pyridine-6-yl)-N-(2,3-dichlorobenzyl)-N-methylpyridine-3-sulfonamide;
5-(2-amino-[1,2,4]triazolo[1,5-a]pyridine-6-yl)-N-cyclopropyl-N-(2-fluorobenzyl)pyridine-3-sulfonamide;
5-(2-amino-[1,2,4]triazolo[1,5-a]pyridine-6-yl)-N-(2-phenylpropan-2-yl)pyridine-3-sulfonamide;
5-(2-amino-[1,2,4]triazolo[1,5-a]pyridine-6-yl)-N-(2-(4-fluorophenyl)propan-2-yl)pyridine-3-sulfonamide;
5-(2-amino-[1,2,4]triazolo[1,5-a]pyridine-6-yl)-N-(4-fluorobenzyl)pyridine-3-sulfonamide;
5-(2-amino-[1,2,4]triazolo[1,5-a]pyridine-6-yl)-N,N-diethylpyridine-3-sulfonamide;
5-(2-amino-[1,2,4]triazolo[1,5-a]pyridine-6-yl)-N-(1,1,1-trifluoro-2-methylpropan-2-yl)pyridine-3-sulfonamide;
5-(2-amino-[1,2,4]triazolo[1,5-a]pyridine-6-yl)pyridine-3-sulfonamide;
5-(2-amino-[1,2,4]triazolo[1,5-a]pyridine-6-yl)-N-butylpyridine-3-sulfonamide;
6-(5-(morpholinosulfonyl)pyridin-3-yl)-[1,2,4]triazolo[1,5-a]pyridin-2-amine;
5-(2-amino-[1,2,4]triazolo[1,5-a]pyridine-6-yl)-N-(3,3,3-trifluoropropyl)pyridine-3-sulfonamide;
5-(2-amino-[1,2,4]triazolo[1,5-a]pyridine-6-yl)-N,N-dimethylpyridine-3-sulfonamide;
5-(2-amino-[1,2,4]triazolo[1,5-a]pyridine-6-yl)-N-neopentylpyridine-3-sulfonamide;
5-(2-amino-[1,2,4]triazolo[1,5-a]pyridine-6-yl)-N-cyclopentylpyridine-3-sulfonamide;
5-(2-amino-[1,2,4]triazolo[1,5-a]pyridine-6-yl)-N-(3,4-dichlorobenzyl)pyridine-3-sulfonamide;
3-(2-amino-[1,2,4]triazolo[1,5-a]pyridine-6-yl)-N-(2-(dimethylamino)ethyl)benzenesulfonamide;
3-(2-amino-[1,2,4]triazolo[1,5-a]pyridine-6-yl)-N-(2-(dimethylamino)ethyl)-N-methylbenzenesulfonamide;
3-(2-amino-[1,2,4]triazolo[1,5-a]pyridine-6-yl)-N-tert-butylbenzenesulfonamide;
2-(3-(2-amino-[1,2,4]triazolo[1,5-a]pyridine-6-yl)phenylsulfonamido)acetic acid;
3-(2-amino-[1,2,4]triazolo[1,5-a]pyridine-6-yl)-N-(3-(dimethylamino)propyl)benzenesulfonamide;
6-(5-chloropyridin-3-yl)-[1,2,4]triazolo[1,5-a]pyridin-2-amine;
5-(2-amino-[1,2,4]triazolo[1,5-a]pyridine-6-yl)-N-cyclopropylpyridine-3-sulfonamide;
6-(5-(pyrrolidin-1-ylsulfonyl)pyridin-3-yl)-[1,2,4]triazolo[1,5-a]pyridin-2-amine;
5-(2-amino-[1,2,4]triazolo[1,5-a]pyridine-6-yl)-N-tert-butyl-N-methylpyridine-3-sulfonamide;
6-(5-(piperidin-1-ylsulfonyl)pyridin-3-yl)-[1,2,4]triazolo[1,5-a]pyridin-2-amine;
5-(2-amino-[1,2,4]triazolo[1,5-a]pyridin-6-yl)-N-isobutylpyridine-3-sulfonamide;
5-(2-amino-[1,2,4]triazolo[1,5-a]pyridin-6-yl)-N-isopropylpyridine-3-sulfonamide;
5-(2-amino-[1,2,4]triazolo[1,5-a]pyridin-6-yl)-N-(2,3-dichlorobenzyl)pyridine-3-sulfonamide;
5-(2-amino-[1,2,4]triazolo[1,5-a]pyridin-6-yl)-N-propylpyridine-3-sulfonamide;
5-(2-amino-[1,2,4]triazolo[1,5-a]pyridin-6-yl)-N-(2,2,2-trifluoroethyl)pyridine-3-sulfonamide;
5-(2-amino-[1,2,4]triazolo[1,5-a]pyridin-6-yl)-N-cyclohexylpyridine-3-sulfonamide;
5-(2-amino-[1,2,4]triazolo[1,5-a]pyridin-6-yl)-N-(tetrahydro-2H-pyran-4-yl)pyridine-3-sulfonamide;
5-(2-amino-[1,2,4]triazolo[1,5-a]pyridin-6-yl)-N-((tetrahydro-2H-pyran-4-yl)methyl)pyridine-3-sulfonamide;
5-(2-amino-[1,2,4]triazolo[1,5-a]pyridin-6-yl)-N-(4-hydroxycyclohexyl)pyridine-3-sulfonamide;
6-(5-(4,4-difluoropiperidin-1-ylsulfonyl)pyridin-3-yl)-[1,2,4]triazolo[1,5-a]pyridin-2-amine;
6-(5-(azepan-1-ylsulfonyl)pyridin-3-yl)-[1,2,4]triazolo[1,5-a]pyridin-2-amine;
6-(5-(azetidin-1-ylsulfonyl)pyridin-3-yl)-[1,2,4]triazolo[1,5-a]pyridin-2-amine;
5-(2-amino-[1,2,4]triazolo[1,5-a]pyridin-6-yl)-N-(cyclobutylmethyl)pyridine-3-sulfonamide;
5-(2-amino-[1,2,4]triazolo[1,5-a]pyridin-6-yl)-N-ethylpyridine-3-sulfonamide;
5-(2-amino-[1,2,4]triazolo[1,5-a]pyridin-6-yl)-N-methylpyridine-3-sulfonamide;
6-(3,4-dimethoxyphenyl)-8-fluoro-[1,2,4]triazolo[1,5-a]pyridin-2-amine;
6-(3,4-dimethoxyphenyl)-8-methyl-[1,2,4]triazolo[1,5-a]pyridin-2-amine;
6-(5-(benzylsulfonyl)pyridin-3-yl)-[1,2,4]triazolo[1,5-a]pyridin-2-amine;
6-(5-(tert-Butylsulfonyl)pyridin-3-yl)-[1,2,4]triazolo[1,5-a]pyridin-2-amine;
5-(2-amino-[1,2,4]triazolo[1,5-a]pyridin-6-yl)-N-ethyl-N-methylpyridine-3-sulfonamide;
5-(2-amino-8-fluoro-[1,2,4]triazolo[1,5-a]pyridin-6-yl)-N-tert-butylpyridine-3-sulfonamide;
6-(5-isobutoxypyridin-3-yl)-[1,2,4]triazolo[1,5-a]pyridin-2-amine;
6-(5-(benzyloxy)pyridin-3-yl)-[1,2,4]triazolo[1,5-a]pyridin-2-amine;
6-(5-phenoxypyridin-3-yl)-[1,2,4]triazolo[1,5-a]pyridin-2-amine;
6-(5-(neopentyloxy)pyridin-3-yl)-[1,2,4]triazolo[1,5-a]pyridin-2-amine;
6-(5-(neopentylsulfonyl)pyridin-3-yl)-[1,2,4]triazolo[1,5-a]pyridin-2-amine;
5-(2-amino-[1,2,4]triazolo[1,5-a]pyridin-6-yl)-N-(cyclopentylmethyl)pyridine-3-sulfonamide;
5-(2-amino-[1,2,4]triazolo[1,5-a]pyridin-6-yl)-N-(cycloheptylmethyl)pyridine-3-sulfonamide;
5-(2-amino-[1,2,4]triazolo[1,5-a]pyridin-6-yl)-N-(3-isopropylphenyl)pyridine-3-sulfonamide;
5-(2-amino-[1,2,4]triazolo[1,5-a]pyridin-6-yl)-N-(2-fluorophenyl)pyridine-3-sulfonamide;
5-(2-amino-[1,2,4]triazolo[1,5-a]pyridin-6-yl)-N-(4-isopropylphenyl)pyridine-3-sulfonamide;
5-(2-amino-[1,2,4]triazolo[1,5-a]pyridin-6-yl)-N-(2-methoxyphenyl)pyridine-3-sulfonamide;
5-(2-amino-[1,2,4]triazolo[1,5-a]pyridin-6-yl)-N-(2,4-difluorophenyl)pyridine-3-sulfonamide;

5-(2-amino-[1,2,4]triazolo[1,5-a]pyridin-6-yl)-N-tert-butylnicotinamide;
5-(2-amino-[1,2,4]triazolo[1,5-a]pyridin-6-yl)-N-(4-methoxyphenyl)pyridine-3-sulfonamide;
5-(2-amino-[1,2,4]triazolo[1,5-a]pyridin-6-yl)-N-(3-fluorophenyl)pyridine-3-sulfonamide;
5-(2-amino-[1,2,4]triazolo[1,5-a]pyridin-6-yl)-N-(3,4-difluorophenyl)pyridine-3-sulfonamide;
5-(2-amino-[1,2,4]triazolo[1,5-a]pyridin-6-yl)-N-(2-isopropylphenyl)pyridine-3-sulfonamide;
5-(2-amino-[1,2,4]triazolo[1,5-a]pyridin-6-yl)-N-(3,5-difluorophenyl)pyridine-3-sulfonamide;
5-(2-amino-[1,2,4]triazolo[1,5-a]pyridin-6-yl)-N-(3-methoxyphenyl)pyridine-3-sulfonamide;
5-(2-amino-[1,2,4]triazolo[1,5-a]pyridin-6-yl)-N-(2,3-difluorophenyl)pyridine-3-sulfonamide;
5-(2-amino-[1,2,4]triazolo[1,5-a]pyridin-6-yl)-N-(1-methylcyclobutyl)pyridine-3-sulfonamide;
5-(2-amino-[1,2,4]triazolo[1,5-a]pyridin-6-yl)-N-(2-aminoethyl)pyridine-3-sulfonamide;
5-(2-amino-8-fluoro-[1,2,4]triazolo[1,5-a]pyridin-6-yl)-N-methylpyridine-3-sulfonamide;
5-(2-amino-8-fluoro-[1,2,4]triazolo[1,5-a]pyridin-6-yl)-N-isopropylpyridine-3-sulfonamide;
5-(2-amino-8-fluoro-[1,2,4]triazolo[1,5-a]pyridin-6-yl)-N-propylpyridine-3-sulfonamide;
6-(5-(azetidin-1-ylsulfonyl)pyridin-3-yl)-8-fluoro-[1,2,4]triazolo[1,5-a]pyridin-2-amine;
5-(2-amino-8-fluoro-[1,2,4]triazolo[1,5-a]pyridin-6-yl)-N-(2,2,2-trifluoroethyl)pyridine-3-sulfonamide;
5-(2-amino-8-fluoro-[1,2,4]triazolo[1,5-a]pyridin-6-yl)-N-ethyl-N-methylpyridine-3-sulfonamide;
8-fluoro-6-(3-(methylsulfonyl)phenyl)-[1,2,4]triazolo[1,5-a]pyridin-2-amine;
6-(6-amino-5-(trifluoromethyl)pyridin-3-yl)-[1,2,4]triazolo[1,5-a]pyridin-2-amine;
5-(3-(2-amino-[1,2,4]triazolo[1,5-a]pyridin-6-yl)phenylsulfonamido)pentanoic acid;
4-(3-(2-amino-[1,2,4]triazolo[1,5-a]pyridin-6-yl)phenylsulfonamido)butanoic acid;
6-(5-(benzylthio)pyridin-3-yl)-[1,2,4]triazolo[1,5-a]pyridin-2-amine;
8-fluoro-6-(5-(trifluoromethyl)pyridin-3-yl)-[1,2,4]triazolo[1,5-a]pyridin-2-amine;
6-(4-fluorophenyl)-[1,2,4]triazolo[1,5-a]pyridin-2-amine hydrochloride;
6-(3-methoxyphenyl)-[1,2,4]triazolo[1,5-a]pyridin-2-amine hydrochloride;
6-(3,4,5-trimethoxyphenyl)-[1,2,4]triazolo[1,5-a]pyridin-2-amine hydrochloride;
6-m-tolyl-[1,2,4]triazolo[1,5-a]pyridin-2-amine;
3-(2-amino-[1,2,4]triazolo[1,5-a]pyridin-6-yl)benzonitrile;
6-(3-chlorophenyl)-[1,2,4]triazolo[1,5-a]pyridin-2-amine;
6-phenyl-[1,2,4]triazolo[1,5-a]pyridin-2-amine;
6-(2-methoxyphenyl)-[1,2,4]triazolo[1,5-a]pyridin-2-amine;
6-(3-(ethylamino)phenyl)-[1,2,4]triazolo[1,5-a]pyridin-2-amine;
4-(2-amino-[1,2,4]triazolo[1,5-a]pyridin-6-yl)benzamide;
6-(pyrimidin-5-yl)-[1,2,4]triazolo[1,5-a]pyridin-2-amine hydrochloride;
6-(1-methyl-1H-pyrazol-4-yl)-[1,2,4]triazolo[1,5-a]pyridin-2-amine hydrochloride;
3-(2-amino-[1,2,4]triazolo[1,5-a]pyridin-6-yl)phenol;
6-(3-(trifluoromethyl)phenyl)-[1,2,4]triazolo[1,5-a]pyridin-2-amine hydrochloride;
6-(benzo[d][1,3]dioxol-5-yl)-[1,2,4]triazolo[1,5-a]pyridin-2-amine hydrochloride;
6-(3,4-dimethoxyphenyl)-7-methyl-[1,2,4]triazolo[1,5-a]pyridin-2-amine hydrochloride;
6-(3,4-difluorophenyl)-[1,2,4]triazolo[1,5-a]pyridin-2-amine hydrochloride;
6-(3-fluorophenyl)-[1,2,4]triazolo[1,5-a]pyridin-2-amine hydrochloride;
6-(4-methoxyphenyl)-[1,2,4]triazolo[1,5-a]pyridin-2-amine;
N-(3-(2-amino-[1,2,4]triazolo[1,5-a]pyridin-6-yl)phenyl)acetamide;
6-(2,3-dihydrobenzo[b][1,4]dioxin-6-yl)-[1,2,4]triazolo[1,5-a]pyridin-2-amine;
3-(2-amino-[1,2,4]triazolo[1,5-a]pyridin-6-yl)benzenesulfonamide;
4-(2-amino-[1,2,4]triazolo[1,5-a]pyridin-6-yl)benzenesulfonamide;
3-(2-amino-[1,2,4]triazolo[1,5-a]pyridin-6-yl)benzoic acid;
6-(pyridin-4-yl)-[1,2,4]triazolo[1,5-a]pyridin-2-amine;
6-(1H-pyrazol-3-yl)-[1,2,4]triazolo[1,5-a]pyridin-2-amine;
6-(thiophen-2-yl)-[1,2,4]triazolo[1,5-a]pyridin-2-amine; and
6-(1H-pyrazol-4-yl)-[1,2,4]triazolo[1,5-a]pyridin-2-amine.

23. A pharmaceutical composition according to claim 1 in combination with one or more other pharmaceutical compositions.

24. A pharmaceutical composition according to claim 23, comprising one or more additional compounds or pharmaceutically acceptable salts thereof selected from the group consisting of compounds of formula (I) or a pharmaceutically acceptable salt thereof as defined in claim 1 and not being the first compound; other P13K inhibitors, steroids, leukotriene antagonists, antihistamines, cyclosporine or rapamycin.

25. A pharmaceutical composition according to claim 1, wherein:
$R^1$ and $R^2$ are independently H or $CH_3$;
$R^3$ is H, $CH_3$ or halogen;
$T^1$ is unsubstituted phenyl; substituted phenyl; unsubstituted 4 to 7 membered heterocyclyl; substituted 4 to 7 membered heterocyclyl; unsubstituted 9 to 11 membered heterobicyclyl; or substituted 9 to 11 membered heterobicyclyl;
$R^5$ is oxo (=O), where the ring is at least partially substituted; F; Cl; CN; $N(R^7R^{7a})$; $OR^7$; $C(O)OR^7$; $C(O)N(R^7R^{7a})$; $N(R^7)S(O)_2R^{7a}$; $S(O)_2N(R^7R^{7a})$; $S(O)_2R^7$; $S(O)R^7$; $N(R^7)C(O)R^{7a}$; or $C_{1-6}$ alkyl, which is optionally substituted with one or more $R^8$;
$R^7$, $R^{7a}$ are independently selected from the group consisting of H; $CH_3$; $CH_2CH_3$; n-butyl; tert.-butyl; iso-propyl; n-pentyl; isopentyl; neopentyl; 2-ethylbutyl; $CF_3$; $CH_2CH_2OH$; $CH_2CH_2CH_2OH$; $CH_2C(CH_3)_2CH_2OH$; $CH_2CH_2OCH_3$; $CH_2CH_2NH_2$; $CH_2CF_3$; $CH_2CH_2CF_3$; $CH_2CH_2CH_2CF_3$; $C(CH_3)_2CF_3$; $CH_2CH_2NHCH_3$; $CH_2CH_2N(CH_3)_2$; $CH_2CH_2CH2N(CH_3)2$; $CH_2C(O)OH$; and $CH_2C(O)N(CH_3)_2$;
$R^8$ is F; Cl; Br; OH; $CH_3$; or $CH_2CH_3$;
$R^6$ is $S(O)_2N(R^9R^{9a})$; $N(R^9)S(O)_2R^{9a}$; $S(O)_2R^9$; $OR^9$; or $SR^9$;
$R^{9c}$ is $T^2$; $CH_2$-$T^2$; or $C_{1-4}$ alkyl-$T^2$;
$R^{9d}$ is H or methyl;

$T^2$ is phenyl; naphthyl; $C_{3-4}$ cycloalkyl; or 4 to 7 membered heterocyclyl, wherein $T^2$ is optionally substituted with up to three $R^{11}$; and $R^{11}$ is oxo (=O), where the ring is at least partially saturated; F; Cl; $CH_3$; $CH_2CH_3$; $CH_2CH_2CH_3$; $CH(CH_3)_2$; $CF_3$; OH; $OCH_3$; $OCF_3$; $NH_2$; $NHCH_3$; or $N(CH_3)_2$.

26. A pharmaceutical composition according to claim 25, wherein:

$T^1$ is unsubstituted, substituted with one $R^5$, two $R^5$, one $R^6$, two $R^6$, or one $R^5$ and one $R^6$; and $R^6$ is $S(O)_2N(R^{9c}R^{9d})$; $N(R^{9d})S(O)_2R^{9c}$; $S(O)_2R^{9c}$; or $OR^{9c}$.

27. A pharmaceutical composition according to claim 25, wherein:

$T^1$ is phenyl; pyrrolyl; furyl; thienyl; pyrazolyl; oxazolyl; thiazolyl; pyridyl and N-oxide thereof; pyrimidinyl; indolyl; indolinyl; indazolyl; quinolinyl; isoquinolinyl; benzodioxolyl; dihydrobenzo furyl; dihydrobenzoxazinyl; dihydrobenzodioxinyl; benzodioxanyl; or benzothiazole dioxide;

$R^5$ is oxo (=O), where the ring is at least partially substituted; F; Cl; $NH_2$; $NH(CH_3)$; $N(CH_3)_2$; $NH(CH_2)_2OH$; $N((CH_2)_2OH)_2$; OH; $OCH_3$; $OCF_3$; $OCH(CH_3)_2$; $CH_2OH$; $CH_2OCH_3$; $CH_2Br$; $CH_3$; $CH_2CH_3$; $CH(CH_3)_2$; $C(CH_3)_3$; $CF_3$; C(O)OH; $C(O)OCH_3$; $C(O)OCH_2CH_3$; $C(O)NH_2$; $C(O)NH(CH_3)$; $C(O)(CH_3)_2$; $C(O)NHCH_2CH_3$; $C(O)N(CH_3)CH_2CH_3$; $C(O)NHCH_2CH_2OH$; $C(O)N(CH_3)CH_2CH_2OH$; $C(O)NHCH_2CH_2OCH_3$; $C(O)N(CH_3)CH_2CH_2OCH_3$; $C(O)NHCH_2CH_2NH_2$; $C(O)N(CH_3)CH_2CH_2NH_2$; $C(O)NHCH_2CH_2NHCH_3$; $C(O)N(CH_3)CH_2CH_2NHCH_3$; $C(O)NHCH_2CH_2N(CH_3)_2$; $C(O)N(CH_3)CH_2CH_2N(CH_3)_2$; $HNC(O)H_3$; $S(O)_2CH_3$; $S(O)CH_3$; $S(O)_2NH_2$; $S(O)_2NHC(CH_3)_3$; $S(O)_2NHCH_2CH(CH_2CH_3)_2$; $S(O)_2 NH(CH_2)_2OH$; $S(O)_2NH(CH_2)_2CF_3$; $S(O)_2NH(CH_2)_3 CF_3$; $S(O)_2NH(CH_2)_3OH$; $S(O)_2NHCH_2C(CH_3)_2 CH_2OH$; $S(O)_2NH(CH_2)_2OCH_3$; or $NHS(O)_2 CH_3$; and $T^2$ is imidazolidinyl; pyrrolidinyl; piperidinyl; piperizinyl; isoindolinyl; oxazolyl; dihydroisoquinolinyl; morpholinyl; pyranyl; azepanyl; azetidinyl; thiamorpholine dioxide; cyclopropyl; cyclobutyl; cyclopentyl; cyclohexyl; cycloheptyl; phenyl; or naphthyl.

28. A pharmaceutical composition according to claim 27, wherein $T^1$ is phenyl or pyridyl.

* * * * *